US006579872B1

(12) United States Patent
Brown et al.

(10) Patent No.: US 6,579,872 B1
(45) Date of Patent: Jun. 17, 2003

(54) BEZAMIDE DERIVATIVES FOR THE TREATMENT OF DISEASES MEDIATED BY CYTOKINES

(75) Inventors: Dearg S Brown, Macclesfield (GB); George R Brown, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/674,560

(22) PCT Filed: May 11, 1999

(86) PCT No.: PCT/GB99/01489

§ 371 (c)(1),
(2), (4) Date: Nov. 2, 2000

(87) PCT Pub. No.: WO99/59959

PCT Pub. Date: Nov. 25, 1999

(30) Foreign Application Priority Data

May 15, 1998 (GB) ............................................. 9810357
Oct. 16, 1998 (GB) ............................................. 9822483

(51) Int. Cl.[7] ..................... A61K 31/535; C07D 413/02; A61P 43/00
(52) U.S. Cl. ................................ 514/235.5; 514/235.8; 514/236.2; 544/111; 544/121; 544/122; 544/129
(58) Field of Search .................................. 544/121, 122, 544/129, 111; 514/235.5, 235.8, 236.2

(56) References Cited

U.S. PATENT DOCUMENTS

| 1,903,899 A | 4/1933 | Laska et al. | |
| 1,909,960 A | 5/1933 | Hitch | |
| 3,211,555 A | 10/1965 | Mory et al. | 96/99 |
| 3,755,332 A | 8/1973 | Wasley et al. | 260/288 |
| 4,328,553 A | 5/1982 | Fredriksen et al. | |
| 4,356,392 A | 10/1982 | Wittekoek et al. | |
| 4,367,328 A | 1/1983 | Bertram et al. | 528/98 |
| 4,391,524 A | 7/1983 | Steigmeier et al. | |
| 4,441,124 A | 4/1984 | Heebner et al. | |
| 4,524,168 A | 6/1985 | Wick | 524/190 |
| 4,614,427 A | 9/1986 | Koizumi et al. | |
| 4,749,729 A | 6/1988 | Kohli et al. | 523/468 |
| 4,788,431 A | 11/1988 | Eckes et al. | |
| 4,889,998 A | 12/1989 | Hayano et al. | |
| 5,096,291 A | 3/1992 | Scott | |
| 5,317,380 A | 5/1994 | Allemand | |
| 5,585,629 A | 12/1996 | Doran et al. | |
| 5,917,588 A | 6/1999 | Addiego | |
| 5,948,972 A | 9/1999 | Samsavar et al. | |
| 6,020,957 A | 2/2000 | Rosengaus et al. | |
| 6,107,637 A | 8/2000 | Watanabe et al. | |
| 6,140,644 A | 10/2000 | Kawanami et al. | |
| 6,172,365 B1 | 1/2001 | Hiroi et al. | |
| 6,208,407 B1 | 3/2001 | Loopstra | |

FOREIGN PATENT DOCUMENTS

| DE | 522 788 | 3/1931 |
| DE | 28 12 252 | 10/1979 |
| EP | 0 635 507 | 1/1995 |
| EP | 0 849 256 | 6/1998 |
| JP | 50105558 | * 8/1975 |
| WO | WO 93/04170 | 3/1993 |
| WO | WO 95/19774 | 7/1995 |
| WO | WO 97/05878 | 2/1997 |
| WO | WO 97/13771 | 4/1997 |
| WO | WO 97/32853 | 9/1997 |
| WO | WO 98/06715 | 2/1998 |
| WO | WO 98/22103 | 5/1998 |
| WO | WO 99/15164 | 4/1999 |
| WO | WO 99/59959 | 11/1999 |
| WO | WO 99/59960 | 11/1999 |
| WO | WO 00/07980 | 2/2000 |
| WO | WO 00/07991 | 2/2000 |
| WO | WO 00/18738 | 4/2000 |
| WO | WO 00/20402 | 4/2000 |
| WO | WO 00/55120 | 9/2000 |
| WO | WO 00/55153 | 9/2000 |
| WO | WO 00/56738 | 9/2000 |

OTHER PUBLICATIONS

Hanson G J: "Inhibitors of p38 kinase" Expert Opinion on Therapeutic Patents, vol. 7, No. 7, Jan. 1, 1997, pp. 729–733, XP002086152 ISSN: 1354–3776 cited in the application.
Adams et al., "Search for trypanocides. III. Analogs of suramin.", Chemical Abstracts, vol. 51, 1957, columns 5068 and 5069.
Ando et al., "Producing azo lake pigments"; Chemical Abstract, vol. 106, Abstract No. 215574 Aug. 30, 1988.
Ando et al., "Substituent Shielding Parameters of Ffluorine–19 NMR on Polyfluoroaromatic Compounds Dissolved in Dimethyl Sulfoxide–$d_6$", Magn. Reson.Chem. 639–45, 1995, Chemical Abstract: 123:227514, 1995.
Ashton et al., "New Low–Density Lipoprotein Receptor Upregulators Acting via a Novel Mechanism", J. Med. Chem., 1996, vol. 39, pp. 3343–3356.

(List continued on next page.)

Primary Examiner—Joseph K. McKane
Assistant Examiner—Andrea D. Small
(74) Attorney, Agent, or Firm—Morgan, Lewis & Bockius, LLP

(57) ABSTRACT

The invention concerns the use of amide derivatives of formula (I) wherein: $R^1$ and $R^2$ are substituents such as hydroxy, $C_{1-6}$alkoxy, mercapto, $C_{1-6}$alkylthio, amino, $C_{1-6}$alkylamino and di-($C_{1-6}$alkyl)amino; m and p are independently 0–3; $R^3$ is $C_{1-4}$alkyl; q is 0–4; and $R^4$ is aryl or cycloalkyl; or a pharmaceutically acceptable salt thereof in the manufacture of a medicament for use in the treatment of diseases or medical conditions mediated by cytokines.

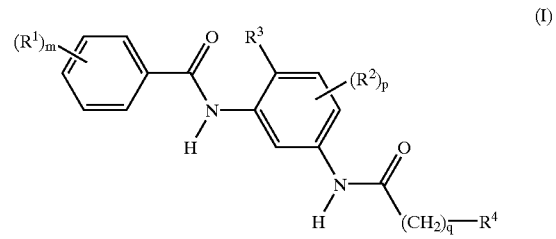

10 Claims, No Drawings

OTHER PUBLICATIONS

Beilstein Reg. No. 2164595, 1989.
Beilstein Reg. No. 3166971, 1990.
Beilstein Reg. No. 3451759, 1990.
Beilstein Reg. No. 3480574, 1990.
Beilstein Reg. No. 3483669, 1990.
Beilstein Reg. No. 3534091, 1990.
Chemical Abstract No. 12076g, vol. 65, 1966.
Chemical Abstract No. 12932a, vol. 51, 1957.
Denny et al., "Potential Antitumour Agents. 29. Quantitative Structure–Activity Relationships for the Antileukemic Bisquaternary Ammonium Heterocycles", Journal of Medicinal Chemistry, Feb. 1979, vol. 22, No. 2, pp. 134–150.
Hamuro et al., "Novel Folding Patterns in a Family of Oligoanthranilamides: . . . Secondary Structures", J. Amer. Chem. Soc., 1997, pp. 10587–10593.
Ito et al., Photosensitive material containing microencapsulated hydrazine derivatives; Chemical Abstract, vol. 118, Abstract No. 70021, Jun. 1992.
Kelley et al., "Antirhinorvirus Activity of 6–Anilino–9–benxyl–2–chloro–9H–purines", J. Med. Chem., 1990, vol. 33, pp. 1360–1363, XP–002140324.
Lesiak, "New amides of pyrrole–N– and indole–N–caboxylic acids", Chemical Abstracts, No. 126704v, XP–002121335, 1971.
Makoto; "Amide and Its Use"; Patent Abstracts of Japan, Abstract No. 09124571, May 13, 1997, also attached: Abstract (Derwent); XP 002086154.

Mühlbach, "Pyrazoles—A Novel Class of Blocking Agents for Isocyanates", Journal of Polymer Science: Part A: Polymer Chemistry, vol. 32, Mar. 1994, pp. 753–765.

Myers et al., "The Preparation and SAR of 4–(Anilino), 4–(Phenoxy), and 4–(Thiophenoxy)–Quinazoline: Inhibitors of P56$^{lck}$ and EGF–R Tyrosine Kinase Activity"; Bioorganic & Chemistery Letters, vol. 7, No. 4, pp. 417–420, 1997.

Petrova et al., "Determination of the Structure of the Oxidative . . . by Spectroscopic Methods", Journal of Molecular Structure, vol. 142, 1986, pp. 459–462.

Sugawara et al., Kogyo Kaguku Zasshi 72(11) 2425–2429, 1969, Chemical Abstract: 72:66514, 1970.

Thompson et al., "Tyrosine Kinase Inhibitors. 7.7–Amino–4–(phenylamino– and 7–Amino–4–[(phenylmethyl)amino]purido4,3–dpyrimidines: A New Class of Inhibitors of the Tyrosine Kinase Activity of the Epidermal Growth Factor Receptor"; Journal of Medicinal Chemistry, US, American Chemical Society, vol. 38, No. 19, 1995, pp. 3780–3788, XP002140323.

Wang et al., "Low–valent Titanium–induced Reactions of Substituted Nitrobenzenes", J. Chem. Research, 1998, pp. 182–183.

* cited by examiner

BEZAMIDE DERIVATIVES FOR THE TREATMENT OF DISEASES MEDIATED BY CYTOKINES

This application is the national phase of international application PCT/GB99/01489 filed May 11, 1999.

This invention concerns certain amide derivatives which are useful as inhibitors of cytokine mediated disease. The invention also concerns processes for the manufacture of the amide derivatives of the invention, pharmaceutical compositions containing them and their use in therapeutic methods, for example by virtue of inhibition of cytokine mediated disease.

The amide derivatives disclosed in the present invention are inhibitors of the production of cytokines such as Tumour Necrosis Factor (hereinafter TNF), for example TNFα, and various members of the interleukin (hereinafter IL) family, for example IL-1, IL-6 and IL-8. Accordingly the compounds of the invention will be useful in the treatment of diseases or medical conditions in which excessive production of cytokines occurs, for example excessive production of TNFα or IL-1. It is known that cytokines are produced by a wide variety of cells such as monocytes and macrophages and that they give rise to a variety of physiological effects which are believed to be important in disease or medical conditions such as inflammation and immunoregulation. For example, TNFα and IL-1 have been implicated in the cell signalling cascade which is believed to contribute to the pathology of disease states such as inflammatory and allergic diseases and cytokine-induced toxicity. It is also known that, in certain cellular systems, TNFα production precedes and mediates the production of other cytokines such as IL-1.

Abnormal levels of cytokines have also been implicated in, for example, the production of physiologically-active eicosanoids such as the prostaglandins and leukotrienes, the stimulation of the release of proteolytic enzymes such as collagenase, the activation of the immune system, for example by stimulation of T-helper cells, the activation of osteoclast activity leading to the resorption of calcium, the stimulation of the release of proteoglycans from, for example, cartilage, the stimulation of cell proliferation and to angiogenesis.

Cytokines are also believed to be implicated in the production and development of disease states such as inflammatory and allergic diseases, for example inflammation of the joints (especially rheumatoid arthritis, osteoarthritis and gout), inflammation of the gastrointestinal tract (especially inflammatory bowel disease, ulcerative colitis, Crohn's disease and gastritis), skin disease (especially psoriasis, eczema and dermatitis) and respiratory disease (especially asthma, bronchitis, allergic rhinitis and adult respiratory distress syndrome), and in the production and development of various cardiovascular and cerebrovascular disorders such as congestive heart failure, myocardial infarction, the formation of atherosclerotic plaques, hypertension, platelet aggregation, angina, stroke, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoperosis and periodontitis, and the abnormal changes in bone metabolism which may accompany rheumatoid arthritis and osteoarthritis. Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke. Excessive cytokine production has also been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

Evidence of the central role played by TNFα in the cell signalling cascade which gives rise to rheumatoid arthritis is provided by the efficacy in clinical studies of antibodies of TNFα (*The Lancet,* 1994, 344, 1125 and *British Journal of Rheumatology,* 1995, 34, 334).

Thus cytokines such as TNFα and IL-1 are believed to be important mediators of a considerable range of diseases and medical conditions. Accordingly it is expected that inhibition of the production of and/or effects of these cytokines will be of benefit in the prophylaxis, control or treatment of such diseases and medical conditions.

Without wishing to imply that the compounds disclosed in the present invention possess pharmacological activity only by virtue of an effect on a single biological process, it is believed that the compounds inhibit the effects of cytokines by virtue of inhibition of the enzyme p38 kinase. p38 kinase, otherwise known as cytokine suppressive binding protein (hereinafter CSBP) and reactivating kinase (hereinafter RK), is a member of the mitogen-activated protein (hereinafter MAP) kinase family of enzymes which is known to be activated by physiological stress such as that induced by ionising radiation, cytotoxic agents, and toxins, for example endotoxins such as bacterial lipopolysaccharide, and by a variety of agents such as the cytokines, for example TNFα and IL-1. It is known that p38 kinase phosphorylates certain intracellular proteins which are involved in the cascade of enzymatic steps which leads to the biosynthesis and excretion of cytokines such as TNFα and IL-1. Known inhibitors of p38 kinase have been reviewed by G. J. Hanson in *Expert Opinions on Therapeutic Patents,* 1997, 7, 729–733. p38 kinase is known to exist in isoforms identified as p38α and p38β.

The compounds disclosed in the present invention are inhibitors of the production of cytokines such as TNF, in particular of TNFα, and various interleukins, in particular IL-1.

It is known from *J. Med. Chem.,* 1996, 39, 3343–3356, that certain benzamide derivatives can upregulate the expression of the low density lipoprotein (LDL) receptor in human hepatocyte cells. The disclosed compounds included certain N-(2-methylphenyl)-, N-(2-methoxyphenyl)- and N-(2-halogenophenyl)-benzamide derivatives. One of the disclosed compounds is N-[5-(3-cyclohexylpropionamido)-2-methylphenyl]-3,4-methylenedioxybenzamide.

It is known from U.S. Pat. No. 4,367,328 (Chemical Abstracts, 98, 144515) that certain epoxy resins may be prepared from the chemical intermediate N-{5-[2-(2,3-epoxypropoxy)benzamido]-2-methylphenyl}-2-(2,3-epoxypropoxy)benzamide.

According to one aspect of the present invention there is provided a compound of the Formula I

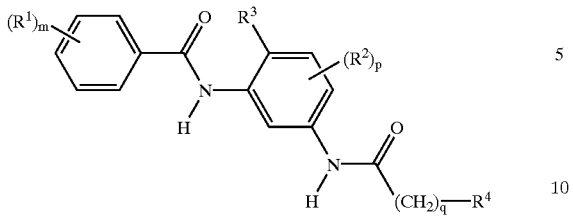

Formula I wherein
$R^3$ is (1–6C)alkyl or halogeno;
$R^1$ is selected from the substituents defined in paragraphs (A) and (B) hereinafter:
  (A) hydroxy, halogeno, trifluoromethyl, cyano, mercapto, nitro, amino, carboxy, carbamoyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (1–6C)alkanoyl, cyano-(1–6C)alkyl, hydroxy-(1–6C)alkyl, amino-(1–6C)alkyl, (1–6C)alkanoyloxy, (1–6C)alkanoylamino, (1–6C)alkoxycarbonylamino, N-(1–6C)alkylsulphamoyl, N,N-di-[(1–6C)alkyl]sulphamoyl, aryl, aryl-(1–6C)alkyl, aryl-(1–6C)alkoxy, arylthio, arylsulphinyl, arylsulphonyl, heteroaryl, heteroaryl-(1–6C)alkyl, heterocyclyl and heterocyclyl-(1–6C)alkyl; and
  (B) (1–3C)alkylenedioxy, halogeno-(1–6C)alkyl, (1–6C)alkoxy-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, (1–6C)alkylamino-(1–6C)alkyl, di-[(1–6C)alkyl]amino-(1–6C)alkyl, hydroxy-(2–6C)alkoxy-(1–6C)alkyl, (1–6C)alkoxy-(2–6C)alkoxy-(1–6C)alkyl, hydroxy-(2–6C)alkylamino-(1–6C)alkyl, (1–6C)alkoxy-(2–6C)alkylamino-(1–6C)alkyl, amino-(2–6C)alkylamino-(1–6C)alkyl, (1–6C)alkylamino-(2–6C)alkylamino-(1–6C)alkyl, di-[(1–6C)alkyl]amino-(2–6C)alkylamino-(1–6C)alkyl, (1–6C)alkylthio-(1–6C)alkyl, hydroxy-(2–6C)alkylthio-(1–6C)alkyl, (1–6C)alkoxy-(2–6C)alkylthio-(1–6C)alkyl, hydroxy-N-(1–6C)alkyl-(2–6C)alkylamino-(1–6C)alkyl, (1–6C)alkoxy-N-(1–6C)alkyl-(2–6C)alkylamino-(1–6C)alkyl, amino-N-(1–6C)alkyl-(2–6C)alkylamino-(1–6C)alkyl, (1–6C)alkylamino-N-(1–6C)alkyl-(2–6C)alkylamino-(1–6C)alkyl, di-[(1–6C)alkyl]amino-N-(1–6C)alkyl-(2–6C)alkylamino-(1–6C)alkyl, trifluoromethoxy, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, (1–6C)alkanesulphonylamino, N-(1–6C)alkyl-(1–6C)alkanesulphonylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryloxy, arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, aryl-(1–6C)alkoxy-(1–6C)alkyl, aryl-(1–6C)alkylamino-(1–6C)alkyl, N-(1–6C)alkyl-aryl-(1–6C)alkylamino-(1–6C)alkyl, heteroaryloxy, heteroaryl-(1–6C)alkoxy, heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyloxy, heterocyclyl-(1–6C)alkoxy, heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl and N-(1–6C)alkyl-heterocyclyl-(1–6C)alkylamino-(1–6C)alkyl;

and wherein any aryl, heteroaryl or heterocyclyl group in a $R^1$ substituent may optionally bear 1 or 2 substituents selected from halogeno, (1–6C)alkyl and (1–6C)alkoxy;

and wherein any of the substituents defined in paragraph (B) hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino and di-[(1–6C)alkyl]amino;

m is 1, 2 or 3;

$R^2$ is hydroxy, halogeno, trifluoromethyl, cyano, mercapto, nitro, amino, carboxy, (1–6C)alkyl, (2–6C)alkenyl, (2–6C)alkynyl, (1–6C)alkoxy, (1–6C)alkylamino or di-[(1–6C)alkyl]amino;

p is 0, 1 or 2;

q is 0, 1, 2, 3 or 4; and $R^4$ is aryl or cycloalkyl wherein $R^4$ is substituted with 1, 2 or 3 substituents selected from paragraphs (C) and (D) hereinafter:

(C) hydrogen, hydroxy, halogeno, trifluoromethyl, cyano, mercapto, nitro, amino, carboxy, carbamoyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (1–6C)alkanoyl, cyano-(1–6C)alkyl, hydroxy-(1–6C)alkyl, amino-(1–6C)alkyl, (1–6C)alkanoyloxy, (1–6C)alkanoylamino, (1–6C)alkoxycarbonylamino, N-(1–6C)alkylsulphamoyl, N,N-di-[(1–6C)alkyl]sulphamoyl, aryl, aryl-(1–6C)alkyl, aryl-(1–6C)alkoxy, arylthio, arylsulphinyl, arylsulphonyl, heteroaryl, heteroaryl-(1–6C)alkyl, heterocyclyl and heterocyclyl-(1–6C)alkyl; and (D) (1–3C)alkylenedioxy, halogeno-(1–6C)alkyl, (1–6C)alkoxy-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl(1–6C)alkyl, N,N-di-[(1–6C)alkyl]carbamoyl-(1–6C)alkyl, (1–6C)alkylamino-(1–6C)alkyl, di-[(1–6C)alkyl]amino-(1–6C)alkyl, hydroxy-(2–6C)alkoxy-(1–6C)alkyl, (1–6C)alkoxy-(2–6C)alkoxy-(1–6C)alkyl, hydroxy-(2–6C)alkylamino-(1–6C)alkoxy-(2–6C)alkylamino-(1–6C)alkyl, amino-(2–6C)alkylamino-(1–6C)alkyl, (1–6C)alkylamino-(2–6C)alkylamino-(1–6C)alkyl, di-[(1–6C)alkyl]amino-(2–6C)alkylamino-(1–6C)alkyl, (1–6C)alkylthio-(1–6C)alkyl, hydroxy-(2–6C)alkylthio-(1–6C)alkyl, (1–6C)alkoxy-(2–6C)alkylthio-(1–6C)alkyl, hydroxy-N-(1–6C)alkyl-(2–6C)alkylamino-(1–6C)alkyl, (1–6C)alkoxy-N-(1–6C)alkyl-(2–6C)alkylamino-(1–6C)alkyl, amino-N-(1–6C)alkyl-(2–6C)alkylamino-(1–6C)alkyl, (1–6C)alkylamino-N-(1–6C)alkyl-(2–6C)alkylamino-(1–6C)alkyl, di-[(1–6C)alkyl]amino-N-(1–6C)alkyl-(2–6C)alkylamino-(1–6C)alkyl, trifluoromethoxy, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, (1–6C)alkanesulphonylamino, N-(1–6C)alkyl-(1–6C)alkanesulphonylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryloxy, arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, aryl-(1–6C)alkoxy-(1–6C)alkyl, aryl-(1–6C)alkylamino-(1–6C)alkyl, N-(1–6-$^6$C)alkyl-aryl-(1–6C)alkylamino-(1–6C)alkyl, heteroaryloxy, heteroaryl-(1–6C)alkoxy, heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heteroaryl-(1–6C)alkoxy-(1–6C)alkyl, heteroaryl-(1–6C)alkylamino-(1–6C)alkyl, N-(1–6C)alkyl-heteroaryl-(1–6C)alkylamino-(1–6C)alkyl, heterocyclyloxy, heterocyclyl-(1–6C)alkoxy, heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl, heterocyclyl-(2–6C)alkanoylamino, heterocyclyl-(1–6C)alkoxy-(1–6C)alkyl, heterocyclyl-(1–6C)alkylamino-(1–6C)alkyl and N-(1–6C)alkyl-heterocyclyl-(1–6C)alkylamino-(1–6C)alkyl;

and wherein any aryl, heteroaryl or heterocyclyl group in a substituent on $R^4$ may optionally bear 1 or 2 substituents selected from halogeno, (1–6C)alkyl and (1–6C)alkoxy;

and wherein any of the substituents defined in paragraph (D) hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino and di-[(1–6C)alkyl]amino;

or a pharmaceutically-acceptable salt or in-vivo-cleavable ester thereof;

provided that a substituent on $R^4$ is selected from paragraph (C) hereinbefore only if at least one $R^1$ group is selected from paragraph (B) hereinbefore;

and provided that the compounds N-[5-(3-cyclohexylpropionamido)-2-methylphenyl]-3,4-methylenedioxybenzamide and N-{5-[2-(2,3-epoxypropoxy)benzamido]-2-methylphenyl}-2-(2,3-epoxypropoxy)benzamide are excluded.

According to a further aspect of the invention there is provided a compound of the Formula I wherein $R^3$ is (1–6C)alkyl or halogeno;

$R^1$ is selected from the substituents defined in paragraphs (A) and (B) hereinafter:

(A) hydroxy, halogeno, trifluoromethyl, cyano, mercapto, nitro, amino, carboxy, carbamoyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (1–6C)alkanoyl, cyano-(1–6C)alkyl, hydroxy-(1–6C)alkyl, amino-(1–6C)alkyl, (1–6C)alkanoyloxy, (1–6C)alkanoylamino, (1–6C)alkoxycarbonylamino, N-(1–6C)alkylsulphamoyl, N,N-di-[(1–6C)alkyl]sulphamoyl, aryl, aryl-(1–6C)alkyl, aryl-(1–6C)alkoxy, arylthio, arylsulphinyl, arylsulphonyl, heteroaryl, heteroaryl-(1–6C)alkyl, heterocyclyl and heterocyclyl-(1–6C)alkyl; and (B) (1–3C)alkylenedioxy, halogeno-(1–6C)alkyl, (1–6C)alkoxy-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, (1–6C)alkylamino-(1–6C)alkyl, di-[(1–6C)alkyl]amino-(1–6C)alkyl, hydroxy-(2–6C)alkoxy-(1–6C)alkyl, (1–6C)alkoxy-(2–6C)alkoxy-(1–6C)alkyl, hydroxy-(2–6C)alkylamino-(1–6C)alkyl, (1–6C)alkoxy-(2–6C)alkylamino-(1–6C)alkyl, amino-(2–6C)alkylamino-(1–6C)alkyl, (1–6C)alkylamino-(2–6C)alkylamino-(1–6C)alkyl, di-[(1–6C)alkyl]amino-(2–6C)alkylamino-(1–6C)alkyl, (1–6C)alkylthio-(1–6C)alkyl, hydroxy-(2–6C)alkylthio-(1–6C)alkyl, (1–6C)alkoxy-(2–6C)alkylthio-(1–6C)alkyl, halogeno-(2–6C)alkoxy, hydroxy-(2–6C)alkoxy, (1–6C)alkoxy-(2–6C)alkoxy, cyano-(1–6C)alkoxy, carboxy-(1–6C)alkoxy, (1–6C)alkoxycarbonyl-(1–6C)alkoxy, carbamoyl-(1–6C)alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N(1–6C)alkyl-(1–6C)alkylamino-(2–6C)alkylamino, N-(1–6C)alkyl-di-[(1–6C)alkyl]amino-(2–6C)alkylamino, (1–6C)alkanesulphonylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryloxy, arylamino, aryl-(1–6C)alkylamino, N-(1–6C)alkyl-aryl-(1–6C)alkylamino, aroylamino, arylsulphonylamino, N-arylsulphamoyl, aryl-(2–6C)alkanoylamino, heteroaryloxy, heteroaryl-(1–6C)alkoxy, heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyloxy, heterocyclyl-(1–6C)alkoxy, heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C)alkanoylamino, and wherein any aryl, heteroaryl or heterocyclyl group in a $R^1$ substituent may optionally bear 1 or 2 substituents selected from halogeno, (1–6C)alkyl and (1–6C)alkoxy;

m is 1, 2 or 3;

$R^2$ is hydroxy, halogeno, trifluoromethyl, cyano, mercapto, nitro, amino, carboxy, (1–6C)alkyl, (2–6C)alkenyl, (2–6C)alkynyl, (1–6C)alkoxy, (1–6C)alkylamino or di-[(1–6C)alkyl]amino;

p is 0, 1 or 2;

q is 0, 1, 2, 3 or 4; and $R^4$ is aryl or cycloalkyl wherein $R^4$ is substituted with 1, 2 or 3 substituents selected from paragraphs (C) and (D) hereinafter:

(C) hydroxy, halogeno, trifluoromethyl, cyano, mercapto, nitro, amino, carboxy, carbamoyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (1–6C)alkanoyl, cyano-(1–6C)alkyl, hydroxy-(1–6C)alkyl, amino-(6C)alkyl, (1–6C)alkanoyloxy, (1–6C)alkanoylamino, (1–6C)alkoxycarbonylamino, N-(1–6C)alkylsulphamoyl, N,N-di-[(1–6C)alkyl]sulphamoyl, aryl, aryl-(1–6C)alkyl, aryl-(1–6C)alkoxy, arylthio, arylsulphinyl, arylsulphonyl, heteroaryl, heteroaryl-(1–6C)alkyl, heterocyclyl and heterocyclyl-(1–6C)alkyl; and (D) (1–3C)alkylenedioxy, halogeno-(1–6C)alkyl, (1–6C)alkoxy-(1–6C)alkyl, carboxy-(1–6C)alkyl, (1–6C)alkoxycarbonyl-(1–6C)alkyl, carbamoyl-(1–6C)alkyl, N-(1–6C)alkylcarbamoyl-(1–6C)alkyl, N,N-di-[(1–6C)alkyl]carbamoyl-(1–6C)alkyl, (1–6C)alkylamino-(1–6C)alkyl, di-[(1–6C)alkyl]amino-(1–6C)alkyl, hydroxy-(2–6C)alkoxy-(1–6C)alkyl, (1–6C)alkoxy-(2–6C)alkoxy-(1–6C)alkyl, hydroxy-(2–6C)alkylamino-(1–6C)alkyl, (1–6C)alkoxy-(2–6C)alkylamino-(1–6C)alkyl, amino-(2–6C)alkylamino-(1–6C)alkyl, (1–6C)alkylamino-(2–6C)alkylamino-(1–6C)alkyl, di-[(1–6C)alkyl]amino-(2–6C)alkylamino-(1–6C)alkyl, (1–6C)alkylthio-(1–6C)alkyl, hydroxy-(2–6C)alkylthio-(1–6C)alkyl, (1–6C)alkoxy-(2–6C)alkylthio-(1–6C)

alkyl, halogeno-(2–6C)alkoxy, hydroxy-(2–6C) alkoxy, (1–6C)alkoxy-(2–6C)alkoxy, cyano-(1–6C) alkoxy, carboxy-(1–6C)alkoxy, (1–6C)alkoxycarbonyl-(1–6C)alkoxy, carbamoyl-(1–6C) alkoxy, N-(1–6C)alkylcarbamoyl-(1–6C)alkoxy, N,N-di-[(1–6C)alkyl]carbamoyl-(1–6C)alkoxy, amino-(2–6C)alkoxy, (1–6C)alkylamino-(2–6C)alkoxy, di-[(1–6C)alkyl]amino-(2–6C)alkoxy, halogeno-(2–6C)alkylamino, hydroxy-(2–6C)alkylamino, (1–6C)alkoxy-(2–6C)alkylamino, cyano-(1–6C)alkylamino, carboxy-(1–6C)alkylamino, (1–6C)alkoxycarbonyl-(1–6C)alkylamino, carbamoyl-(1–6C)alkylamino, N-(1–6C)alkylcarbamoyl-(1–6C)alkylamino, N,N-di-[(1–6C)alkyl]carbamoyl-(1–6C)alkylamino, amino-(2–6C)alkylamino, (1–6C)alkylamino-(2–6C)alkylamino, di-[(1–6C)alkyl]amino-(2–6C)alkylamino, N-(1–6C)alkyl-halogeno-(1–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-cyano-(1–6C)alkylamino, N-(1–6C)alkyl-carboxy-(1–6C)alkylamino, N-(1–6C)alkyl-(1–6C)alkoxycarbonyl-(1–6C)alkylamino, N-(1–6C)alkyl-carbamoyl-(1–6C)alkylamino, N-(1–6C)alkyl-N-(1–6C)alkylcarbamoyl-(1–6C)alkylamino, N-(1–6C)alkyl-N,N-di-[(1–6C)alkyl]carbamoyl-(1–6C)alkylamino, N-(1–6C)alkyl-amino-(2–6C)alkylamino, N-(1–6C)alkyl-(1–6C)alkylamino-(2–6C)alkylamino, N-(1–6C)alkyl-di-[(1–6C)alkyl]amino-(2–6C)alkylamino, (1–6C)alkanesulphonylamino, halogeno-(2–6C)alkanoylamino, hydroxy-(2–6C)alkanoylamino, (1–6C)alkoxy-(2–6C)alkanoylamino, cyano-(2–6C)alkanoylamino, carboxy-(2–6C)alkanoylamino, (1–6C)alkoxycarbonyl-(2–6C)alkanoylamino, carbamoyl-(2–6C)alkanoylamino, N-(1–6C)alkylcarbamoyl-(2–6C)alkanoylamino, N,N-di-[(1–6C)alkyl]carbamoyl-(2–6C)alkanoylamino, amino-(2–6C)alkanoylamino, (1–6C)alkylamino-(2–6C)alkanoylamino, di-[(1–6C)alkyl]amino-(2–6C)alkanoylamino, aryloxy, arylamino, aryl-(1–6C)alkylamino, N-(1–6C)alkyl-aryl1–6C)alkylamino, aroylamino, arylsulphonylamino, N-arylsulphamoyl, aryl-(2–6C)alkanoylamino, heteroaryloxy, heteroaryl-(1–6C)alkoxy, heteroarylamino, heteroaryl-(1–6C)alkylamino, N-(1–6C)alkyl-heteroaryl-(1–6C)alkylamino, heteroarylcarbonylamino, heteroarylsulphonylamino, N-heteroarylsulphamoyl, heteroaryl-(2–6C)alkanoylamino, heterocyclyloxy, heterocyclyl-(1–6C)alkoxy, heterocyclylamino, heterocyclyl-(1–6C)alkylamino, N-(1–6C)alkyl-heterocyclyl-(1–6C)alkylamino, heterocyclylcarbonylamino, heterocyclylsulphonylamino, N-heterocyclylsulphamoyl and heterocyclyl-(2–6C)alkanoylamino, and wherein any aryl, heteroaryl or heterocyclyl group in a substituent on $R^4$ may optionally bear 1 or 2 substituents selected from halogeno, (1–6C)alkyl and (1–6C)alkoxy;

or a pharmaceutically-acceptable salt or in-vivo-cleavable ester thereof;

provided that a substituent on $R^4$ is selected from paragraph (C) hereinbefore only if at least one $R^1$ group is selected from paragraph (B) hereinbefore.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting cytokines, in particular TNF. The synthesis of optically active forms may be carried out by standard techniques of organic chemistry well known in the art, for example by synthesis from optically active starting materials or by resolution of a racemic form. Similarly, inhibitory properties against TNF may be evaluated using the standard laboratory techniques referred to hereinafter.

Suitable values for the generic radicals referred to above include those set out below.

Suitable values for various $R^3$, $R^1$ or $R^2$ groups, or for various substituents on $R^4$ or on an aryl, heteroaryl or heterocyclyl group in $R^1$ or on a $R^4$ substituent include:

| | |
|---|---|
| for halogeno: | fluoro, chloro, bromo and iodo; |
| for (1–6C)alkyl: | methyl, ethyl, propyl, isopropyl and tert-butyl; |
| for (2–6C)alkenyl: | vinyl and allyl; |
| for (2–6C)alkynyl: | ethynyl and 2-propynyl; |
| for (1–6C)alkoxy: | methoxy, ethoxy, propoxy, isopropoxy and butoxy; |
| for (1–6C)alkylamino: | methylamino, ethylamino and propylamino; |
| for di-[(1–6C)alkyl]aamino: | dimethylamino, diethylamino and N-ethyl-N-methylamino. |

Suitable values for $R^1$ from paragraph (A) above and for a substituent on $R^4$ from paragraph (C) above include:

| | |
|---|---|
| for (1–6C)alkylthio: | methylthio, ethylthio and propylthio; |
| for (1–6C)alkylsulphinyl: | methylsulphinyl, ethylsulphinyl and propylsulphinyl; |
| for (1–6C)alkylsulphonyl: | methylsulphonyl, ethylsulphonyl and propylsulphonyl; |
| for (1–6C)alkoxycarbonyl: | methoxycarbonyl, ethoxycarbonyl, propoxycarbonyl and tert-butoxycarbonyl; |
| for N-(1–6C)alkylcarbamoyl: | N-methylcarbamoyl, N-ethylcarbamoyl and N-propylcarbamoyl; |
| for N,N-di-[(1–6C)alkyl]carbamoyl: | N,N-dimethylcarbamoyl, N-ethyl-N-methylcarbamoyl and N,N-diethylcarbamoyl; |
| for (1–6C)alkanoyl: | formyl, acetyl and propionyl; |
| for cyano-(1–6C)alkyl: | cyanomethyl, 2-cyanoethyl, 1-cyanoethyl and 3-cyanopropyl; |
| for hydroxy-(1–6C)alkyl: | hydroxymethyl, 2-hydroxyethyl, 1-hydroxyethyl and 3-hydroxypropyl; |
| for amino-(1–6C)alkyl: | aminomethyl, 2-aminoethyl, 1-aminoethyl and 3-aminopropyl; |
| for (1–6C)alkanoyloxy: | formyloxy, acetoxy and propionyloxy: |
| for (1–6C)alkanoylamino: | formamido, acetamido and propionamido; |

| | |
|---|---|
| for (1–6C)alkoxycarbonylamino: | methoxycarbonylamino; |
| for N-(1–6C)alkylsulphamoyl: | N-methylsulphamoyl and N-ethylsulphamoyl; |
| for N,N-di-[(1–6C)alkyl]sulphamoyl: | N,N-dimethylsulphamoyl. |

A suitable value for $R^1$ or $R^4$ or for a substituent on $R^4$ when it is aryl or for the aryl group when $R^1$ or the substituent on $R^4$ is arylthio, arylsulphinyl or arylsulphonyl is, for example, phenyl or naphthyl, preferably phenyl; when it is aryl-(1–6C)alkyl is, for example, benzyl and 2-phenylethyl; and when it is aryl-(1–6C)alkoxy is, for example, benzyloxy and 2-phenylethoxy.

A suitable value for $R^1$ or for a substituent on $R^4$ when it is heteroaryl or for the heteroaryl group when $R^1$ or the substituent on $R^4$ is heteroaryl-(1–6C)alkyl is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, quinolyl, isoquinolyl, quinazolinyl, quinoxalinyl or cinnolinyl. A heteroaryl-(1–6C)alkyl group may be, for example, a heteroarylmethyl or 2-heteroarylethyl group.

A suitable value for $R^1$ or for a substituent on $R^4$ when it is heterocyclyl or for the heterocyclyl group when $R^1$ or the substituent on $R^4$ is heterocyclyl-(1–6C)alkyl is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydropyranyl, pyrrolinyl, pyrrolidinyl, morpholinyl, piperidinyl, homopiperidinyl, piperazinyl, 4-(1–6C)alkylpiperazinyl (such as 4-methylpiperazinyl), homopiperazinyl, 4-(1–6C)alkylhomopiperazinyl, dihydropyridinyl, tetrahydropyridinyl, dihydropyrimidinyl or tetrahydropyrimidinyl. A heterocyclyl-(1–6C)alkyl group may be, for example, a heterocyclylmethyl or 2-heterocyclylethyl group.

Suitable values for $R^1$ from paragraph (B) above and for a substituent on $R^4$ from paragraph (D) above include:

| | |
|---|---|
| for (1–3C)alkylenedioxy: | methylenedioxy, ethylenedioxy and propylenedioxy; |
| for halogeno-(1–6C)alkyl: | fluoromethyl, chloromethyl, bromomethyl, difluoromethyl, dichloromethyl, dibromomethyl, 2-fluoroethyl, 2-chloroethyl and 2-bromoethyl; |
| for (1–4C)alkoxy-(1–6C)alkyl: | methoxymethyl, ethoxymethyl, 1-methoxyethyl. 2-methoxyethyl, 2-ethoxyethyl and 3-methoxypropyl; |
| for carboxy-(1–6C)alkyl: | carboxymethyl, 1-carboxyethyl, 2-carboxyethyl and 3-carboxypropyl; |
| for (1–6C)alkoxycarbonyl-(1–6C)alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for carbamoyl-(1–6C)alkyl: | carbamoylmethyl, 1-carbamoylethyl, 2-carbamoylethyl and 3-carbamoylpropyl; |
| for N-(1–6C)alkylcarbamoyl-(1–6C)alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-[(1–6C)alkyl]carbamoyl-(1–6C)alkyl: | N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; |
| for (1–6C)alkylamino-(1–6C)alkyl: | methylaminomethyl, ethylaminomethyl, 1-methylaminoethyl, 2-methylaminoethyl, 2-ethylaminoethyl and 3-methylaminopropyl; |
| for di-[(1–6C)alkyl]amino-(1–6C)alkyl: | dimethylaminomethyl, diethylaminomethyl, 1-dimethylaminoethyl, 2-dimethylaminoethyl and 3-dimethylaminopropyl; |
| for hydroxy-(2–6C)alkoxy-(1–6C)alkyl: | 2-hydroxyethoxymethyl, 3-hydroxypropoxymethyl and 2-(2-hydroxyethoxy)ethyl; |
| for (1–6C)alkoxy-(2–6C)alkoxy-(1–6C)alkyl: | 2-methoxyethoxymethyl, 3-methoxypropoxymethyl and 2-(2-methoxyethoxy)ethyl; |
| for hydroxy-(2–6C)alkylamino-(1–6C)alkyl: | 2-hydroxyethylaminomethyl, 3-hydroxypropylaminomethyl and 2-(2-hydroxyethylamino)ethyl; |
| for (1–6C)alkoxy-(2–6C)alkylamino-(1–6C)alkyl: | 2-methoxyethylaminomethyl, 3-methoxypropylaminomethyl and 2-(2-methoxyethylamino)ethyl; |
| for amino-(2–6C)alkylamino-(1–6C)alkyl: | 2-aminoethylaminomethyl, 3-aminopropylaminomethyl and 2-(2-aminoethylamino)ethyl; |
| for (1–6C)alkylamino-(2–6C)alkylamino-(1–6C)alkyl: | 2-methylaminoethylaminomethyl, 3-ethylaminopropylaminomethyl and 2-(2-methylaminoethylamino)ethyl; |
| for di-[(1–6C)alkyl]amino-(2–6C)alkylamino-(1–6C)alkyl: | 2-dimethylaminoethylaminomethyl, 3-dimethylaminopropylaminomethyl and 3-(2-diethylaminoethylamino)propyl; |
| for (1–6C)alkylthio-(1–6C)alkyl: | methylthiomethyl, 2-ethylthioethyl and 3-methylthiopropyl; |
| for hydroxy-(2–6C)alkylthio-(1–6C)alkyl: | 2-hydroxyethylthiomethyl, 3-hydroxypropylthiomethyl and 2-(2-hydroxyethylthio)ethyl; |

-continued

| | |
|---|---|
| for (1–6C)alkoxy-(2–6C)alkylthio-(1–6C)alkyl: | 2-methoxyethylthiomethyl, 3-methoxypropylthiomethyl and 2-(2-ethoxyethylthio)ethyl; |
| for hydroxy-N-(1–6C)alkyl-(2–6C)alkylamino-(–6C)alkyl: | N-methyl-2-hydroxyethylaminomethyl, N-ethyl-3-hydroxypropyl-aminomethyl and 2-(N-methyl-2-hydroxyethylamino)ethyl; |
| for (1–6C)alkoxy-N-(1–6C)alkyl-(2–6C)alkylamino-(1–6C)alkyl: | N-methyl-2-methoxyethylaminomethyl, N-ethyl-3-methoxypropyl-aminomethyl and 2-(N-methyl-2-methoxyethylamino)ethyl; |
| for amino-N-(1–6C)alkyl-(2–6C)alkylamino-(1–6C)alkyl: | N-methyl-N-(2-aminoethyl)aminomethyl, N-ethyl-N-(3-aminopropyl)-aminomethyl and 2-[N-methyl-N-(2-aminoethyl)amino]ethyl; |
| for (1–6C)alkylamino-N-(1–6C)alkyl-(2–6C)alkylamino-(1–6C)alkyl: | N-methyl-N-(2-methylaminoethyl)-aminomethyl, N-ethyl-N-(3-ethylaminopropyl)-aminomethyl and 2-[N-methyl-N-(2-methylaminoethyl)amino]ethyl; |
| for di-[(1–6C)alkyl]amino-N-(1–6C)alkyl-(2–6C)alkylamino-(1–6C)alkyl: | N-methyl-2-dimethylaminoethylaminomethyl, N-ethyl-3-dimethylaminopropylaminomethyl and 3-(N-methyl-2-diethylaminoethylamino)propyl; |
| for halogeno-(2–6C)alkoxy: | 2-chloroethoxy, 2-bromoethoxy and 3-chloropropoxy; |
| for hydroxy-(2–6C)alkoxy: | 2-hydroxyethoxy, 3-hydroxypropoxy, 2-hydroxy-2-methylethoxy and 4-hydroxybutoxy; |
| for (1–6C)alkoxy-(2–6C)alkoxy: | 2-methoxyethoxy, 2-ethoxyethoxy, 3-methoxypropoxy, 2-methoxy-1-methylethoxy and 4-ethoxybutoxy; |
| for cyano-(1–6C)alkoxy: | cyanomethoxy, 2-cyanoethoxy and 3-cyanopropoxy; |
| for carboxy-(1–6C)alkoxy: | carboxymethoxy, 2-carboxyethoxy and 3-carboxypropoxy; |
| for (1–6C)alkoxycarbonyl-(1–6C)alkoxy: | methoxycarbonylmethoxy, ethoxycarbonylmethoxy, tert-butoxycarbonylmethoxy, 2-methoxycarbonylethoxy and 3-ethoxycarbonylpropoxy; |
| for carbamoyl-(1–6C)alkoxy: | carbamoylmethoxy and 2-carbamoylethoxy; |
| for N-(1–6C)alkylcarbamoyl-(1–6C)alkoxy: | N-methylcarbamoylmethoxy, 2-(N-ethylcarbamoyl)ethoxy and 3-(N-methylcarbamoyl)propoxy; |
| for N,N-di-[(1–6C)alkyl]carbamoyl-(1–6C)alkoxy: | N,N-dimethylcarbamoylmethoxy, 2-(N,N-dimethylcarbamoyl)ethoxy and 3-(N,N-diethylcarbamoyl)propoxy; |
| for amino-(2–6C)alkoxy: | 2-aminoethoxy, 3-aminopropoxy and 4-aminobutoxy; |
| for (1–6C)alkylamino-(2–6C)alkoxy: | 2-methylaminoethoxy, 2-methylamino-1-methylethoxy and 3-ethylaminopropoxy; |
| for di-[(1–6C)alkyl]amino-(2–6C)alkoxy: | 2-dimethylaminoethoxy, 2-diethylaminoethoxy, 2-dimethylamino-2-methylethoxy and 3-dimethylaminopropoxy; |
| for halogeno-(2–6C)alkylamino: | 2-fluoroethylamino. 2-chloroethylamino. 2-bromoethylamino, 3-fluoropropylamino and 3-chloropropylamino; |
| for hydroxy-(2–6C)alkylamino: | 2-hydroxyethylamino, 3-hydroxypropylamino and 4-hydroxybutylamino; |
| for (1–6C)alkoxy-(2–6C)alkylamino: | 2-methoxyethylamino, 2-ethoxyethylamino, 3-methoxypropylamino and 3-ethoxypropylamino; |
| for cyano-(1–6C)alkylamino: | cyanomethylamino, 2-cyanoethylamino and 3-cyanopropylamino; |
| for carboxy-(1–6C)alkylamino: | carboxymethylamino, 2-carboxyethylamino and 3-carboxypropylamino; |
| for (1–6C)alkoxycarbonyl-(1–6C)alkylamino: | methoxycarbonylmethylamino, 2-(ethoxycarbonyl)ethylamino and 3-(tert-butoxycarbonyl)propylamino; |
| for carbamoyl-(1–6C)alkylamino: | carbamoylmethylamino and 2-carbamoylethylamino; |
| for N-(1–6C)alkylcarbamoyl-(1–6C)alkylamino: | N-methylcarbamoylmethylamino, N-ethylcarbamoylmethylamino and 2-(N-methylcarbamoyl)ethylamino; |
| for N,N-di-[(1–6C)alkyl]carbamoyl-(1–6C)alkylamino: | N,N-dimethylcarbamoylmethylamino, N,N-diethylcarbamoylmethylamino and 2-(N,N-dimethylcarbamoyl)ethylamino; |
| for amino-(2–6C)alkylamino: | 2-aminoethylamino and 3-aminopropylamino; |
| for (1–6C)alkylamino-(2–6C)alkylamino: | 2-methylaminoethylamino, 2-ethylaminoethylamino, 2-propylaminoethylamino, 3-methylaminopropylamino, 3-ethylaminopropylamino and 4-methylaminobutylamino; |
| for di-[(1–6C)alkyl]amino-(2–6C)alkylamino: | 2-dimethylaminoethylamino, 2-(N-ethyl-N-methylamino)ethylamino, 2-diethylaminoethylamino, 2-dipropylaminoethylamino, 3-dimethylaminopropylamino, 3-diethylaminopropylamino and 4-dimethylaminobutylamino; |
| for N-(1–6C)alkyl-halogeno-(2–6C)alkylamino: | N-(2-chloroethyl)-N-methylamino, N-(2-bromoethyl)-N-methylamino and N-(2-bromoethyl)-N-ethylamino; |
| for N-(1–6C)alkyl-hydroxy-(2–6C)alkylamino: | N-(2-hydroxyethyl)-N-methylamino, N-(3-hydroxypropyl)-N-methylamino and N-ethyl-N-(2-hydroxyethyl)amino; |
| for N-(1–6C)alkyl-(1–6C)alkoxy-(2–6C)alkylamino: | N-methyl-N-(2-methoxyethyl)amino, N-methyl-N-(3-methoxypropyl)amino and N-ethyl-N-(2-methoxyethyl)amino; |
| for N-(1–6C)alkyl-cyano-(1–6C)alkylamino: | N-(cyanomethyl)-N-methylamino; |
| for N-(1–6C)alkyl-carboxy-(1–6C)alkylamino: | N-carboxymethyl-N-methylamino and N-(2-carboxyethyl)-N-methylamino; |
| for N-(1–6C)alkyl-(1–6C)alkoxycarbonyl-(1–6C)alkylamino: | N-methoxycarbonylmethyl-N-methylamino, N-(2-ethoxycarbonylethyl)-N-ethylamino and N-(2-tert-butoxycarbonylethyl)-N-methylamino; |
| for N-(1–6C)alkyl-carbamoyl-(1–6C)alkylamino: | N-carbamoylmethyl-N-methylamino and N-(2-carbamoylethyl)-N-methylamino; |
| for N-(1–6C)alkyl-N-(1–6C)alkylcarbamoyl-(1–6C)alkylamino: | N-(N-methylcarbamoylmethyl)-N-methylamino, N-(N-ethylcarbamoylmethyl)-N-methylamino and N-[2-(N-methylcarbamoyl)ethyl]-N-methylamino; |
| for N-(1–6C)alkyl-N,N-di-[(1–6C)alkyl]carbamoyl-(1–6C)alkylamino: | N-(N,N-dimethylcarbamoylmethyl)-N-methylamino and N-[2-(N,N-dimethylcarbamoyl)ethyl]-N-methylamino; |
| for N-(1–6C)alkyl-amino-(2–6C)alkylamino: | N-(2-aminoethyl)-N-methylamino and N-(3-aminopropyl)-N-methylamino; |

-continued

| | |
|---|---|
| for N-(1–6C)alkyl-(1–6C)alkylamino-(2–6C)alkylamino: | N-(2-methylaminoethyl)-N-methylamino and N-(3-ethylaminopropyl)-N-ethylamino; |
| for N-(1–6C)alkyl-di-[(1–6C)alkyl]amino-(2–6C)alkylamino: | N-(2-dimethylaminoethyl)-N-methylamino, N-(2-diethyl-aminoethyl)-N-methylamino and N-(3-dimethylaminopropyl)-N-methylamino; |
| for (1–6C)alkanesulphonylamino: | methanesulphonylamino and ethanesulphonylamino; |
| for N-(1–6C)alkyl-(1–6C)alkanesulphonylamino: | N-methylmethanesulphonylamino and N-methylethanesulphonylamino; |
| for halogeno-(2–6C)alkanoylamino: | 2-chloroacetamido and 3-chloropropionamido; |
| for hydroxy-(2–6C)alkanoylamino: | 2-hydroxyacetamido and 3-hydroxypropionamido; |
| for (1–6C)alkoxy-(2–6C)alkanoylamino: | 2-methoxyacetamido and 3-methoxypropionamido; |
| for cyano-(2–6C)alkanoylamino: | 2-cyanoacetamido and 3-cyanopropionamido; |
| for carboxy-(2–6C)alkanoylamino: | 2-carboxyacetamido and 3-carboxypropionamido; |
| for (1–6C)alkoxycarbonyl-(2–6C)alkanoyl: | 2-methoxycarbonylacetamido, 2-(tert-butoxycarbonyl)acetamido and 3-methoxycarbonylpropionamido; |
| for carbamoyl-(2–6C)alkanoylamino: | 2-carbamoylacetamido, 3-carbamoylpropionamido and 4-carbamoylbutyramido; |
| for N-(1–6C)alkylcarbamoyl-(2–6C)alkanoylamino: | 2-(N-methylcarbamoyl)acetamido and 3-(N-ethylcarbamoyl)propionamido; |
| for N,N-di-[(1–6C)alkyl]carbamoyl-(2–6C)alkanoylamino: | 2-(N,N-dimethylcarbamoyl)acetamido, 2-(N,N-diethylcarbamoyl)acetamido and 3-(N,N-dimethylcarbamoyl)propionamido; |
| for amino-(2–6C)alkanoylamino: | 2-aminoacetamido, 2-aminopropionamido and 3-aminopropionamido; |
| for (1–6C)alkylamino-(2–6C)alkanoylamino: | 2-methylaminoacetamido, 2-ethylaminoacetamido, 2-methylaminopropionamido and 3-methylaminopropionamido; |
| for di-[(1–6C)alkyl]amino-(2–6C)alkanoylamino: | 2-dimethylaminoacetamido, 2-diethylaminoacetamido, 2-dimethylaminopropionamido and 3-dimethylaminopropionamido; |
| for aryl-(1–6C)alkylamino: | benzylamino and 2-phenethylamino; |
| for N-(1–6C)alkyl-aryl-(1–6C)alkylamino: | N-benzyl-N-methylamino; |
| for aroylamino: | benzamido and 2-naphthoylamino; |
| for aryl-(2–6C)alkanoylamino: | phenylacetamido and 3-phenylpropionamido; |
| for aryl-(1–6C)alkoxy-(1–6C)alkyl: | benzyloxymethyl and 2-benzyloxyethyl; |
| for aryl-(1–6C)alkylamino-(1–6C)alkyl: | benzylaminomethyl and 2-benzylaminoethyl; |
| for N-(1–6C)alkyl-aryl-(1–6C)alkylamino-(1–6C)alkyl: | N-benzyl-N-methylaminomethyl; |
| for heteroaryl-(1–6C)alkoxy: | heteroarylmethoxy and 2-heteroarylethoxy; |
| for heteroaryl-(1–6C)alkylamino: | heteroarylmethylamino and 2-heteroarylethylamino; |
| for N-(1–6C)alkyl-heteroaryl-(1–6C)alkylamino: | N-heteroarylmethyl-N-methylamino and N-(2-heteroarylethyl)-N-methylamino; |
| for heteroaryl-(2–6C)alkanoylamino: | 2-heteroarylacetamido and 3-heteroarylpropionamido; |
| for heteroaryl-(1–6C)alkoxy-(1–6C)alkyl: | heteroarylmethoxymethyl and 2-heteroarylethoxymethyl; |
| for heteroaryl-(1–6C)alkylamino-(1–6C)alkyl: | heteroarylmethylaminomethyl and 2-heteroarylethylaminomethyl; |
| for N-(1–6C)alkyl-heteroaryl-(1–6C)alkylamino-(1–6C)alkyl: | N-heteroarylmethyl-N-methylaminomethyl and N-(2-heteroarylethyl)-N-methylaminomethyl; |
| for heterocyclyl-(1–6C)alkoxy: | heterocyclylmethoxy, 2-heterocyclylethoxy, 3-heterocyclylpropoxy and 2-heterocyclyl-2-methylethoxy; |
| for heterocyclyl-(1–6C)alkylamino: | heterocyclylmethylamino, 2-heterocyclylethylamino and 3-heterocyclylpropylamino; |
| for N-(1–6C)alkyl-heterocyclyl-(1–6C)alkylamino: | N-heterocyclylmethyl-N-methylamino and N-(2-heterocyclylethyl)-N-methylamino; |
| for heterocyclyl-(2–6C)alkanoylamino: | 2-heterocyclylacetamido, 2-heterocyclylpropionamido and 3-heterocyclylpropionamido; |
| for heterocyclyl-(1–6C)alkoxy-(1–6C)alkyl: | heterocyclylmethoxymethyl and 2-heterocyclylethoxymethyl; |
| for heterocyclyl-(1–6C)alkylamino-(1–6C)alkyl: | heterocyclylmethylaminomethyl and 2-heterocyclylethylaminomethyl; |
| for N-(1–6C)alkyl-heterocyclyl-(1–6C)alkylamino-(1–6C)alkyl: | N-heterocyclylmethyl-N-methylaminomethyl and N-(2-heterocyclylethyl)-N-methylaminomethyl; |

When any of the substituents defined in paragraphs (B) or (D) hereinbefore which comprise a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino and di-[(1–6C)alkyl] amino, suitable substituents so formed include, for example, substituted heterocyclyl-(1–6C)alkoxy groups such as 2-hydroxy-3-piperidinopropoxy and 2-hydroxy-3-morpholinopropoxy, substituted (1–6C)alkylamino-(2–6C) alkoxy such as 2-hydroxy-3-methylaminopropoxy and substituted di-[(1–6C)alkyl]amino-(2–6C)alkoxy such as 3-dimethylamino-2-hydroxypropoxy, 3-[N-(3-dimethylaminopropyl-N-methylamino]propoxy and 3-[N-(3-dimethylaminopropyl)-N-methylamino]-2-hydroxypropoxy.

A suitable value for the aryl group when $R^1$ or the substituent on $R^4$ is aryloxy, arylamino, aryl-(1–6C) alkylamino, N-(1–6C)alkyl-aryl-(1–6C)alkylamino, aroylamino, arylsulphonylamino, N-arylsulphamoyl or aryl-(2–6C)alkanoylamino is phenyl or naphthyl, preferably phenyl.

A suitable value for the heteroaryl group when $R^1$ or the substituent on $R^4$ is, for example, heteroaryloxy or any of the other specified heteroaryl-containing groups is any of the suitable heteroaryl groups defined hereinbefore.

A suitable value for the heterocyclyl group when $R^1$ or the substituent on $R^4$ is, for example, heterocyclylamino or any of the other specified heterocyclyl-containing groups is any of the suitable heterocyclyl groups defined hereinbefore.

A suitable value for $R^4$ when it is cycloalkyl is, for example, a non-aromatic mono- or or bicyclic 5- to 10-membered carbon ring such as cyclopentyl, cyclohexyl, cycloheptyl, bicyclo[2.2.1]heptyl and bicyclo[4.4.0]decyl.

A suitable pharmaceutically-acceptable salt of a compound of the Formula I is, for example, an acid-addition salt of a compound of the Formula I which is sufficiently basic, for example an acid-addition salt with an inorganic or organic acid such as hydrochloric, hydrobromic, sulphuric, trifluoroacetic, citric or maleic acid; or, for example a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem. Pharm. Bull. 32, 692 (1984).

Examples of such pro-drugs may be used to form in-vivo-cleavable esters of a compound of the Formula I. An in-vivo-cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1–6C)alkoxymethyl esters, for example methoxymethyl; (1–6C)alkanoyloxymethyl esters, for example pivaloyloxymethyl; phthalidyl esters; (3–8C) cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; and (1–6C)alkoxycarbonyloxyethyl esters, for example 1-methoxycarbonyloxyethyl; and may be formed at any carboxy group in the compounds of this invention.

Particular novel compounds of the invention include, for example, amide derivatives of the Formula I, or pharmaceutically-acceptable salts thereof, wherein:

(a) $R^3$ is (1–6C)alkyl such as methyl, ethyl, propyl and isopropyl, preferably methyl and ethyl, more preferably methyl; and $R^1$, $R^2$, $R^4$, m, p and q have any of the meanings defined hereinbefore or in this section relating to particular novel compounds of the invention;

(b) $R^3$ is halogeno such as fluoro, bromo and chloro, preferably chloro and bromo, more preferably chloro; and $R^1$, $R^2$, $R^4$, m, p and q have any of the meanings defined hereinbefore or in this section relating to particular novel compounds of the invention;

(c) $R^1$ is selected from the substituents defined in paragraphs (A) and (B) hereinafter:

(A) hydroxy, halogeno, trifluoromethyl, cyano, (1–6C) alkyl, (1–6C)alkoxy and amino-(1–6C)alkyl; and (B) halogeno-(1–6C)alkyl, (1–6C)alkoxy-(1–6C)alkyl, (1–6C)alkylamino-(1–6C)alkyl, di-[(1–6C)alkyl] amino-(1–6C)alkyl, hydroxy-(2–6C)alkylamino-(1–6)alkyl, (1–6C)alkoxy-(2–6C)alkylamino-(1–6C) alkyl, halogeno-(2–6C)alkoxy, hydroxy-(2–6C) alkoxy, (1–6C)alkoxy-(2–6C)alkoxy, cyano-(1–6C) alkoxy, carboxy-(1–6C)alkoxy, (1–6C) alkoxycarbonyl-(1–6C)alkoxy, amino-(2–6C) alkoxy, (1–6C)alkylamino-(2–6C)alkoxy, di-[(1–6C) alkyl]amino-(2–6C)alkoxy, pyridyl-(1–6C)alkoxy, imidazolyl-(1–6C)alkoxy, piperidinyloxy, 1-(1–6C) alkylpiperidinyloxy, pyrrolidinyl-(2–6C)alkoxy, piperidinyl-(2–6C)alkoxy, morpholinyl-(2–6C) alkoxy, piperazinyl-(2–6C)alkoxy and 4-(1–6C) alkylpiperazinyl-(2–6C)alkoxy; and m is 1 or 2; and $R^2$, $R^3$, $R^4$, p and q have any of the meanings defined hereinbefore or in this section relating to particular novel compounds of the invention;

(d) q is 0, and $R^4$ is phenyl which is substituted with 1, 2 or 3 substituents selected from paragraphs (C) and (D) hereinafer:

(C) hydroxy, halogeno, trifluoromethyl, cyano, amino, (1–6C)alkyl, (1–6C)alkoxy, (1–6C)alkylamino, di-[(1–6C)alkyl]amino, phenyl, benzyl, benzyloxy, pyrrolidinyl, piperidinyl, morpholinyl, piperazinyl, 4-(1–6C)alkylpiperazinyl, pyrrolidinyl-(1–6C)alkyl, piperidinyl-(1–6C)alkyl, morpholinyl-(1–6C)alkyl, piperazinyl-(1–6C)alkyl and 4-(1–6C) alkylpiperazinyl-(1–6C)alkyl; and (D) halogeno-(1–6C)alkyl, (1–6C)alkoxy-(1–6C)alkyl, (1–6C)alkylamino-(1–6C)alkyl, di-[(1–6C)alkyl] amino-(1–6C)alkyl, hydroxy-(2–6C)alkylamino-(1–6C)alkyl, (1–6C)alkoxy-(2–6C)alkylamino-(1–6C)alkyl, halogeno-(2–6C)alkoxy, hydroxy-(2–6C)alkoxy, (1–6C)alkoxy-(2–6C)alkoxy, cyano-(2–6C)alkoxy, carboxy-(2–6C)alkoxy, (1–6C) alkoxycarbonyl-(1–6C)alkoxy, amino-(2–6C) alkoxy, (1–6C)alkylamino-(2–6C)alkoxy, di-[(1–6) alkyl]amino-(2–6C)alkoxy, halogeno-(2–6C) alkylamino, hydroxy-(2–6C)alkylamino, (1–6C) alkoxy-(2–6C)alkylamino, amino-(2–6C) alkylamino, (1–6C)alkylamino-(2–6C)alkylamino, di-[(1–6C)alkyl]amino-(2–6C)alkylamino, N-(1–6C)alkyl-halogeno-(2–6C)alkylamino, N-(1–6C)alkyl-hydroxy-(2–6C)alkylamino, N-(1–6C)alkyl-(1–6C)alkoxy-(2–6C)alkylamino, N-(1–6C)alkyl-amino-(2–6C)alkylamino, N-(1–6C) alkyl-(1–6C)alkylamino-(2–6C)alkylamino, N-(1–6C)alkyl-di-[(1–6C)alkyl]amino-(2–6C) alkylamino, pyridyl-(1–6C)alkoxy, imidazolyl-(1–6C)alkoxy, piperidinyloxy, 1-(1–6C) alkylpiperidinyloxy, pyrrolidinyl-(2–6C)alkoxy, piperidinyl-(2–6C)alkoxy, morpholinyl-(2–6C) alkoxy, piperazinyl-(2–6C)alkoxy and 4-(1–6C) alkylpiperazinyl-(2–6C)alkoxy;

provided that a substituent on $R^4$ is selected from paragraph (C) hereinbefore only if at least one $R^1$ group is selected from paragraph (B) within section (c) of this section relating to particular novel compounds of the invention; and $R^2$, $R^3$, m and p have any of the meanings defined hereinbefore or in this section relating to particular novel compounds of the invention;

(e) p is 0; and $R^1$, $R^3$, $R^4$, m and q have any of the meanings defined hereinbefore or in this section relating to particular novel compounds of the invention; and (f) q is 1, 2, 3 or 4, and $R^4$ is cycloalkyl; and $R^1$, $R^2$, $R^3$, m and p have any of the meanings defined hereinbefore or in this section relating to particular novel compounds of the invention.

A preferred compound of the invention is an amide derivative of the Formula I wherein $R^3$ is methyl, ethyl, chloro or bromo;

$R^1$ is selected from the substituents defined in paragraphs (A) and (B) hereinafter:

(A) hydroxy, fluoro, chloro, trifluoromethyl, cyano, methyl, ethyl, methoxy and ethoxy; and (B) chloromethyl, methoxymethyl, methylaminomethyl, ethylaminomethyl, dimethylaminomethyl, diethylaminomethyl, 2-hydroxyethylaminomethyl, 2-methoxyethylaminomethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, cyanomethoxy, carboxymethoxy, 2-carboxyethoxy, methoxycarbonylmethoxy, ethoxycarbonylmethoxy, tert-butoxycarbonylmethoxy, 2-methoxycarbonylethoxy, 2-ethoxycarbonylethoxy, 2-tert-butoxycarbonylethoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridylmethoxy, 2-(imidazol-1-yl)ethoxy, 3-(imidazol-1-yl)propoxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy and 3-(4-methylpiperazin-1-yl)propoxy;

m is 1 or 2;

p is 0;

q is 0; and $R^4$ is phenyl wherein $R^4$ is substituted with 1 or 2 substituents selected from paragraphs (C) and (D) hereinafter:

(C) hydroxy, fluoro, chloro, trifluoromethyl, cyano, methyl, ethyl, methoxy, ethoxy, methylamino, ethylamino, dimethylamino, diethylamino, phenyl, benzyl, benzyloxy, pyrrolidin-1-yl, piperidino, morpholino, piperazin-1-yl and 4-methylpiperazin-1-yl; and (D) chloromethyl, methoxymethyl, 2-methoxyethyl, methylaminomethyl, ethylaminomethyl, dimethylaminomethyl, diethylaminomethyl, 2-hydroxyethylaminomethyl, 2-methoxyethylaminomethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, cyanomethoxy, carboxymethoxy, 2-carboxyethoxy, methoxycarbonylmethoxy, ethoxycarbonylmethoxy, tert-butoxycarbonylmethoxy, 2-methoxycarbonylethoxy, 2-ethoxycarbonylethoxy, 2-tert-butoxycarbonylethoxy, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-chloroethylamino, 2-hydroxyethylamino, 2-methoxyethylamino, 2-ethoxyethylamino, 2-aminoethylamino, 2-methylaminoethylamino, 2-ethylaminoethylamino, 2-dimethylaminoethylamino, 2-diethylaminoethylamino, N-(2-chloroethyl)-N-methylamino, N-(2-hydroxyethyl)-N-methylamino, N-(2-methoxyethyl)-N-methylamino, N-(2-ethoxyethyl)-N-methylamino, N-(2-aminoethyl)-N-methylamino, N-(2-methylaminoethyl)-N-methylamino, N-(2-dimethylaminoethyl)-N-methylamino, N-(3-aminopropyl)-N-methylamino, N-(3-methylaminopropyl)-N-methylamino, N-(3-ethylaminopropyl)-N-methylamino, N-(3-dimethylaminopropyl)-N-methylamino, N-(3-diethylaminopropyl)-N-methylamino, 2-pyridylmethoxy, 2-(imidazol-1-yl)ethoxy, 3-(imidazol-1-yl)propoxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy and 3-(4-methylpiperazin-1-yl)propoxy; provided that a substituent on $R^4$ is selected from paragraph (C) immediately above only if at least one $R^1$ group is selected from paragraph (B) within the $R^1$ definition immediately above;

or a pharmaceutically-acceptable salt thereof.

A further preferred compound of the invention is an amide derivative of the Formula I wherein $R^3$ is methyl or chloro;

$R^1$ is selected from the substituents defined in paragraphs (A) and (B) hereinafter:

(A) methoxy; and (B) chloromethyl, dimethylaminomethyl, diethylaminomethyl, 2-methoxyethylaminomethyl, 2-methoxyethoxy, 2-ethoxyethoxy, 3-methoxypropoxy, 3-ethoxypropoxy, methoxycarbonylmethoxy, ethoxycarbonylmethoxy, tert-butoxycarbonylmethoxy, 2-pyridylmethoxy, 2-(imidazol-1-yl)ethoxy, 2-pyrrolidin-1-ylethoxy, 2-piperidinoethoxy, 3-piperidinopropoxy, 2-morpholinoethoxy and 3-morpholinopropoxy;

m is 1 or 2;

p is 0;

q is 0; and $R^4$ is phenyl wherein $R^4$ is substituted with 1 or 2 substituents selected from paragraphs (C) and (D) hereinafter:

(C) cyano and dimethylamino; and (D) chloromethyl, 2-chloroethoxy, 3-chloropropoxy, 2-hydroxyethoxy, 3-hydroxypropoxy, 2-methoxyethoxy, 2-ethoxyethoxy, 3-methoxypropoxy, 3-ethoxypropoxy, carboxymethoxy, methoxycarbonylmethoxy, ethoxycarbonylmethoxy, tert-butoxycarbonylmethoxy, 2-dimethylaminoethoxy, 2-diethylaminoethoxy, 3-dimethylaminopropoxy, 3-diethylaminopropoxy, N-(3-dimethylaminopropyl)-N-methylamino, 2-pyridylmethoxy, 2-pyrrolidin-1-ylethoxy, 3-pyrrolidin-1-ylpropoxy, 2-piperidinoethoxy, 3-piperidinopropoxy, 2-morpholinoethoxy and 3-morpholinopropoxy; provided that a substituent on $R^4$ is selected from paragraph (C) immediately above only if at least one $R^1$ group is selected from paragraph (B) within the $R^1$ definition immediately above;

or a pharmaceutically-acceptable salt thereof.

A more preferred compound of the invention is an amide derivative of the Formula I wherein $R^3$ is methyl or chloro;

p is 0;

q is 0;

m is 1 or 2;

R¹ is selected from the substituents defined in paragraphs (A) and (B) hereinafter:
  (A) methoxy; and
  (B) chloromethyl, diethylaminomethyl, 2-methoxyethylaminomethyl, 2-methoxyethoxy, 2-ethoxyethoxy, tert-butoxycarbonylmethoxy, methoxycarbonylmethoxy, 2-pyridylmethoxy, 2-(imidazol-1-yl)ethoxy, 2-pyrrolidin-1-ylethoxy, 2-morpholinoethoxy and 3-morpholinopropoxy; and R⁴ is phenyl which is substituted with one substituent selected from paragraphs (C) and (D) hereinafter:
  (C) cyano and dimethylamino; and
  (D) chloromethyl, 3-chloropropoxy, 3-hydroxypropoxy, N-(3-dimethylaminopropyl)-N-methylamino, 2-pyridylmethoxy and 2-morpholinoethoxy; provided that the substituent on R⁴ is selected from paragraph (C) immediately above only if at least R¹ group is selected from paragraph (B) within the R¹ definition immediately above;

or a pharmaceutically-acceptable salt thereof.

A further more preferred compound of the invention is an amide derivative of the Formula I wherein R³ is methyl or chloro;
  p is 0;
  q is 0;
  m is 1 or 2; and
  R¹ is methoxy and R⁴ is phenyl which is substituted with one 3-hydroxypropoxy substituent,
  or R¹ is 2-methoxyethoxy or 2-(imidazol-1-yl)ethoxy and R⁴ is phenyl which is substituted with one cyano or dimethylamino substituent;
or a pharmaceutically-acceptable salt thereof.

Particular preferred compounds of the invention include, for example:
  N-{5-[4-(3-hydroxypropoxy)benzamido]-2-methylphenyl}-3,4-dimethoxybenzamide,
  N-[5-(3-dimethylaminobenzamido)-2-methylphenyl]-4-(2-methoxyethoxy)benzamide,
  N-[5-(4-cyanobenzamido)-2-methylphenyl]-4-(2-methoxyethoxy)benzamide and
  N-[2-chloro-5-(4-cyanobenzamido)phenyl]-4-[2-(imidazol-1-yl)ethoxy]benzamide;
or the pharmaceutically-acceptable salts thereof.

In a further aspect of the present invention there is provided a group of novel compounds of the Formula I wherein (R¹)ₘ represents a basic substituent located at the 3- and/or 4-positions and R⁴ is phenyl which also bears a basic substituent located at the 3- and/or 4-positions. This group of compounds possesses improved TNFα inhibitory potency in one or both of the PBMC and Human Whole Blood tests described hereinafter.

A particular group of novel compounds according to this aspect of the invention is an amide derivative of the Formula I
  wherein m is 1, the R¹ group is selected from the substituents defined in paragraph (B) hereinafter and the R¹ group is located at the 3- or 4-position,
  or m is 2, at least one R¹ group is selected from the substituents defined in paragraph (B) hereinafter and one R¹ group may be selected from the substituents defined in paragraph (A) hereinafter and the R¹ groups, which may be the same or different, are located at the 3- and 4-positions:

(A) hydroxy, fluoro, chloro, trifluoromethyl, cyano, amino, methyl, ethyl, methoxy, ethoxy, methylamino, ethylamino, dimethylamino, diethylamino, aminomethyl, 2-aminoethyl, pyrrolidin-1-yl, piperidino, morpholino, piperazin-1-yl, 4-methylpiperazin-1-yl, pyrrolidin-1-ylmethyl, piperidinomethyl, morpholinomethyl, piperazin-1-ylmethyl and 4-methylpiperazin-1-ylmethyl; and (B) methylaminomethyl, ethylaminomethyl, dimethylaminomethyl, diethylaminomethyl, 2-hydroxyethylaminomethyl, 2-methoxyethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridylmethoxy, 2-(imidazol-1-yl)ethoxy, 3-(imidazol-1-yl)propoxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy and 3-(4-methylpiperazin-1-yl)propoxy;

p is 0;
R³ is methyl;
q is 0; and
R⁴ is phenyl which is substituted with 1 substituent selected from those defined in paragraph (D) hereinafter and located at the 3- or 4-position,
or R⁴ is phenyl which is substituted with 2 substituents, at least one selected from the substituents defined in paragraph (D) hereinafter and one optionally selected from the substituents defined in paragraph (C) hereinafter and the substituents, which may be the same or different, are located at the 3- and 4-positions:

(C) hydroxy, fluoro, chloro, trifluoromethyl, cyano, amino, methyl, ethyl, methoxy, ethoxy, methylamino, ethylamino, dimethylamino, diethylamino, aminomethyl, 2-aminoethyl, pyrrolidin-1-yl, piperidino, morpholino, piperazin-1-yl, 4-methylpiperazin-1-yl, pyrrolidin-1-ylmethyl, piperidinomethyl, morpholinomethyl, piperazin-1-ylmethyl and 4-methylpiperazin-1-ylmethyl; and (D) methylaminomethyl, ethylaminomethyl, dimethylaminomethyl, diethylaminomethyl, 2-hydroxyethylaminomethyl, 2-methoxyethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridylmethoxy, 2-(imidazol-1-yl)ethoxy, 3-(imidazol-1-yl)propoxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy and 3-(4-methylpiperazin-1-yl)propoxy;

or a pharmaceutically-acceptable salt thereof;
provided that a substituent on R⁴ is selected from paragraph (C) hereinbefore only if at least one R¹ group is selected from paragraph (B) hereinbefore.

A further particular group of novel compounds according to this aspect of the invention is an amide derivative of the Formula I
  wherein m is 1, the $R^1$ group is selected from the substituents defined in paragraph (B) hereinafter and the $R^1$ group is located at the 3- or 4-position,
  or m is 2 or 3, at least one $R^1$ group is selected from the substituents defined in paragraph (B) hereinafter and is located at the 3- or 4-position and the other $R^1$ groups, which may be the same or different, are selected from the substituents defined in paragraphs (A) or (B) hereinafter:
    (A) hydroxy, fluoro, chloro, trifluoromethyl, cyano, amino, methyl, ethyl, methoxy, ethoxy, methylamino, ethylamino, dimethylamino, diethylamino, aminomethyl, 2-aminoethyl, pyrrolidin-1-yl, piperidino, morpholino, piperazin-1-yl, 4-methylpiperazin-1-yl, pyrrolidin-1-ylmethyl, piperidinomethyl, morpholinomethyl, piperazin-1-ylmethyl and 4-methylpiperazin-1-ylmethyl; and
    (B) methylaminomethyl, ethylaminomethyl, dimethylaminomethyl, diethylaminomethyl, 2-hydroxyethylaminomethyl, 2-methoxyethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 2-diisopropylaminoethoxy, 3-dimethylaminopropoxy, 3-diethylaminopropoxy, 2-pyrrolidin-1-ylethoxy, 3-pyrrolidin-1-ylpropoxy, 2-(N-methylpyrrolidin-2-yl)ethoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-pyridylmethoxy, 2-methylthiazol4-ylmethoxy, 2-(imidazol-1-yl)ethoxy, 3-(imidazol-1-yl)propoxy, piperidin-4-yloxy, N-methylpiperidin-4-yloxy, N-methylhomopiperidin-4-yloxy, pyrrolidin-3-yloxy and N-methylpyrrolidin-3-yloxy;
  p is 0;
  $R^3$ is methyl;
  q is 0; and
  $R^4$ is phenyl which is substituted with 1, 2 or 3 substituents, which may be the same or different, selected from the substituents defined in paragraphs (C1), (C2) or (D) hereinafter provided that one substituent is selected from the substituents defined in paragraphs (C2) or (D) hereinafter and is located at the 3- or 4-position:
    (C1) hydroxy, fluoro, chloro, trifluoromethyl, cyano, methyl, ethyl, methoxy and ethoxy;
    (C2) amino, methylamino, ethylamino, dimethylamino, diethylamino, aminomethyl, 2-aminoethyl, pyrrolidin-1-yl, piperidino, morpholino, piperazin-1-yl, homopiperazin-1-yl, 4-methylpiperazin-1-yl, 4-methylhomopiperazin-1-yl, pyrrolidin-1-ylmethyl, piperidinomethyl, morpholinomethyl, piperazin-1-ylmethyl and 4-methylpiperazin-1-ylmethyl; and
    (D) methylaminomethyl, ethylaminomethyl, dimethylaminomethyl, diethylaminomethyl, 2-hydroxyethylaminomethyl, 2-methoxyethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy, 2-pyridylmethoxy, 2-(imidazol-1-yl)ethoxy, 3-(imidazol-1-yl)propoxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy and 3-(4-methylpiperazin-1-yl)propoxy;
  or a pharmaceutically-acceptable salt thereof.

A preferred group of novel compounds according to this aspect of the invention is an amide derivative of the Formula I
  wherein m is 1, the $R^1$ group is selected from the substituents defined in paragraph (B) hereinafter and the $R^1$ group is located at the 3- or 4-position,
  or m is 2, at least one $R^1$ group is selected from the substituents defined in paragraph (B) hereinafter and one $R^1$ group may be selected from the substituents defined in paragraph (A) hereinafter and the $R^1$ groups, which may be the same or different, are located at the 3- and 4-positions:
    (A) hydroxy, methyl, ethyl, methoxy, ethoxy, dimethylamino, diethylamino, pyrrolidin-1-yl, piperidino, morpholino, piperazin-1-yl, 4-methylpiperazin-1-yl, pyrrolidin-1-ylmethyl, piperidinomethyl, morpholinomethyl, piperazin-1-ylmethyl and 4-methylpiperazin-1-ylmethyl; and
    (B) dimethylaminomethyl, diethylaminomethyl, 2-dimethylaminoethoxy, 2-diethylaminoethoxy, 3-dimethylaminopropoxy, 3-diethylaminopropoxy, 2-pyridylmethoxy, piperidin-4-yloxy, 1-methylpiperidin-4-yloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy and 3-(4-methylpiperazin-1-yl)propoxy;
  p is 0;
  $R^3$ is methyl;
  q is 0; and
  $R^4$ is phenyl which is substituted at the 3-position with a substituent selected from dimethylamino, diethylamino, pyrrolidin-1-yl, piperidino, morpholino, piperazin-1-yl and 4-methylpiperazin-1-yl;
  or a pharmaceutically-acceptable salt thereof.

A further preferred group of novel compounds according to this aspect of the invention is an amide derivative of the Formula I
  wherein m is 1, the $R^1$ group is selected from the substituents defined in paragraph (B) hereinafter and the $R^1$ group is located at the 3- or 4-position,
  or m is 2, at least one $R^1$ group is selected from the substituents defined in paragraph (B) hereinafter and is located at the 3- or 4-position and the other $R^1$ group is selected from the substituents defined in paragraphs (A) or (B) hereinafter:
    (A) hydroxy, methyl, ethyl, methoxy, ethoxy, dimethylamino, diethylamino, pyrrolidin-1-yl, piperidino, morpholino, piperazin-1-yl, 4-methylpiperazin-1-yl, pyrrolidin-1-ylmethyl, piperidinomethyl, morpholinomethyl, piperazin-1-ylmethyl and 4-methylpiperazin-1-ylmethyl; and (B) dimethylaminomethyl, diethylaminomethyl, 2-dimethylaminoethoxy, 2-diethylaminoethoxy, 2-diisopropylaminoethoxy, 3-dimethylaminopropoxy, 3-diethylaminopropoxy, 2-(pyrrolidin-1-yl)ethoxy, 3-(pyrrolidin-1-yl) propoxy, 2-(N-methylpyrrolidin-2-yl)ethoxy, 2-piperidinoethoxy, 3-piperidinopropoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 2-pyridylmethoxy, 2-methylthiazol-4-ylmethoxy, piperidin-4-yloxy, N-methylpiperidin-4-yloxy, N-methylhomopiperidin-4-yloxy, pyrrolidin-3-yloxy and N-methylpyrrolidin-3-yloxy;

p is 0;

$R^3$ is methyl;

q is 0; and $R^4$ is phenyl which is substituted at the 3-position with a substituent selected from dimethylamino, diethylamino, pyrrolidin-1-yl, piperidino, morpholino, piperazin-1-yl, homopiperazin-1-yl, 4-methylpiperazin-1-yl and 4-methylhomopiperazin-1-yl and is optionally substituted with a further substituent selected from fluoro, chloro, cyano, methyl and trifluoromethyl;

or a pharmaceutically-acceptable salt thereof.

A further more preferred compound of this aspect of the invention is an amide derivative of the Formula I wherein $R^3$ is methyl;

p is 0;

q is 0;

$(R^1)_m$ is 4-diethylaminomethyl, 3-(2-diethylaminoethoxy), 3-(2-pyrrolidin-1-ylethoxy), 4-methoxy-3-(2-pyrrolidin-1-ylethoxy) or 3-(piperidin-4-yloxy); and $R^4$ is 3-morpholinophenyl;

or a pharmaceutically-acceptable salt thereof.

A further more preferred compound of this aspect of the invention is an amide derivative of the Formula I wherein $R^3$ is methyl;

p is 0;

q is 0;

$(R^1)_m$ is 4-diethylaminomethyl, 3-(2-diethylaminoethoxy), 3-(2-diisopropylaminoethoxy), 3-(3-diethylaminopropoxy), 3-(2-pyrrolidin-1-ylethoxy), 3-[2-(N-methylpyrrolidin-2-yl)ethoxy], 3-(2-piperidinoethoxy), 3-(3-piperidinopropoxy), 4-[3-(4-methylpiperazin-1-yl)propoxy], 4-methoxy-3-(2-pyrrolidin-1-ylethoxy), 4-methoxy-3-(2-piperidinoethoxy), 4-methoxy-3-(3-piperidinopropoxy), 4-methoxy-3-(2-diethylaminoethoxy), 4-methoxy-3-(3-diethylaminopropoxy), 4-methoxy-3-[2-(N-methylpyrrolidin-2-yl)ethoxy], 4-(2-pyridylmethoxy), 4-(2-methylthiazol-4-ylmethoxy), 3-piperidin-4-yloxy, 4-piperidin-4-yloxy, 3-(N-methylhomopiperidin4-yloxy) and 3-pyrrolidin-3-yloxy; and $R^4$ is 3-pyrrolidin-1-ylphenyl, 3-piperidinophenyl, 3-morpholinophenyl, 3-fluoro-5-morpholinophenyl or 3-morpholino-5-trifluoromethylphenyl;

or a pharmaceutically-acceptable salt thereof.

Further particular preferred compounds of this aspect of the invention include, for example:

N-[2-methyl-5-(3-morpholinobenzamido)phenyl]-3-piperidin-4-yloxybenzamide,

N-[2-methyl-5-(3-morpholinobenzamido)phenyl]-3-(2-pyrrolidin-1-ylethoxy)benzamide, N-[2-methyl-5-(3-morpholinobenzamido)phenyl]-3-(2-diethylaminoethoxy)benzamide, N-[2-methyl-5-(3-morpholinobenzamido)phenyl]-4-methoxy-3-(2-pyrrolidin-1-ylethoxy)benzamide and N-[2-methyl-5-(3-morpholinobenzamido)phenyl]-4-diethylaminomethylbenzamide;

or the pharmaceutically-acceptable salts thereof.

Further particular preferred compounds of this aspect of the invention include, for example:

N-[2-methyl-5-(3-morpholinobenzamido)phenyl]-4-[3-(4-methylpiperazin-1-yl)propoxy]benzamide, N-[2-methyl-5-(3-morpholinobenzamido)phenyl]-3-[2-(N-methylpyrrolidin-2-yl)ethoxy]benzamide, N-[2-methyl-5-(3-pyrrolidin-1-ylbenzamido)phenyl]-3-piperidin-4-yloxybenzamide, N-[2-methyl-5-(3-piperidinobenzamido)phenyl]-3-piperidin-4-yloxybenzamide, N-[2-methyl-5-(3-morpholinobenzamido)phenyl]-3-(N-methylhomopiperidin-4-yloxy)benzamide, N-[5-(3-fluoro-5-morpholinobenzamido)-2-methylphenyl]-3-piperidin-4-yloxybenzamide N-[2-methyl-5-(3-morpholinobenzamido)phenyl]-4-(2-pyridylmethoxy)benzamide, N-[5-(3-fluoro-5-morpholinobenzamido)-2-methylphenyl]-4-diethylaminomethylbenzamide and N-[5-(3-fluoro-5-pyrrolidin-1-ylbenzamido)-2-methylphenyl]-4-diethylaminomethylbenzamide;

or the pharmaceutically-acceptable salts thereof.

An amide derivative of the Formula I, or a pharmaceutically-acceptable salt or in-vivo-cleavable ester thereof, may be prepared by any process known to be applicable to the preparation of chemically-related compounds. Suitable processes are illustrated by, for example, those used in *J. Med. Chem,* 1996, 39, 3343–3356. Such processes, when used to prepare a novel amide derivative of the Formula I are provided as a further feature of the invention and are illustrated by the following representative process variants in which, unless otherwise stated, $R^1$, $R^2$, $R^3$, $R^4$, m, p and q have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) A compound of the Formula I, or a pharmaceutically-acceptable salt or in-vivo-cleavable ester thereof, may be prepared by reacting an aniline of the Formula II

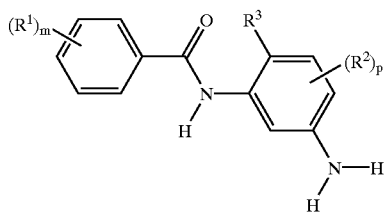

Formula II with an acid of the Formula III

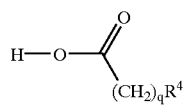

Formula III or an activated derivative thereof, under standard amide bond forming conditions, wherein variable groups are as hereinbefore defined and wherein any functional group is protected if necessary, and:

(i) removing any protecting groups;
(ii) optionally forming a pharmaceutically-acceptable salt or in-vivo-cleavable ester.

A suitable activated derivative of an acid of the Formula III is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester such as pentafluorophenyl trifluoroacetate or an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide.

The reaction is preferably carried out in the presence of a suitable base such as, for example, an alkali or alkaline earth metal carbonate, alkoxide, hydroxide or hydride, for example sodium carbonate, potassium carbonate, caesium carbonate, sodium ethoxide, potassium butoxide, sodium hydroxide, potassium hydroxide, sodium hydride or potassium hydride, or an organometallic base such as an alkyllithium, for example n-butyl-lithium, or a dialkylaminolithium, for example lithium di-isopropylamide, or, for example, an organic amine base such as, for example, pyridine, 2,6lutidine, collidine, 4-dimethylaminopyridine, triethylamine, morpholine or diazabicyclo[5.4.0]undec-7-ene. The reaction is also preferably carried out in a suitable inert solvent or diluent, for example tetrahydrofuran, 1,2-dimethoxyethane, N,N-dimethylformamide, N,N-dimethylacetamide, N-methylpyrrolidin-2-one, dimethylsulphoxide or acetone, and at a temperature in the range, for example, −78° to 150° C., conveniently at or near ambient temperature.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, tert-butyl); lower alkoxy lower alkyl groups (for example methoxymethyl, ethoxymethyl, isobutoxymethyl); lower aliphatic acyloxy lower alkyl groups, (for example acetoxymethyl, propionyloxymethyl, butyryloxymethyl, pivaloyloxymethyl); lower alkoxycarbonyloxy lower alkyl groups (for example 1-methoxycarbonyloxyethyl, 1-ethoxycarbonyloxyethyl); aryl lower alkyl groups (for example benzyl, p-methoxybenzyl, o-nitrobenzyl, p-nitrobenzyl, benzhydryl and phthalidyl); tri(lower alkyl) silyl groups (for example trimethylsilyl and tert-butyldimethylsilyl); tri(lower alkyl)silyl lower alkyl groups (for example trimethylsilylethyl); and (2–6C)alkenyl groups (for example allyl and vinylethyl). Methods particularly appropriate for the removal of carboxyl protecting groups include for example acid-, base-, metal- or enzymically-catalysed hydrolysis.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl lower alkoxycarbonyl groups (for example benzoyloxycarbonyl, p-methoxybenzyloxycarbonyl, o-nitrobenzyloxycarbonyl, p-nitrobenzyloxycarbonyl); tri lower alkylsilyl (for example trimethylsilyl, tert-butyldimethylsilyl) and aryl lower alkyl (for example benzyl) groups.

Examples of amino protecting groups include formyl, aralkyl groups (for example benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (for example tert-butoxycarbonyl); lower alkenyloxycarbonyl (for example allyloxycarbonyl); aryl lower alkoxycarbonyl groups (for example benzyloxycarbonyl, p-methoxybenzyloxycarbonyl, o-nitrobenzyloxycarbonyl, p-nitrobenzyloxycarbonyl; tri-alkylsilyl (for example trimethylsilyl and tert-butyldimethylsilyl); alkylidene (for example methylidene); benzylidene and substituted benzylidene groups.

Methods appropriate for removal of hydroxy and amino protecting groups include, for example, acid-, base-, metal- or enzymically-catalysed hydrolysis for groups such as p-nitrobenzyloxycarbonyl, hydrogenation for groups such as benzyl and photolytically for groups such as o-nitrobenzyloxycarbonyl.

The reader is referred to Advanced Organic Chemistry, 4th Edition, by Jerry March, published by John Wiley & Sons 1992, for general guidance on reaction conditions and reagents. The reader is referred to Protective Groups in Organic Synthesis, 2nd Edition, by Green et al., published by John Wiley & Sons for general guidance on protecting groups.

The aniline of Formula II may be prepared by reduction of the corresponding nitro compound of Formula IV.

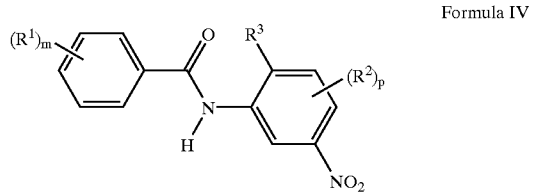

Formula IV

Typical reaction conditions include the use of ammonium formate in the presence of a catalyst (for example palladium-on-carbon) in the presence of an organic solvent (preferably a polar protic solvent), preferably with heating, for example to about 60° C. Any functional groups are protected and deprotected as necessary.

The compound of Formula IV may be prepared by reaction of an acid of Formula V, or an activated derivative thereof,

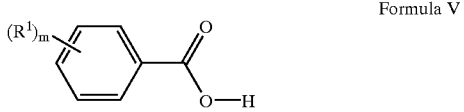

Formula V with an aniline of Formula VI under suitable amide bond forming conditions.

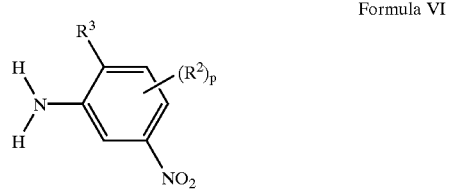

Formula VI

Typical conditions include activating the carboxy group of the compound of Formula V for example by treatment with a halo reagent (for example oxalyl chloride) to form an acyl halide in an organic solvent at ambient temperature, then reacting the activated compound with the aniline of Formula VI. Any functional groups are protected and deprotected as necessary.

(b) A compound of the Formula I, or a pharmaceutically-acceptable salt or in-vivo-cleavable ester thereof, may be prepared by reacting an acid of the Formula V

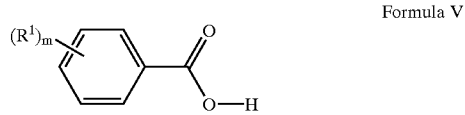

Formula V or an activated derivative thereof as defined hereinbefore, with an aniline of the Formula VII

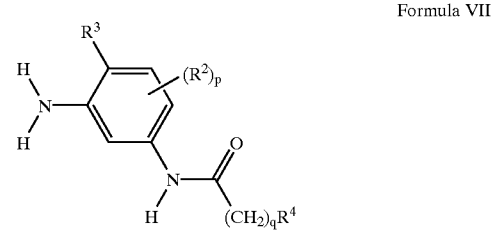

Formula VII under standard amide bond forming conditions, wherein variable groups are as hereinbefore defined and wherein any functional group is protected, if necessary, and:
(i) removing any protecting groups;
(ii) optionally forming a pharmaceutically-acceptable salt or in-vivo-cleavable ester.

The aniline of Formula VII may be prepared by reduction of the corresponding nitro compound using convention procedures as defined hereinbefore or as illustrated in the Examples.

(c) A compound of the Formula I wherein $R^1$ or a substituent on $R^4$ is (1–6C)alkoxy or substituted (1–6C) alkoxy, (1–6C)alkylthio, (1–6C)alkylamino, di-[(1–6C) alkyl]amino or substituted (1–6C)alkylamino or heterocyclyloxy, may be prepared by the alkylation, conveniently in the presence of a suitable base as defined hereinbefore, of an amide derivative of the Formula I wherein $R^1$ or a substituent on $R^4$ is hydroxy, mercapto or amino as appropriate.

The reaction is preferably carried out in the presence of a suitable inert solvent or diluent, for example a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 80° C.

A suitable alkylating agent is, for example, any agent known in the art for the alkylation of hydroxy to alkoxy or substituted alkoxy, or for the alkylation of mercapto to alkylthio, or for the alkylation of amino to alkylamino or substituted alkylamino, or for the alkylation of hydroxy to heterocyclyloxy, for example an alkyl or substituted alkyl halide or a heterocyclyl halide, for example a (1–6C)alkyl chloride, bromide or iodide or a substituted (1–6C)alkyl chloride, bromide or iodide or a heterocyclyl chloride, bromide or iodide, in the presence of a suitable base as defined hereinbefore.

(d) A compound of the Formula I wherein $R^1$ or a substituent on $R^4$ is (1–6C)alkanoylamino or substituted (2–6C)alkanoylamino may be prepared by the acylation of a compound of the Formula I wherein $R^1$ or a substituent on $R^4$ is amino.

A suitable acylating agent is, for example, any agent known in the art for the acylation of amino to acylamino, for example an acyl halide, for example a (1–6C)alkanoyl chloride or bromide, conveniently in the presence of a suitable base, as defined hereinbefore, an alkanoic acid anhydride or mixed anhydride, for example a (1–6C) alkanoic acid anhydride such as acetic anhydride or the mixed anhydride formed by the reaction of an alkanoic acid and a (1–6C)alkoxycarbonyl halide, for example a (1–6C) alkoxycarbonyl chloride, in the presence of a suitable base as defined hereinbefore. In general the acylation is carried out in a suitable inert solvent or diluent as defined hereinbefore and at a temperature, in the range, for example, −30 to 120° C., conveniently at or near ambient temperature.

(e) A compound of the Formula I wherein $R^1$ or a substituent on $R^4$ is (1–6C)alkanesulphonylamino may be prepared by the reaction of a compound of the Formula I wherein $R^1$ or a substituent on $R^4$ is amino with a (1–6C) alkanesulphonic acid, or an activated derivative thereof.

A suitable activated derivative of a (1–6C) alkanesulphonic acid is, for example, an alkanesulphonyl halide, for example an alkanesulphonyl chloride formed by the reaction of the sulphonic acid and an inorganic acid chloride, for example thionyl chloride. The reaction is preferably carried out in the presence of a suitable base as defined hereinbefore, particularly pyridine, and in a suitable inert solvent or diluent as defined hereinbefore, particularly methylene chloride.

(f) A compound of the Formula I wherein $R^1$ or a substituent on $R^4$ is carboxy, carboxy-(1–6C)alkyl, carboxy-(1–6C)alkoxy, carboxy-(1–6C)alkylamino, N-(1–6C)alkyl-carboxy-(1–6C)alkylamino or carboxy-(2–6C) alkanoylamino may be prepared by the cleavage of a compound of the Formula I wherein $R^1$ or a substituent on $R^4$ is (1–6C)alkoxycarbonyl, (1–6C)alkoxycarbonyl-(1–6C) alkyl, (1–6C)alkoxycarbonyl-(1–6C)alkoxy, (1–6C) alkoxycarbonyl-(1–6C)alkylamino, N-(1–6C)alkyl-(1–6C) alkoxycarbonyl-(1–6C)alkylamino or (1–6C) alkoxycarbonyl-(2–6C)alkanoylamino as appropriate.

The cleavage reaction may conveniently be carried out by any of the many procedures known in the art for such a transformation. The reaction may be carried out, for example, by hydrolysis under acidic or basic conditions. A suitable base is, for example, an alkali metal, alkaline earth metal or ammonium carbonate or hydroxide, for example sodium carbonate, potassium carbonate, sodium hydroxide, potassium hydroxide or ammonium hydroxide. The reaction is preferably carried out in the presence of water and a suitable solvent or diluent such as methanol or ethanol. The reaction is conveniently carried out at a temperature in the range 10 to 150° C., preferably at or near ambient temperature.

(g) A compound of the Formula I wherein $R^1$ or a substituent on $R^4$ is amino-(1–6C)alkyl, heterocyclyl-(1–6C)alkyl, (1–6C)alkylamino-(1–6C)alkyl, di-[(1–6C) alkyl]amino-(1–6C)alkyl, substituted (2–6C)alkylamino-(1–6C)alkyl or substituted N-(1–6C)alkyl-(2–6C) alkylamino-(1–6C)alkyl may be prepared by the reaction of a compound of the Formula I wherein $R^1$ or a substituent on $R^4$ is a group of the formula -(1–6C)alkylene-Z wherein Z is a displaceable group with an appropriate amine or heterocyclyl compound.

A suitable displaceable group Z is, for example, a halogeno group such as fluoro, chloro or bromo, a (1–6C) alkanesulphonyloxy group such as methanesulphonyloxy or an arylsulphonyloxy group such as 4-toluenesulphonyloxy.

The reaction is conveniently carried out in the presence of a suitable base as defined hereinbefore and in the presence of a suitable inert diluent or carrier as defined hereinbefore. The reaction is conveniently carried out at a temperature in the range 10 to 150° C., preferably at or near 50° C.

(h) A compound of the Formula I wherein $R^1$ or a substituent on $R^4$ is amino, heterocyclyl, (1–6C)alkylamino, di-[(1–6C)alkyl]amino, substituted (1–6C)alkylamino, substituted N-(1–6C)alkyl-(1–6C)alkylamino, substituted (2–6C)alkylamino or substituted N-(1–6C)alkyl-(2–6C) alkylamino may be prepared by the reaction of a compound of the Formula I wherein $R^1$ or a substituent on $R^4$ is a displaceable group Z as defined hereinbefore with an appropriate amine or heterocyclyl compound.

The reaction is conveniently carried out in the presence of a suitable base as defined hereinbefore and in the presence of a suitable inert diluent or carrier as defined hereinbefore. The reaction is conveniently carried out at a temperature in the range 25 to 250° C., preferably at or near 150° C.

(i) A compound of the Formula I wherein $R^1$ or a substituent on $R^4$ is N-(1–6C)alkyl-(1–6C) alkanesulphonylamino may be prepared by the alkylation, conveniently in the presence of a suitable base as defined hereinbefore, of an amide derivative of the Formula I wherein $R^1$ or a substituent on $R^4$ is (1–6C) alkanesulphonylamino.

The reaction is conveniently carried out in the presence of a suitable inert diluent or carrier as defined hereinbefore and at a temperature in the range 10 to 150° C., preferably at or near ambient temperature.

(j) A compound of the Formula I wherein $R^1$ or a substituent on $R^4$ is a hydroxy-heterocyclyl-(1–6C)alkoxy group (such as 2-hydroxy-3-piperidinopropoxy), a hydroxy-(1–6C)alkylamino-(2–6C)alkoxy group (such as 2-hydroxy-3-methylaminopropoxy) or a hydroxy-di-[(1–6C)alkyl] amino-(2–6C)alkoxy group (such as 3-dimethylamino-2-hydroxypropoxy or 3-[N-(3-dimethylaminopropyl)-N-methylamino]-2-hydroxypropoxy) may be prepared by the reaction of a compound of the Formula I wherein $R^1$ or a substituent on $R^4$ is a epoxy-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(k) A compound of the Formula I wherein $R^1$, $R^2$ or a substituent on $R^4$ is an amino group may be prepared by the reduction of a compound of the Formula I wherein $R^1$, $R^2$ or a substituent on $R^4$ is a nitro group.

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

The following biological assays and Examples serve to illustrate the present invention.

Biological Assays

The following assays can be used to measure the p38 kinase-inhibitory, the TNF-inhibitory and anti-arthritic effects of the compounds of the present invention:

In vitro Enzyme Assay

The ability of compounds of the invention to inhibit the enzyme p38 kinase was assessed. Activity of test compounds against each of the p38α and p38β isoforms of the enzyme was determined.

Human recombinant MKK6 (GenBank Accesion Number G1209672) was isolated from Image clone 45578 (*Genomics,* 1996, 33, 151) and utilised to produce protein in the form of a GST fusion protein in a pGEX vector using analogous procedures to those disclosed by J. Han et al., *Journal of Biological Chemistry,* 1996, 271, 2886–2891. p38α (GenBank Accession Number G529039) and p38β (GenBank Accession Number G1469305) were isolated by PCR amplification of human lymphoblastoid cDNA (GenBank Accession Number GM1416) and human foetal brain cDNA [synthesised from mRNA (Clontech, catalogue no. 6525-1) using a Gibco superscript cDNA synthesis kit] respectively using oligonucleotides designed for the 5' and 3' ends of the human p38α and p38β genes using analogous procedures to those described by J. Han et al., *Biochimica et Biophysica Acta,* 1995, 1265, 224–227 and Y. Jiang et al., *Journal of Biological Chemistry,* 1996, 271, 17920–17926.

Both p38 protein isoforms were expressed in *e coli* in PET vectors. Human recombinant p38α and p38β isoforms were produced as 5' c-myc, 6His tagged proteins. Both MKK6 and the p38 proteins were purified using standard protocols: the GST MKK6 was purified using a glutathione sepharose column and the p38 proteins were purified using nickel chelate columns.

The p38 enzymes were activated prior to use by incubation with MKK6 for 3 hours at 30° C. The unactivated coli-expressed MKK6 retained sufficient activity to fully activate both isoforms of p38. The activation incubate comprised p38α (10 μl of 10 mg/ml) or p38β (10 μl of 5 mg/ml) together with MKK6 (10 μl of 1 mg/ml), 'Kinase buffer' [100 μl; pH 7.4 buffer comprising Tris (50 mM), EGTA (0.1 mM), sodium orthovanadate (0.1 mM) and β-mercaptoethanol (0.1%)] and MgATP (30 μl of 50 mM Mg(OCOCH$_3$)$_2$ and 0.5 mM ATP). This produced enough activated p38 enzyme for 3 Microtiter plates.

Test compounds were solubilised in DMSO and 10 μl of a 1:10 diluted sample in 'Kinase Buffer' was added to a well in a Microtiter plate. For single dose testing, the compounds were tested at 10 μM. 'Kinase Assay Mix' [30 μl; comprising Myelin Basic Protein (Gibco BRL cat. no. 1322B-010; 1 ml of a 3.33 mg/ml solution in water), activated p38 enzyme (50 μl) and 'Kinase Buffer' (2 ml)] was then added followed by 'Labelled ATP' [10 μl; comprising 50 μM ATP, 0.1 μCi $^{33}$P ATP (Amersham International cat. no. BF1000) and 50 mM Mg(OCOCH$_3$)$_2$]. The plates were incubated at room temperature with gentle agitation. Plates containing p38α were incubated for 90 min and plates containing p38β were incubated for 45 min. Incubation was stopped by the addition of 50 μl of 20% trichloroacetic acid (TCA). The precipitated protein was phosphorylated by p38 kinase and test compounds were assessed for their ability to inhibit this phosphorylation. The plates were filtered using a Canberra Packard Unifilter and washed with 2% TCA, dried overnight and counted on a Top Count scintillation counter.

Test compounds were tested initially at a single dose and active compounds were retested to allow IC$_{50}$ values to be determined.

In Vitro Cell-based Assays
(i) PBMC

The ability of compounds of this invention to inhibit TNFα production was assessed by using human peripheral blood mononuclear cells which synthesise and secrete TNFα when stimulated with lipopolysaccharide.

Peripheral blood mononuclear cells (PBMC) were isolated from heparinised (10 units/ml heparin) human blood by density centrifugation (Lymphoprep™; Nycomed). Mononuclear cells were resuspended in culture medium [RPMI 1640 medium (Gibco) supplemented with 50 units/ml penicillin, 50 μg/ml streptomycin, 2 mM glutamine and 1% heat-inactivated human AB serum (Sigma H-1513)]. Compounds were solubilised in DMSO at a concentration of 50 mM, diluted 1:100 in culture medium and subsequently serial dilutions were made in culture medium containing 1% DMSO. PBMCs (2.4×10$^5$ cells in 160 μl culture medium) were incubated with 20 μl of varying concentrations of test compound (triplicate cultures) or 20 μl culture medium containing 1% DMSO (control wells) for 30 minutes at 37° C. in a humidified (5%CO$_2$/95% air) incubator (Falcon 3072; 96 well flat-bottom tissue culture plates). 20 μl lipopolysaccharide [LPS *E.Coli* 0111:B4 (Sigma L-4130), final concentration 10 μg/ml] solubilised in culture medium was added to appropriate wells. 20 μl culture medium was added to "medium alone" control wells. Six "LPS alone" and four "medium alone" controls were included on each 96 well plate. Varying concentrations of a known TNFα inhibitor were included in each test, i.e. an inhibitor of the PDE Type IV enzyme (for example see Semmler, J. Wachtel. H and Endres, S., *Int. J. Immunopharmac.* (1993), 15(3), 409–413) or an inhibitor of proTNFα convertase (for example, see McGeehan, G. M. et al. *Nature* (1994) 370, 558–561). Plates were incubated for 7 hours at 37° C. (humidified incubator) after which 100 μl of the supernatant was removed from each well and stored at −70° C. (96 well round-bottom plates; Corning 25850). TNFα levels were determined in each sample using a human TNFα ELISA (see WO92/10190 and *Current Protocols in Molecular Biology,* vol 2 by Frederick M. Ausbel et al., John Wiley and Sons Inc.).

$$\% \text{ inhibition} = \frac{(LPS \text{ alone} - \text{medium alone}) - (\text{test concentration} - \text{medium alone})}{(LPS \text{ alone} - \text{medium alone})} \times 100$$

(ii) Human Whole Blood

The ability of the compounds of this invention to inhibit TNFα production was also assessed in a human whole blood assay. Human whole blood secretes TNFα when stimulated with LPS. This property of blood forms the basis of an assay which is used as a secondary test for compounds which profile as active in the PBMC test.

Heparinised (10 units/ml) human blood was obtained from volunteers. 160 μl whole blood were added to 96 well round-bottom plates (Corning 25850). Compounds were solubilised and serially diluted in RPMI 1640 medium (Gibco) supplemented with 50 units/ml penicillin, 50 μg/ml streptomycin and 2 mM glutamine, as detailed above. 20 μl of each test concentration was added to appropriate wells (triplicate cultures). 20 μl of RPMI 1640 medium supplemented with antibiotics and glutamine was added to control wells. Plates were incubated for 30 minutes at 37° C. (humidified incubator), prior to addition of 20 μl LPS (final concentration 10 μg/ml). RPMI 1640 medium was added to control wells. Six "LPS alone" and four "medium alone" controls were included on each plate. A known TNFα synthesis/secretion inhibitor was included in each test. Plates were incubated for 6 hours at 37° C. (humidified incubator). Plates were centrifuged (2000 rpm for 10 minutes) and 100 μl plasma removed and stored at −70° C. (Corning 25850 plates). TNFα levels were measured by ELISA (see WO92/10190 and *Current Protocols in Molecular Biology,* vol 2 by Frederick M. Ausbel et al., John Wiley and Sons Inc.). The paired antibodies that were used in the ELIZA were obtained from R&D Systems (catalogue nos. MAB610 anti-human TNFα coating antibody, BAF210 biotinylated anti-human TNFα detect antibody).

Ex Vivo/In Vivo Assessment

The ability of the compounds of this invention as ex vivo TNFα inhibitors were assessed in the rat or mouse. Briefly, groups of male Wistar Alderley Park (AP) rats (180–210 g) were dosed with compound (6 rats) or drug vehicle (10 rats) by the appropriate route, for example peroral (p.o.), intraperitoneal (i.p.) or subcutaneous (s.c.). Ninety minutes later rats were sacrificed using a rising concentration of $CO_2$ and bled out via the posterior vena cavae into 5 Units of sodium heparin/ml blood. Blood samples were immediately placed on ice and centrifuged at 2000 rpm for 10 min at 4° C. and the harvested plasmas frozen at −20° C. for subsequent assay of their effect on TNFα production by LPS-stimulated human blood. The rat plasma samples were thawed and 175 µl of each sample was added to a set format pattern in a 96 well round bottom plate (Corning 25850). 50 µl of heparinized human blood was then added to each well, mixed and the plate was incubated for 30 min at 37° C. (humidified incubator). LPS (25 µl; final concentration 10 µpg/ml) was added to the wells and incubation continued for a further 5.5 hours. Control wells were incubated with 25 µl of medium alone. Plates were then centrifuged for 10 min at 2000 rpm and 200 µl of the supernatants were transferred to a 96 well plate and frozen at −20° C. for subsequent analysis of TNF concentration by ELISA.

Data analysis by dedicated software calculates for each compound/dose:

$$\% \text{ inhibition of } TNF\alpha = \frac{\text{Mean } TNF\alpha \text{ (Controls)} - \text{Mean } TNF\alpha \text{ (Treated)}}{\text{Mean } TNF\alpha \text{ (Controls)}} \times 100$$

Alternatively, mice could be used instead of rats in the above procedure.

Test as Anti-arthritic Agent

Activity of a compound as an anti-arthritic agent was tested as follows. Acid soluble native type II collagen was shown by Trentham et al. [1] to be arthritogenic in rats; it caused polyarthritis when administered in Freunds incomplete adjuvant. This is now known as collagen-induced arthritis (CIA) and similar conditions can be induced in mice and primates. Recent studies have shown that anti-TNF monoclonal antibodies [2] and TNF receptor-IgG fusion proteins [3] ameliorate established CIA indicating that TNF plays a key role in the pathophysiology of CIA. Moreover, the remarkable efficacy reported for anti-TNF monoclonal antibodies in recent rheumatoid arthritis clinical trials indicates that TNF plays a major role in this chronic inflammatory disease. Thus CIA in DBA/1 mice as described in references 2 and 3 is a tertiary model which can be used to demonstrate the anti-arthritic activity of a compound. Also see reference 4.

1. Trentham, D. E. et al., (1977) *J. Exp. Med.,* 146, 857.
2. Williams, R. O. et al., (1992) *Proc. Natl. Acad. Sci.,* 89, 9784.
3. Williams, R. O. et al., (1995) *Immunology,* 84, 433.
4. Badger, M. B. et al., (1996) *The Journal of Pharmacology and Experimental Therapeutics,* 279, 1453–1461.

Although the pharmacological properties of the compounds of the Formula I vary with structural change as expected, in general a compound of the Formula I gives over 30% inhibition in the PBMC test at concentrations up to 50 µM. No physiologically unacceptable toxicity was observed at the effective dose for compounds tested of the present invention. By way of example:

N-[5-(4-cyanobenzamido)-2-methylphenyl]-4-(2-methoxyethoxy)benzamide [Example 8] has an $IC_{50}$ of approximately 0.1 µM against p38α and an $IC_{50}$ of approximately 3 µM in the PBMC test; and N-[2-methyl-5-(3-morpholinobenzamido)phenyl]-3-(2-pyrrolidin-1-ylethoxy)benzamide [Example 7, Compound No. 19] has an $IC_{50}$ of approximately 0.1 µM against p38α, an $IC_{50}$ of approximately 1 µM in the PBMC test and an $IC_{50}$ of approximately 6 µM in the Human Whole Blood test.

According to a further aspect of the invention there is provided a pharmaceutical composition which comprises an amide derivative of the Formula I, or a pharmaceutically-acceptable salt or in-vivo-cleavable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. Typically, unit dosage forms will contain about 1 mg to 500 mg of a compound of this invention.

According to a further aspect of the invention there is provided an amide derivative of the Formula I, or a pharmaceutically-acceptable salt or in-vivo-cleavable ester thereof, as defined hereinbefore for use in a method of treatment of the human or animal body by therapy.

According to a further aspect of the invention there is provided the use of an amide derivative of the Formula I, or a pharmaceutically-acceptable salt or in-vivo-cleavable ester thereof, as defined hereinbefore in the manufacture of a medicament for use in the treatment of medical conditions mediated by cytokines.

In a further aspect the present invention provides a method of treating diseases or medical conditions mediated by cytokines which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by TNF, IL-1, IL-6 or IL-8.

In a further aspect the present invention provides a method of treating diseases or medical conditions mediated by TNF, IL-1, IL-6 or IL-8 which comprises administering to a warm-blooded animal an effective amount of a compound of the Formula I or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof in the manufacture of a medicament for use in the treatment of diseases or medical conditions mediated by TNF.

In a further aspect the present invention provides a method of treating diseases or medical conditions mediated by TNF which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF, IL-1, IL-6 or IL-8.

In a further aspect the present invention provides a method of inhibiting TNF, IL-1, IL6 or IL-8 which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in inhibiting TNF.

In a further aspect the present invention provides a method of inhibiting TNF which comprises administering to a warm-blooded animal an effective amount of a compound of the Formula I, or a pharmaceutically-acceptable salt or in vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of diseases or medical conditions mediated by p38 kinase.

In a further aspect the present invention provides a method of treating diseases or medical conditions mediated by p38 kinase which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the production of a p38 kinase inhibitory effect.

In a further aspect the present invention provides a method of providing a p38 kinase inhibitory effect which comprises administering to a warm-blooded animal an effective amount of a compound of the Formula I, or a pharmaceutically-acceptable salt or in-vivo-cleavable ester thereof.

In a further aspect the present invention provides the use of a compound of the Formula I, or a pharmaceutically-acceptable salt or in-vivo-cleavable ester thereof, in the manufacture of a medicament for use in the treatment of rheumatoid arthritis, asthma, irritable bowel disease, multiple sclerosis, AIDS, septic shock, congestive heart failure, ischaemic heart disease or psoriasis.

In a further aspect the present invention provides a method of treating rheumatoid arthritis, asthma, irritable bowel disease, multiple sclerosis, AIDS, septic shock, congestive heart failure, ischaemic heart disease or psoriasis which comprises administering to a warm-blooded animal an effective amount of a compound of the Formula I, or a pharmaceutically-acceptable salt or in-vivo-cleavable ester thereof.

The compounds of this invention may be used in combination with other drugs and therapies used in the treatment of disease states which would benefit from the inhibition of cytokines, in particular TNF and IL-1. For example, the compounds of the Formula I could be used in combination with drugs and therapies used in the treatment of rheumatoid arthritis, asthma, irritable bowel disease, multiple sclerosis, AIDS, septic shock, congestive heart failure, ischaemic heart disease, psoriasis and the other disease states mentioned earlier in this specification.

For example, by virtue of their ability to inhibit cytokines, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt or in-vivo-cleavable ester thereof in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of cytokines. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM250 spectrometer operating at a field strength of 250 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:

| DMA | N,N-dimethylacetamide |
| DMF | N,N-dimethylformamide |
| DMSO | dimethylsulphoxide |
| THF | tetrahydrofuran |

EXAMPLE 1

N-[5-(3-methanesulphonylaminobenzamido)-2-methylphenyl]-3,4-dimethoxybenzamide

Methanesulphonyl chloride (0.25 g) was added to a stirred mixture of N-[5-(3-aminobenzamido)-2-methylphenyl]-3,4-dimethoxybenzamide (0.84 g), pyridine (0.5 ml) and methylene chloride (25 ml) and the mixture was stirred at ambient temperature for 48 hours. The mixture was washed with 2N hydrochloric acid and with water, dried (MgSO$_4$) and evaporated. The residue was triturated under diethyl ether and the resultant white solid was dried under vacuum at 60° C. There was thus obtained the title compound (0.85 g), m.p.>300° C.; NMR Spectrum: (DMSOd$_6$) 2.18 (s, 3H), 3.03 (s, 3H), 3.82 (s, 6H), 7.06 (d, 1H), 7.23 (d, 1H), 7.4 (br d, 1H), 7.47 (t, 1H), 7.55 (br m, 2H), 7.63 (m, 1H), 7.66 (br d, 1H), 7.72 (d, 1H), 7.78 (d, 1H), 9.73 (br s, 1H), 9.91 (br s, 1H), 10.24 (br s, 1H); Mass Spectrum: M–H$^-$ 482.

The N-[5-(3-aminobenzamido)-2-methylphenyl]-3,4-dimethoxybenzamide used as starting material was prepared as follows:

A solution of 3,4dimethoxybenzoyl chloride (11.5 g) in methylene chloride (100 ml) was added dropwise to a stirred mixture of 2-methyl-5-nitroaniline (8.74 g), pyridine (18.6 ml) and methylene chloride (200 ml) and the mixture was stirred at ambient temperature for 18 hours. The mixture was washed with 2N hydrochloric acid and with water, dried (MgSO$_4$) and evaporated. The resultant solid was dried under vacuum at 60° C. There was thus obtained N-(2-methyl-5-nitrophenyl)-3,4-methoxybenzamide (15.9 g), m.p.>300° C.; NMR Spectrum: (CDCl$_3$) 2.43 (s, 3H), 3.94 (m, 6H), 6.93 (m, 1H), 7.38 (m, 2H), 7.51 (m, 1H), 7.75 (br s, 1H), 7.94 (d, 1H), 8.89 (br m, 1H).

10% Palladium-on-carbon (4 g) was added to a stirred suspension of the material so obtained in methanol (1500 ml) and the mixture was stirred under an atmosphere of hydrogen gas. After cessation of hydrogen uptake, the catalyst was removed by filtration and the filtrate was evaporated. The residue was washed with diethyl ether and dried under vacuum at 60° C. There was thus obtained N-(5-amino-2-methylphenyl)-3,4-dimethoxybenzamide (11.3 g), m.p. 157–158° C.; NMR Spectrum: (CDCl$_3$) 2.24 (s, 3H), 3.64 (br s, 2H), 3.95 (m, 6H), 6.44 (m, 1H), 6.93 (d, 1H), 6.98 (d, 1H), 7.38 (m, 1H), 7.54 (m, 2H), 7.6 (br s, 1H).

The material so obtained was reacted with 3-nitrobenzoyl chloride using an analogous procedure to that described in the first paragraph of the portion of this Example which is concerned with the preparation of starting materials. There was thus obtained N-[2-methyl-5-(3-nitrobenzamido) phenyl]-3,4-dimethoxybenzamide, m.p. 232–233° C.; NMR Spectrum: (CDCl$_3$) 2.19 (s, 3H), 3.83 (s, 6H), 7.07 (d, 1H), 7.24 (d, 1H), 7.61 (m, 3H), 7.83 (t, 2H), 8.45 (m, 2H), 8.79 (d, 1H), 9.76 (s, 1H), 10.55 (br s, 1H).

10% Palladium-on-carbon (0.13 g) was added to a stirred suspension of the material so obtained (1.27 g) in methanol (150 ml) and the mixture was stirred under an atmosphere of hydrogen gas. After cessation of hydrogen uptake the catalyst was removed by filtration and the filtrate was evaporated. The residue was washed with diethyl ether (50 ml) and dried under vacuum at 60° C. There was thus obtained N-[5-(3-aminobenzamido)-2-methylphenyl]-3,4-dimethoxybenzamide (1.02 g), m.p. 179–180° C.; NMR Spectrum: (DMSOd$_6$) 2.15 (s, 3H), 3.82 (s, 6H), 5.25 (s, 2H), 6.72 (d, 1H), 7.05 (br m, 31H), 7.1 (t, 1H), 7.19 (d, 1H), 7.52 (m, 1H), 7.55 (d, 1H), 7.63 (m, 1H), 7.79 (d, 1H), 9.76 (br s, 1H), 10.02 (br s, 1H).

EXAMPLE 2

N-[5-(4-chloromethylbenzamido)-2-methylphenyl]-3,4-dimethoxybenzamide 4-(Chloromethyl)benzoyl chloride (0.73 g) was added dropwise to a stirred mixture of N-(5-amino-2- methylphenyl)-3,4-dimethoxybenzamide (1 g), triethylamine (0.98 ml) and methylene chloride (80 ml) and the mixture was stirred at ambient temperature for 16 hours. A 1N hydrochloric acid solution (10 ml) was added and the resultant solution was stirred at ambient temperature for 1 hour. The resultant white solid was filtered off, washed with water and with diethyl ether, dried under vacuum at 40° C. to give the title compound (1.35 g); NMR Spectrum: (DMSOd$_6$) 2.18 (s, 3H), 3.82 (s, 6H), 4.82 (s, 2H), 7.06 (d, 1H), 7.21 (d, 1H), 7.58 (m, 5H), 7.81 (s, 1H), 7.94 (d, 2H), 9.76 (s, 1H), 10.23 (s, 1H); Mass Spectrum: M+H$^+$ 439.

EXAMPLE 3

N-{5-[4-(3-chloropropoxy)benzamido]-2-methylphenyl}-3,4-dimethoxybenzamide

Oxalyl chloride (2.13 g) was added to a stirred mixture of 4-(3-chloropropoxy)benzoic acid (3 g), DMF (3 drops) and methylene chloride (150 ml) and the mixture was stirred at ambient temperature for 3 hours. The solvent was evaporated. The residue was dissolved in methylene chloride (80 ml) and added dropwise to a stirred mixture of N-(5-amino-2-methylphenyl)-3,4-dimethoxybenzamide (3.33 g), pyridine (3.77 ml) and methylene chloride (120 ml). The resultant mixture was stirred at ambient temperature for 18 hours. The mixture was washed in turn with 2N hydrochloric acid, water, a saturated aqueous sodium bicarbonate solution and water. The organic phase was dried (MgSO$_4$) and evaporated. The residue was triturated under diethyl ether and the resultant white solid was dried under vacuum at 60° C. to give the title compound (5.05 g), m.p. 186–187° C.; NMR Spectrum: (DMSOd$_6$) 2.18 (m, 5H), 3.8 (t, 2H), 3.83 (s, 6H), 4.17 (t, 2H), 7.07 (m, 3H), 7.21 (d, 1H), 7.55 (m, 1H), 7.63 (m, 1H), 7.8 (d, 1H); 7.95 (d, 2H), 9.74 (br s, 1H), 10.05 (br s, 1H); Mass Spectrum: M+H$^+$ 483.

EXAMPLE 4

N-{5-[4-(2-pyrrolidin-1-ylethoxy)benzamido]-2-methylphenyl}-3,4-dimethoxybenzamide N-(2-Chloroethyl)pyrrolidine hydrochloride (0.13 g) was added to a stirred mixture of N-[5-(4-hydroxybenzamido)-2-methylphenyl]-3,4-dimethoxybenzamide (0.25 g), potassium carbonate (0.26 g) and DMA (5 ml) and the resultant mixture was stirred and heated to 60° C. for 1 week. The mixture was allowed to cool to ambient temperature and poured into water (125 ml). The resultant precipitate was isolated, washed with water and with diethyl ether and dried under vacuum at 60° C. There was thus obtained the title compound (0.208 g), m.p. 165–166° C.; NMR Spectrum: (DMSOd$_6$) 1.17 (m, 4H), 2.17 (s, 3H), 2.49 (br m, 4H), 2.79 (t, 2H), 3.83 (s, 6H), 4.13 (t, 2H), 7.05 (t, 3H), 7.2 (d, 1H), 7.55 (m, 2H), 7.625 (m, 1H), 7.81 (d, 1H); 7.94 (d, 2H), 9.74 (br s, 1H), 10.03 (br s, 1H); Mass Spectrum: (M–H)$^-$ 502.

The N-[5-(4-hydroxybenzamido)-2-methylphenyl]-3,4-dimethoxybenzamide used as starting material was prepared as follows:

N-(5-Amino-2-methylphenyl)-3,4-dimethoxybenzamide was reacted with 4-benzyloxybenzoyl chloride using an analogous procedure to that described in the first paragraph of the portion of Example 1 which is concerned with the preparation of starting materials. There was thus obtained N-[5-(4-benzyloxybenzamido)-2-methylphenyl]-3,4-dimethoxybenzamide, m.p. 186–187° C.; NMR Spectrum: (CDCl$_3$) 2.17 (s, 3H), 3.83 (s, 6H), 5.18 (s, 2H), 7.07 (d, 1H), 7.13 (d, 2H), 7.2 (d, 1H), 7.37 (m, 3H), 7.45 (m, 2H), 7.55 (m, 2H), 7.63 (m, 1H), 7.8 (d, 1H), 7.94 (d, 2H), 9.74 (br s, 1H), 10.04 (br s, 1H).

10% Palladium-on-carbon (0.5 g) was added to a stirred suspension of N-[5-(4-benzyloxybenzamido)-2-methylphenyl]-3,4-dimethoxybenzamide (3.97 g) in methanol (500 ml) and the mixture was stirred under an atmosphere of hydrogen gas. After cessation of hydrogen uptake, the catalyst was removed by filtration and the filtrate was evaporated. The residue was washed with diethyl ether and dried under vacuum at 60° C. There was thus obtained the required starting material (2.93 g), m.p. 258–259° C.; NMR Spectrum: (DMSOd$_6$) 2.17 (s, 3H), 3.83 (s, 6H), 6.84 (d, 2H), 7.05 (d, 1H), 7.19 (d, 1H), 7.54 (m, 2H), 7.65 (d, 1H), 7.78 (d, 1H), 7.84 (d, 2H), 9.74 (br s, 1H), 9.93 (br s, 1H).

EXAMPLE 5

Using an analogous procedure to that described in Example 4, the appropriate phenol was reacted with the appropriate alkyl halide to give the compounds described in Table 1.

TABLE I

| No. | (R$^1$)$_m$ | R | Note |
| --- | --- | --- | --- |
| 1 | 3,4-dimethoxy | 4-(2-diethylaminoethoxy) | a |
| 2 | 3,4-dimethoxy | 3-(2-morpholinoethoxy) | b |
| 3 | 3,4-dimethoxy | 4-(3-morpholinopropoxy) | c |
| 4 | 3,4-dimethoxy | 4-tert-butoxycarbonylmethoxy | d |
| 5 | 3,4-dimethoxy | 3-tert-butoxycarbonylmethoxy | e |
| 6 | 3,4-dimethoxy | 3-(3-morpholinopropoxy) | f |
| 7 | 3,4-dimethoxy | 2-tert-butoxycarbonylmethoxy | g |
| 8 | 3,4-dimethoxy | 2-(2-pyridylmethoxy) | h |
| 9 | 3,4-dimethoxy | 3-(2-pyridylmethoxy) | i |
| 10 | 3,4-dimethoxy | 2,3-di-(2-pyridylmethoxy) | j |

Notes a) The product gave the following data: NMR (DMSOd$_6$) 0.96 (t, 6H), 2.18 (s, 3H), 2.53 (m, 4H), 2.76 (t, 2H), 3.83 (s, 6H), 4.08 (t, 2H), 7.04 (m, 3H), 7.2 (d, 1H), 7.55 (m, 2H), 7.63 (m, 1H), 7.79 (d, 1H), 7.94 (d, 2H), 9.74 (br s,1H), 10.03 (br s, 1H); Mass M+H 506.

b) The product gave the following data: NMR (DMSOd$_6$) 2.18 (s, 3H), 2.47 (t, 4H), 2.7 (t, 2H), 3.56 (t, 4H), 3.82 (s, 6H), 4.15 (t, 2H), 7.06 (d, 1H), 7.13 (m, 1H), 7.22 (d, 1H), 7.42 (t, 1H), 7.51 (d, 1H), 7.56 (br m, 3H), 7.63 (m, 1H), 7.8 (d, 1H), 9.75 (br s, 1H), 10.15 (br s, 1H); Mass M+H 520.

The N-[5-(3-hydroxybenzamido)-2-methylphenyl]-3,4-dimethoxybenzamide which was used as a starting material was prepared as follows. N-(5-Amino-2-methylphenyl)-3,4-dimethoxybenzamide was reacted with 3-benzyloxybenzoyl chloride using an analogous procedure to that described in the first paragraph of the portion of Example 1 which is concerned with the preparation of starting materials. There was thus obtained N-[5-(3-benzyloxybenzamido)-2-methylphenyl]-3,4-dimethoxybenzamide, m.p. 208–209° C.; NMR: (CDCl$_3$) 2.21 (s, 3H), 3.83 (s, 6H), 5.18 (s, 2H), 7.06 (d, 1H), 7.21 (m, 2H), 7.4 (m, 5H), 7.55 (m, 3H), 7.62 (m, 1H), 7.8 (d, 1H), 9.77 (brs, 1H), 10.17 (br s, 1H).

The benzyloxy group was cleaved by hydrogenolysis using an analogous procedure to that described in the last paragraph of the portion of Example 4 which is concerned with the preparation of starting materials. There was thus obtained the required starting material, m.p. 182–183° C.;

NMR: (CDCl$_3$) 2.17 (s, 3H), 3.83 (s, 6H), 6.95 (m, 1H), 7.06 (d, 1H), 7.22 (d, 1H), 7.32 (m, 2H), 7.36 (d, 1H), 7.55 (m, 2H), 7.63 (m, 1H), 7.82 (d, 1H), 9.68 (br s, 2H), 9.75 (br s, 1H), 10.13 (br s, 1H).

c) The standard procedure was adapted to the following:

Morpholine (0.27 g) and sodium iodide (0.33 g) were added in turn to a stirred solution of N-[5-(4-(3-chloropropoxy)benzamido)-2-methylphenyl]-3,4-dimethoxybenzamide (0.5 g) in acetone (15 ml) and the mixture was stirred and heated to reflux for 1 week. The mixture was evaporated and the residue was partitioned between methylene chloride and water. The organic phase was washed with water, dried (MgSO$_4$) and evaporated. The residual solid was triturated under diethyl ether and the resultant solid was dried under vacuum at 60° C. There was thus obtained N-{2-methyl-5-[4-(3-morpholinopropoxy)benzamido]phenyl}-3,4-dimethoxybenzamide (0.47 g), m.p. 148–149° C.; NMR (DMSOd$_6$) 1.87 (m, 2H), 2.17 (s, 3H), 2.38 (br m, 6H), 3.55 (br m, 4H), 3.82 (s, 6H), 4.07 (t, 2H), 7.06 (m, 3H), 7.2 (d, 1H), 7.55 (d, 2H), 7.63 (m, 1H), 7.8 (d, 1H), 7.94 (d, 2H), 9.76 (br s, 1H), 10.04 (br s, 1H); Mass M+H 534.

d) The phenol was reacted with tert-butyl bromoacetate. The product gave the following data: m.p. 193–194° C.; NMR (DMSOd$_6$) 1.43 (s, 9H), 2.18 (s, 3H), 3.83 (s, 6H), 4.74 (s, 2H), 7.01 (d, 2H), 7.06 (d, 1H), 7.21 (d, 1H), 7.55 (m, 2H), 7.62 (m, 1H), 7.8 (d, 1H), 7.93 (d, 2H), 9.75 (br s, 1H), 10.06 (br s, 1H); Mass M+H 521.

e) The phenol was reacted with tert-butyl bromoacetate. The product gave the following data: m.p. 182–183° C.; NMR (DMSOd$_6$) 1.43 (s, 9H), 2.18 (s, 3H), 3.83 (s, 6H), 4.75 (s, 2H), 7.06 (d, 2H), 7.12 (m, 1H), 7.23 (d, 1H), 7.42 (t, 1H), 7.44 (br s, 1H), 7.58 (br m, 1H), 7.63 (m, 1H), 7.8 (d, 1H), 9.77 (br s, 1H), 10.17 (br s, 1H); Mass M+H 521.

f) The reactants were heated to 90° C. for 18 hours. The product gave the following data: NMR (DMSOd$_6$) 2.18 (s, 3H), 2.23 (m, 2H), 3.04 (m, 2H), 3.24 (m, 2H), 3.44 (m, 2H), 3.82 (m, 8H), 3.92 (m, 2H), 4.15 (t, 2H), 7.06 (d, 1H), 7.14 (m, 1H), 7.22 (m, 1H), 7.43 (t, 1H), 7.56 (m, 5H); 7.83 (d, 2H), 9.79 (br s, 1H), 10.3 (br s, 1H); Mass M+H 534.

g) The phenol was reacted with tert-butyl bromoacetate. The product gave the following data: m.p. 156–157° C.; NMR (DMSOd$_6$) 1.43 (s, 1H), 2.18 (s, 3H), 3.83 (s, 6H), 4.89 (s, 2H), 7.06 (d, 1H), 7.13 (m, 2H), 7.24 (d, 1H), 7.49 (t, 1H), 7.3 (m, 2H), 7.47 (m, 2H), 7.57 (m, 2H), 7.63 (m, 1H), 7.89 (d, 2H), 9.76 (br s, 1H), 10.39 (br s, 1H); Mass M+H 521.

The N-[5-(2-hydroxybenzamido)-2-methylphenyl]-3,4-dimethoxybenzamide which was used as a starting material was prepared as follows:

Oxalyl chloride (1.34 g) was added to a stirred mixture of 2-benzyloxybenzoic acid (2 g), DMF (3 drops) and methylene chloride (60 ml) and the resultant solution was stirred at ambient temperature for 3 hours. The solvent was evaporated and the residue was dissolved in methylene chloride (15 ml) and added dropwise to a stirred mixture of N-(5-amino-2-methylphenyl)-3,4-dimethoxybenzamide (2.09 g), pyridine (2.36 ml) and methylene chloride (45 ml). The mixture was stirred at ambient temperature for 72 hours. The resultant precipitate was isolated, washed in turn with methylene chloride and diethyl ether and dried under vacuum at 60° C. There was thus obtained N-[5-(2-benzyloxybenzamido)-2-methylphenyl]-3,4-dimethoxybenzamide (2.62 g), m.p. 215–216° C.; NMR (DMSOd$_6$) 2.13 (s, 3H), 3.83 (s, 6H), 5.24 (s, 2H), 7.11 (m, 3H), 7.26 (m, 3H), 7.52 (m, 4H), 7.63 (m, 2H), 7.71 (m, 1H), 7.86 (t, 2H), 9.73 (br s, 1H), 10.13 (d, 1H); Mass: M+H 497.

10% Palladium-on-carbon (0.5 g) was added to a stirred mixture of the material so obtained (2.44 g) and methanol (300 ml) and the resultant mixture was stirred under one atmosphere pressure of hydrogen. After cessation of hydrogen uptake, the catalyst was removed by filtration and the filtrate was evaporated. The resultant solid was dried under vacuum at 60° C. There was thus obtained the required starting material (1.85 g). NMR: (DMSOd$_6$) 2.19 (s, 3H), 3.82 (s, 6H), 6.94 (m, 2H), 7.06 (d, 1H), 7.24 (d, 1H), 7.42 (t, 1H), 7.47 (m, 1H), 7.53 (d, 1H), 7.62 (m, 2H), 7.76 (d, 1H), 7.96 (m, 1H), 9.75 (br s, 1H), 10.35 (br s, 1H), 11.83 (br s, 1H); Mass: M–H 405.

h) The phenol was reacted with 2-chloromethylpyridine, the reactants being heated to 60° C. for 18 hours. The product gave the following data: NMR (DMSOd$_6$) 2.18 (s, 3H), 3.83 (s, 6H), 5.4 (s, 2H), 7.08 (d, 1H), 7.1 (m, 1H), 7.23 (d, 1H), 7.43 (t, 1H), 7.3 (m, 2H), 7.47 (m, 2H), 7.58 (m, 2H), 7.64 (m, 1H), 7.75 (d, 1H), 7.81 (m, 2H), 8.6 (d, 1H), 9.78 (br s, 1H), 10.56 (br s, 1H); Mass M+H 498.

i) The phenol was reacted with 2-chloromethylpyridine, the reactants being heated to 70° C. for 18 hours. The product gave the following data: m.p. 185–186° C.; NMR (DMSOd$_6$) 2.18 (s, 3H), 3.82 (s, 6H), 5.25 (s, 2H), 7.05 (d, 1H), 7.23 (m, 2H), 7.34 (m, 1H), 7.43 (t, 1H), 7.52 (m, 4H), 7.62 (m, 2H), 7.8 (br s, 1H), 7.84 (m, 1H), 8.57 (d, 1H), 9.73 (br s, 1H), 10.17 (br s, 1H); Mass M+H 498.

j) The product gave the following data: NMR (DMSOd$_6$) 2.15 (s, 3H), 3.83 (s. 6H), 5.28 (s, 4H), 7.07 (d, 1H), 7.49 (m, 14H), 7.55 (m. 2H), 8.4 (d, 1H), 8.58 (d, 1H), 9.75 (br s, 1H), 10.55 (br s, 1H); Mass M+H 605.

The N-[5-(2,3-dihydroxybenzamido)-2-methylphenyl]-3,4-dimethoxybenzamide which was used as a starting material was prepared as follows:

N-(5-Amino-2-methylphenyl)-3,4-dimethoxybenzamide was reacted with 2,3-dibenzyloxybenzoyl chloride using an analogous procedure to that described in the first paragraph of the portion of Example 1 which is concerned with the preparation of starting materials. There was thus obtained N-[5-(2,3-dibenzyloxybenzamido)-2-methylphenyl]-3,4-dimethoxybenzamide, m.p. 166–167° C.; NMR: (DMSOd$_6$) 2.16 (s, 3H), 3.82 (s, 6H), 5.1 (s, 2H), 5.23 (s, 2H), 7.05 (d, 1H), 7.17 (m, 3H), 7.36 (m, 7H), 7.52 (d, 2H), 7.56 (d, 1H), 7.63 (m, 1H), 7.69 (d, 1H), 9.75 (br s, 1H), 10.46 (br s, 1H).

10% palladium-on-carbon (0.5 g) was added to a solution of the material so obtained (2.6 g) in methanol (300 ml) and the mixture was stirred under an atmosphere of hydrogen. After cessation of hydrogen uptake, the catalyst was removed by filtration and the filtrate was evaporated. The residue was triturated under diethyl ether. The resultant solid was isolated and dried under vacuum at 60° C. There was thus obtained the required starting material (1.68 g), m.p. 210–211° C.; NMR: (DMSOd$_6$) 2.19 (s, 3H), 3.84 (s, 6H), 6.33 (t, 1H), 6.75 (d, 1H), 6.95 (d, 1H), 7.06 (d, 1H), 7.25 (d, 1H), 7.47 (m, 2H), 7.58 (d, 1H), 7.64 (m, 1H), 9.77 (br s, 1H), 10.38 (br s, 1H).

EXAMPLE 6

N-[5-(3-dimethylaminobenzamido)-2-methylphenyl] 4-(3-morpholinopropoxy)benzamide 4-(3-Chloropropyl)morpholine (0.1 g) was added to a stirred mixture of N-[5-(3-dimethylaminobenzamido)-2-methylphenyl]4-hydroxybenzamide (0.195 g), potassium carbonate (0.21 g) and DMA (5 ml). The mixture was then heated to 60° C. for 36 hours. The mixture was poured into water (150 ml) and the resultant solid was collected, washed with water and with diethyl ether. The product was dried under vacuum. There was thus obtained the title compound (0.203 g) as a colourless solid; NMR Spectrum: (DMSOd$_6$) 1.88 (m, 2H), 2.18 (s, 3H), 2.36 (t, 4H), 2.41 (t, 2H), 2.96 (s, 6H), 3.58 (t, 4H), 4.08 (d, 2H), 6.9 (m, 1H), 7.01 (d, 2H), 7.19 (m, 3H), 7.26 (t, 1H), 7.58 (d, 1H), 7.78 (s, 1H), 7.98 (d, 2H), 9.72 (s, 1H), 10.08 (s, 1H); Mass Spectrum: M+H+517.

The N-[5-(3dimethylaminobenzamido)-2-methylphenyl]-4-hydroxybenzamide used as starting material was prepared as follows:

Oxalyl chloride (0.5 ml) was added slowly to a stirred mixture of 4-acetoxybenzoic acid (1.09 g), methylene chloride (30 ml) and DMF (one drop) and the mixture was stirred at ambient temperature for 2 hours. A solution of 2-methyl-5-nitroaniline (0.76 g) and pyridine (2 ml) in methylene chloride was added over 15 minutes and the mixture was stirred for a further 2 hours. The reaction mixture washed with a 5% aqueous acetic acid solution, with water and with a 5% aqueous sodium bicarbonate solution. The organic extract was dried (MgSO$_4$) and evaporated. The residue was recrystallised from ethyl acetate to give N-(2-methyl-5-nitrophenyl)-4-acetoxybenzamide (0.8 g), m.p. 207–208° C.; NMR Spectrum: (DMSOd$_6$) 2.3 (s, 3H), 7.31 (d, 2H), 7.56 (d, 1H), 8.02 (m, 3H), 8.47 (d, 1H), 10.12 (s, 1H).

A mixture of a portion (0.5 g) of the material so obtained, ammonium formate (1 g), 10% palladium-on-carbon (0.25 g) and methanol (10 ml) was stirred and heated to 60° C. for 2 hours. The reaction mixture was cooled and filtered and the filtrate was evaporated. The residue was triturated under water. The crude product was filtered from the aqueous solution and crystallised from methanol to give N-(5-amino-2-methylphenyl)-4-hydroxybenzamide (0.14 g), m.p. 277–278° C.; NMR Spectrum: (DMSOd$_6$) 2.03 (s, 3H), 4.85 (s, 2H), 6.39 (m, 1H), 6.61(d, 1H), 6.85 (m, 3H), 7.82 (d, 2H), 9.3 (s, 1H), 9.96 (s, 1H).

4-Dimethylaminopyridine (0.13 g) was added to a mixture a portion (0.085 g) of the material so obtained, 3-dimethylaminobenzoic acid (0.089 g), 1-(3-dimethylaminopropyl)-3-ethylcarbodiimide hydrochloride (0.103 g), methylene chloride (3 ml) and DMF (0.5 ml). The reaction mixture was stirred at ambient temperature for 18 hours. The mixture was evaporated and the residue was purified by column chromatography on silica eluting in turn with 50%, 60% and 70% ethyl acetate in isohexane. There was thus obtained N-[5-(3-dimethylaminobenzamido)-2-methylphenyl]-4-hydroxybenzamide (0.017 g); NMR Spectrum: (DMSOd$_6$) 2.17 (s, 3H), 2.96 (s, 6H), 6.80–6.95 (m, 3H), 7.15–7.35 (m, 4H), 7.58 (m, 1H), 7.79 (d, 1H), 7.87 (d, 2H), 9.62 (s, 1H), 9.95 (s, 1H), 10.1 (s, 1H).

EXAMPLE 7

Using an analogous procedure to that described in Example 6, the appropriate phenol was reacted with the appropriate alkyl chloride to give the compounds described in Table II.

TABLE II

| No. | (R$^1$)$_m$ | R | Note |
|---|---|---|---|
| 1 | 3-methoxy-4-(3-morpholinopropoxy) | 3-dimethylamino | a |
| 2 | 3-[2-(pyrrolidin-1-yl)ethoxy] | 3-dimethylamino | b |
| 3 | 3-(2-morpholinoethoxy) | 3-dimethylamino | c |
| 4 | 4-(2-morpholinoethoxy) | 3-dimethylamino | d |
| 5 | 3-(3-morpholinopropoxy) | 3-dimethylamino | e |
| 6 | 3-methoxy-4-(2-morpholinoethoxy) | 3-dimethylamino | f |
| 7 | 4-methoxy-3-(2-piperidinoethoxy) | 3-dimethylamino | g |
| 8 | 4-methoxy-3-[2-(pyrrolidin-1-yl)ethoxy] | 3-dimethylamino | h |
| 9 | 4-methoxy-3-(3-morpholinopropoxy) | 3-dimethylamino | i |
| 10 | 4-methoxy-3-(2-morpholinoethoxy) | 3-dimethylamino | j |
| 11 | 4-(2-pyridylmethoxy) | 3-dimethylamino | k |
| 12 | 3-(2-pyridylmethoxy) | 3-dimethylamino | l |
| 13 | 4-(2-methoxyethoxy) | 3-dimethylamino | m |
| 14 | 2-[2-(pyrrolidin-1-yl)ethoxy] | 3-dimethylamino | n |
| 15 | 4-[2-(pyrrolidin-1-yl)ethoxy] | 3-dimethylamino | o |
| 16 | 3-methoxy-4-[2-(pyrrolidin-1-yl)ethoxy] | 3-dimethylamino | p |
| 17 | 3-methoxy-4-(2-pyridylmethoxy) | 3-dimethylamino | q |
| 18 | 3-methoxy-4-(tert-butoxycarbonylmethoxy) | 3-dimethylamino | r |
| 19 | 3-[2-(pyrrolidin-1-yl)ethoxy] | 3-morpholino | s |
| 20 | 3-(2-piperidinoethoxy) | 3-morpholino | t |
| 21 | 3-(2-morpholinoethoxy) | 3-morpholino | u |
| 22 | 3-(2-diethylaminoethoxy) | 3-morpholino | v |
| 23 | 3-(2-pyridylmethoxy) | 3-morpholino | w |
| 24 | 4-methoxy-3-[2-(pyrrolidin-1-yl)ethoxy] | 3-morpholino | x |
| 25 | 4-methoxy-3-(2-morpholinoethoxy) | 3-morpholino | y |
| 26 | 4-methoxy-3-(2-pyridylmethoxy) | 3-morpholino | z |
| 27 | 3-(tert-butoxycarbonylmethoxy) | 3-dimethylamino | aa |
| 28 | 3-(3-piperidinopropoxy) | 3-morpholino | bb |
| 29 | 3-(3-morpholinopropoxy) | 3-morpholino | cc |
| 30 | 3-(2-diisopropylaminoethoxy) | 3-morpholino | dd |
| 31 | 3-(3-diethylaminopropoxy) | 3-morpholino | ee |
| 32 | 3-[2-(N-methylpyrrolidin-2-yl)ethoxy] | 3-morpholino | ff |
| 33 | 3-(3-pyridylmethoxy) | 3-morpholino | gg |
| 34 | 3-(4-pyridylmethoxy) | 3-morpholino | hh |
| 35 | 3-(2-methylthiazol-4-ylmethoxy) | 3-morpholino | ii |
| 36 | 3-(N-methylpiperidin-3-ylmethoxy) | 3-morpholino | jj |
| 37 | 4-(2-morpholinoethoxy) | 3-morpholino | kk |
| 38 | 4-(3-morpholinopropoxy) | 3-morpholino | ll |
| 39 | 4-[2-(pyrrolidin-1-yl)ethoxy] | 3-morpholino | mm |
| 40 | 4-(2-piperidinoethoxy) | 3-morpholino | nn |
| 41 | 4-(3-piperidinopropoxy) | 3-morpholino | oo |
| 42 | 4-[3-(4-methylpiperazin-1-yl)propoxy] | 3-morpholino | pp |
| 43 | 4-(2-diethylaminoethoxy) | 3-morpholino | qq |
| 44 | 4-(3-diethylaminopropoxy) | 3-morpholino | rr |
| 45 | 4-(2-diisopropylaminoethoxy) | 3-morpholino | ss |
| 46 | 4-(N-methylpiperidin-3-ylmethoxy) | 3-morpholino | tt |
| 47 | 4-(2-pyridylmethoxy) | 3-morpholino | uu |
| 48 | 4-(2-methylthiazol-4-ylmethoxy) | 3-morpholino | vv |
| 49 | 4-methoxy-3-(2-morpholinoethoxy) | 3-morpholino | ww |
| 50 | 4-methoxy-3-(3-morpholinopropoxy) | 3-morpholino | xx |
| 51 | 4-methoxy-3-(3-piperidinopropoxy) | 3-morpholino | yy |
| 52 | 4-methoxy-3-[3-(4-methylpiperazin-1-yl)propoxy] | 3-morpholino | zz |
| 53 | 4-methoxy-3-[2-(N-methylpyrrolidin-2-yl)ethoxy] | 3-morpholino | aaa |
| 54 | 4-methoxy-3-(N-methylpiperidin-3-ylmethoxy) | 3-morpholino | bbb |
| 55 | 3-(2-diethylaminoethoxy)-4-methoxy | 3-morpholino | ccc |
| 56 | 3-(3-diethylaminopropoxy)-4-methoxy | 3-motpholino | ddd |
| 57 | 3-(2-diisopropylaminoethoxy)-4-methoxy | 3-morpholino | eee |
| 58 | 4-methoxy-3-(2-methylthiazol-4-ylmethoxy) | 3-morpholino | fff |

Notes a) The product had m.p. 114–116° C. and gave the following data: NMR (DMSOd$_6$) 1.88 (m, 2H), 2.18 (s, 3H), 2.35 (t, 4H), 2.41 (t, 2H), 2.96 (s, 6H), 3.55 (t, 4H), 3.81 (s, 3H), 4.08 (t, 2H), 6.91 (m, 1H), 7.05 (d, 1H), 7.18 (m, 3H), 7.25 (t, 2H), 7.58 (m, 3H), 7.78 (d, 1H), 9.76 (s, 1H), 10.07 (br s, 1H); Mass M+H 547.

The N-[5-(3-dimethylaminobenzamido)-2-methylphenyl] 4-hydroxy-3-methoxybenzamide used as a starting material was prepared as follows:

Oxalyl chloride (13.0 ml) was added dropwise to a stirred mixture of 3-dimethylaminobenzoic acid (20.3 g) and DMF (a few drops) which had been cooled to 0° C. The mixture was allowed to warm to ambient temperature and was stirred for 4 hours. The resultant mixture was evaporated and the residue was dissolved in methylene chloride (150 ml). 4-Methyl-3-nitroaniline (15.2 g) and triethylamine (27.9 ml) were added in turn and the resultant mixture was stirred at ambient temperature for 16 hours. The reaction mixture was washed in turn with water, with a saturated solution of sodium bicarbonate and with brine, dried ($MgSO_4$) and evaporated. The residue was triturated under a mixture of ethyl acetate and isohexane. The solid so obtained was filtered off and recrystallised from ethanol to give N-(3-nitro4-methylphenyl)-3-dimethylaminobenzamide (6.1 g); NMR: ($DMSOd_6$) 2.46 (s, 3H), 2.95 (s, 6H), 6.92 (d, 1H), 7.22 (m, 2H), 7.32 (t, 1H), 7.45 (d, 1H),-7.97 (d, 1H), 8.53 (s, 1H), 10.43 (s, 1H); Mass M+H 300.

After repetition of the previous reactions, a sample (8.25 g) was added to a stirred suspension of ammonium formate (17.4 g), and 10% palladium-on-carbon (1 g) in methanol (250 ml). The mixture was stirred and heated to reflux for 4 hours. The mixture was allowed to cool and then filtered. The filtrate was evaporated and water was added to the residue. The resultant solid was isolated and washed in turn with water, with ethyl acetate and with diethyl ether. The solid was dried in a vacuum oven at 40° C. to give N-(3-amino-4-methylphenyl)-3-dimethylaminobenzamide (6.89 g); NMR: ($DMSOd_6$) 2.0 (s, 3H), 2.94 (s, 6H), 4.78 (s, 2H), 6.82 (m, 3H), 7.07 (s, 1H), 7.17 (m, 2H), 7.25 (m, 1H), 9.74 (s, 1H); Mass M+H 270.

A solution of 3-methoxy-4-benzyloxybenzoyl chloride (3.01 g) in methylene chloride (50 ml) was added to a stirred suspension of N-(3-amino-4-methylphenyl)-3-dimethylaminobenzamide (2.69 g) in methylene chloride (30 ml) and the reaction mixture was stirred at ambient temperature for 16 hours. The organic phase was washed with water and with a saturated aqueous sodium bicarbonate solution, dried and evaporated. The solid residue was stirred in diethyl ether for 16 hours, filtered and dried to give N-[5-(3-dimethylaminobenzamido)-2-methylphenyl]-3-methoxy-4-benzyloxybenzamide (0.458 g); NMR: ($DMSOd_6$) 2.18 (s, 3H), 2.96 (s, 6H), 3.82 (s, 3H), 5.12 (s, 2H), 6.9 (m, 1H), 7.16 (t, 1H), 7.21 (d, 2H), 7.3 (t, 2H), 7.4 (m, 5H), 7.57 (m, 3H), 7.78 (d, 1H), 9.75 (s, 1H), 10.18 (s, 1H).

After repetition of the preceding reaction, 10% palladium-on-carbon (0.25 g) was added to a stirred suspension of the material so obtained (2.55 g) in ethanol (100 ml) and the mixture was stirred at 25° C. under 1 atmosphere pressure of hydrogen. After hydrogen uptake had ceased, the catalyst was removed by filtration and the filtrate was evaporated. The residue was crystallised under methanol to give the required phenolic starting material (1.90 g); NMR: ($DMSOd_6$) 2.18 (s, 3H), 2.97 (s, 6H), 3.82 (s, 3H), 6.82 (d, 1H), 6.9 (m, 1H), 7.17 (m, 3H), 7.27 (t, 1H), 7.5 (m, 1H), 7.77 (d, 1H), 9.58 (s, 1H), 9.62 (s, 1H), 10.06 (s, 1H).

b) The product gave the following data: NMR ($DMSOd_6$) 1.62 (m, 4H), 2.18 (s, 3H), 2.56 (t, 4H), 2.8 (t, 2H), 2.96 (s, 6H), 4.16 (t, 2H), 6.91 (m, 1H), 7.15 (m, 1H), 7.21 (m, 3H), 7.3 (t, 2H), 7.46 (t, 1H), 7.50 (s, 1H), 7.57 (m, 1H), 7.78 (d, 1H), 9.86 (s, 1H), 10.08 (s, 1H); Mass M+H 487.

The N-[5-(3-dimethylaminobenzamido)-2-methylphenyl]-3-hydroxybenzamide used as a starting material was prepared by reacting N-(3-amino-4-methylphenyl)-3-dimethylaminobenzamide with 3-benzyloxybenzoyl chloride using an analogous procedure to that described in Note a) above to give an intermediate benzyloxy compound which was hydrogenated over 10% palladium-on-carbon as also described in Note a) above to give the required phenolic starting material, m.p. 224–227° C.; NMR: ($DMSOd_6$) 2.18 (s, 3H), 2.97 (s, 6H), 6.9 (m, 1H), 6.97 (m, 1H), 7.2 (m, 3H), 7.3 (m, 3H), 7.38 (d, 1H), 7.48 (m, 1H), 7.78 (d, 1H), 9.7 (br s, 1H), 9.79 (s, 1H), 10.07 (br s, 1H).

c) The product gave the following data: NMR ($DMSOd_6$) 2.18 (s, 3H), 2.46 (t, 4H), 2.71 (t, 2H), 2.96 (s, 6H), 3.57 (t, 4H), 4.18 (t, 2H), 6.9 (m, 1H), 7.18 (m, 1H), 7.21 (m, 3H), 7.28 (t, 1H), 7.42 (t, 1H), 7.58 (m, 3H), 7.79 (d, 1H), 9.82 (s, 1H), 10.08 (s, 1H); Mass M+H 503.

d) The product gave the following data: NMR ($DMSOd_6$) 2.18(s, 3H), 2.42 (t, 4H), 2.7 (t, 2H), 2.96 (s, 6H), 3.5 8 (t, 4H), 4.18 (t, 2H), 6.9 (m, 1H), 7.03 (d, 2H), 7.20 (m, 3H), 7.27 (t, 1H), 7.57 (m, 1H), 7.78 (d, 1H), 7.96 (d, 2H), 9.71 (s, 1H), 10.08 (s, 1H); Mass M+H 503.

e) The product gave the following data: NMR ($DMSOd_6$) 1.89 (m, 2H), 2.18 (s, 3H), 2.36 (t, 4H), 2.41 (t, 2H), 2.96 (s, 6H), 3.57 (t, 4H), 4.07 (t, 2H), 6.9 (m, 1H), 7.16 (m, 1H), 7.2 (m, 3H), 7.26 (t, 2H), 7.4 (t, 1H), 7.54 (m, 3H), 7.79 (d, 1H), 9.82 (s, 1H), 10.08 (s, 1H); Mass M+H 517.

f) The product gave the following data: NMR ($DMSOd_6$) 2.18 (s, 3H), 2.42 (m, 6H), 2.7 (t, 2H), 2.96 (s, 6H), 3.58 (t, 4H), 3.81 (s, 3H), 4.08 (t, 2H), 6.88 (m, 1H), 7.08 (d, 1H), 7.2 (m, 3H), 7.27 (t, 1H), 7.58 (m, 3H), 7.78 (d, 1H), 9.77 (s, 1H), 10.07 (br s, 1H); Mass M+H 533.

g) The product gave the following data: NMR ($DMSOd_6$) 1.37 (m, 2H), 1.42 (m, 4H), 2.18 (s, 1H), 2.42 (t, 4H), 2.62 (t, 2H), 2.96 (s, 6H), 3.82 (s, 3H), 4.16 (t, 2H), 6.91 (m, 1H), 7.05 (d, 1H), 7.18 (m, 3H), 7.26 (t, 1H), 7.58 (m, 3H), 7.78 (d, 1H), 9.72 (s, 1H), 10.07 (s, 1H); Mass M+H 531.

The N-[5-(3-dimethylaminobenzamido)-2-methylphenyl]-3-hydroxy-4-methoxybenzamide used as a starting material was prepared by reacting N!-(3-amino-4-methylphenyl)-3-dimethylaminobenzamide with 3-benzyloxy-4-methoxybenzoyl chloride using an analogous procedure to that described in Note a) above to give the intermediate benzyloxy compound which was hydrogenated over 10% palladium-on-carbon as also described in Note a) above to give the required phenolic starting material, m.p. 136–138° C.; NMR: ($DMSOd_6$) 2.18 (s, 3H), 2.97 (s, 6H), 3.82 (s, 3H) 7.0 (m, 1H), 7.18 (m, 3H), 7.25 (t, 1H), 7.40 (d, 1H), 7.48 (m, 1H) 7.57 (m, 1H), 7.78 (d, 1H), 9.2 (s, 1H), 9.62 (s, 1H), 10.06 (s, 1H).

h) The product gave the following data: NMR ($DMSOd_6$) 1.64 (t, 4H), 2.18 (s, 3H), 2.52 (t, 4H), 2.8 (t, 2H), 2.96 (s, 6H), 3.81 (s, 3H), 4.12 (t, 2H), 6.9 (m, 1H), 7.07 (d, 1H), 7.19 (m, 3H), 7.26 (t, 1H), 7.58 (m, 3H), 7.78 (d, 1H), 9.73 (s, 1H), 10.07 (s, 1H); Mass M+H 517.

i) The product gave the following data: NMR ($DMSOd_6$) 1.9 (m, 2H), 2.18 (s, 3H), 2.37 (t, 4H), 2.42 (t, 2H), 2.96 (s, 6H), 3.57 (t, 4H), 3.81 (s, 3H), 4.07 (t, 2H), 6.9 (m, 1H), 7.05 (d, 1H), 7.20 (m, 3H), 7.28 (t, 1H), 7.56 (m, 2H), 7.61 (m, 1H), 7.78 (d, 1H), 9.75 (s, 1H), 10.57 (s, 1H); Mass M+H 547.

j) The product gave the following data: NMR ($DMSOd_6$) 2.18 (t, 3H), 2.43 (t, 4H), 2.7 (t, 2H), 2.97 (s, 6H), 3.57 (t, 4H), 3.82 (s, 3H), 4.17 (t, 2H), 6.9 (m, 1H), 7.06 (d, 1H), 7.19 (m, 3H), 7.26 (t, 1H), 7.61 (m, 3H), 7.78 (d, 1H), 9.78 (s, 1H), 10.07 (s, 1H); Mass M+H 533.

k) The product gave the following data: NMR (DMSOd$_6$) 2.18 (s, 3H), 2.97 (s, 6H), 5.26 (s, 2H), 6.9 (m, 1H), 7.18 (d, 2H), 7.2 (m, 3H), 7.29 (t, 2H), 7.35 (m, 1H), 7.57 (m, 2H), 7.82 (m, 2H), 7.95 (d, 2H), 8.58 (d, 1H), 9.72 (s, 1H), 10.07 (s, 1H); Mass M+H 481.

l) The product gave the following data: NMR (DMSOd$_6$) 2.18 (s, 3H), 2.96 (s, 6H), 5.25 (s, 2H), 6.9 (m, 1H), 7.29 (m, 6H), 7.42 (t, 1H), 7.56 (m, 4H), 7.81 (m, 2H), 8.58 (d, 1H), 9.82 (s, 1H), 10.08 (s, 1H); Mass M+H 481.

m) The alkylating agent was 2-bromoethyl methyl ether. The product gave the following data: NMR (DMSOd$_6$) 2.18 (s, 3H), 2.95 (s, 6H), 3.67 (m, 2H), 4.17 (m, 2H), 6.85 (d, 1H), 7.04 (d, 2H), 7.24 (m, 4H), 7.58 (d, 1H), 7.78 (s, 1H), 7.96 (d, 2H), 9.42 (s, 1H), 10.09 (s, 1H); Mass M+H 448.

n) The product gave the following data: NMR (DMSOd$_6$) 1.38 (s, 4H), 2.21 (s, 3H), 2.38 (t, 4H), 2.81 (t, 4H), 2.97 (s, 6H), 4.35 (t, 4H), 6.89 (m, 1H), 7.11 (t, 1H), 7.25 (m, 6H), 7.55 (m, 2H), 7.94 (d, 1H), 7.95 (s, 1H), 10.07 (br s, 1H), 10.26 (br s, 1H); Mass M+H 487.

The N-[5-(3-dimethylaminobenzamido)-2-methylphenyl]-2-hydroxybenzamide used as a starting material was prepared as follows:

A solution of 2-benzyloxybenzoyl chloride (2.69 g) in methylene chloride (50 ml) was added dropwise to a stirred mixture of N-(3-amino-4-methylphenyl)-3-dimethylaminobenzamide (2.69 g), pyridine (3 ml) and methylene chloride (50 ml) which had been cooled to 5° C. The reaction mixture was stirred for 16 hours at ambient temperature. The organic phase was washed with water and with a saturated aqueous sodium bicarbonate solution, dried (MgSO$_4$) and evaporated. The residue was stirred under diethyl ether for 16 hours to give a precipitate which was isolated and dried. There was this obtained N-[5-(3-dimethylaminobenzamido)-2-methylphenyl]-2-benzyloxybenzamide (4.3 g), m.p. 136–139° C.; NMR: (DMSOd$_6$) 1.85 (s, 3H), 2.98 (s, 6H), 5.36 (s, 2H), 6.9 (d, 1H), 7.12 (m, 2H), 7.33 (m, 7H), 7.52 (m, 4H), 7.9 (d, 1H), 8.12 (s, 1H), 9.7 (s, 1H), 10.08 (br s, 1H); Mass: M+H 480.

10% Palladium-on-carbon (0.25 g) was added to a stirred suspension of a portion (2.4 g) of the material so obtained in ethanol (125 ml) and the resultant mixture was stirred at ambient temperature under 1 atmosphere pressure of hydrogen. After uptake of hydrogen had ceased, the catalyst was removed by filtration and the filtrate was evaporated. The residue was triturated under methanol. There was thus obtained the required starting material (1.36 g), m.p. 234–238° C.; NMR: (DMSOd$_6$) 2.22 (s, 3H), 2.97 (s, 6H), 6.92 (m, 3H), 7.21 (m, 3H), 7.3 (q, 1H), 7.42 (m, 1H), 7.57 (m, 1H), 8.02 (m, 1H), 8.21 (d, 1H), 10.15 (br s, 1H), 10.38 (br s, 1H); Mass: M+H 390.

o) The product gave the following data: NMR (DMSOd$_6$) 1.63 (m, 4H), 2.18 (s, 3H), 2.52 (t, 4H), 2.78 (t, 2H), 2.96 (s, 6H), 4.18 (t, 2H), 6.9 (m, 1H), 7.03 (d, 2H), 7.18 (m, 3H), 7.25 (t, 1H), 7.56 (m, 1H), 7.78 (d, 1H), 7.94 (d, 2H), 9.73 (s, 1H), 10.07 (s, 1H); Mass M+H 487.

p) The product gave the following data: NMR (DMSOd$_6$) 1.62 (s, 4H), 2.16 (s, 3H), 2.46 (s, 4H), 2.8 (t, 2H), 2.96 (s, 6H), 3.82 (s, 3H), 4.1 (t, 2H), 6.88 (m, 1H), 7.08 (d, 1H), 7.2 (d, 3H), 7.27 (t, 1H), 7.48 (m, 4H), 7.78 (s, 1H), 9.75 (s, 1H), 10.07 (s, 1H); Mass M+H 517.

q) The product gave the following data: NMR (DMSOd$_6$) 2.18 (s, 3H), 2.94 (s, 6H), 3.83 (s, 3H), 5.23 (s, 2H), 6.9 (m, 1H), 7.14 (d, 1H), 7.2 (m, 3H), 7.26 (t, 1H), 7.35 (m, 1H), 7.53 (m, 4H), 7.77 (d, 1H), 7.82 (m, 1H), 8.58 (d, 1H), 9.75 (s, 1H), 10.07 (br s, 1H); Mass M+H 511.

r) The product gave the following data: NMR (DMSOd$_6$) 1.41 (s, 9H), 2.18 (s, 3H), 2.94 (s, 6H), 3.82 (s, 3H), 5.23 (s, 2H), 6.9 (m, 1H), 6.94 (d, 1H), 7.2 (m, 3H), 7.26 (t, 1H), 7.57 (m, 3H), 7.77 (d, 1H), 9.78 (s, 1H), 10.08 (s, 1H); Mass M+H 532.

s) The product gave the following data: NMR (DMSOd$_6$) 1.62 (t, 4H), 2.19 (s, 3H), 2.52 (t, 4H), 2.8 (t, 2H), 3.17 (t, 4H), 3.76 (t, 4H), 4.16 (t, 2H), 6.9 (m, 1H), 7.15 (m, 1H), 7.21 (m, 3H), 7.3 (t, 2H), 7.4 (t, 1H), 7.51 (s, 1H), 7.57 (m, 1H), 7.78 (s, 1H), 9.7 (s, 1H), 9.9 (s, 1H); Mass M+H 529.

The N-[2-methyl-5-(3-morpholinobenzamido)phenyl]-3-hydroxybenzamide used as a starting material was prepared as follows:

A solution of 3-morpholinobenzoyl chloride (0.24 g) in methylene chloride (5 ml) was added to a stirred mixture of 4-methyl-3-nitroaniline (0.15 g), pyridine (0.24 ml) and methylene chloride (10 ml). The reaction mixture was stirred at ambient temperature for 16 hours. The organic phase was washed with water and with a saturated aqueous sodium bicarbonate solution. The organic layer was dried (MgSO$_4$) and evaporated. The residual solid was triturated under diethyl ether and the resultant solid was isolated and dried to give N-(3-nitro4-methylphenyl)-3-morpholinobenzamide (0.28 g); NMR: (DMSOd$_6$) 3.2 (t, 4H), 3.3 (s, 3H), 3.78 (t, 4H), 7.19 (s, 1H), 7.4 (m, 2H), 7.47 (d, 2H), 8.0 (d, 1H), 8.83 (s, I1H), 10.23 (s, 1H).

10% Palladium-on-carbon (0.035 g) was added to a stirred solution in methanol (40 ml) of the nitro compound so obtained (0.28 g) and the mixture was stirred at ambient temperature under 1 atmosphere pressure of hydrogen. After uptake of hydrogen had ceased, the catalyst was removed by filtration and the filtrate was evaporated to give N-(3-amino-4-methylphenyl)-3-morpholinobenzamide; NMR: (DMSOd$_6$) 2.0 (s, 3H), 3.19 (t, 4H), 3.78 (t, 4H), 4.8 (s, 2H), 6.8 (q, 2H), 7.08 (s, 1H), 7.1 (d, 1H), 7.34 (m, 2H), 7.4 (s, 1H), 9.8 (s, 1H); Mass: M+H 312.

After repetition of the preceding steps, a solution of 3-benzyloxybenzoyl chloride (1.33 g) in methylene chloride (20 ml) was added to a stirred mixture of N-3-amino-4-methylphenyl)-3-morpholinobenzamide (1.55 g), pyridine (1 ml) and methylene chloride (20 ml). The reaction mixture was stirred at ambient temperature for 18 hours. The organic phase was washed with water and with a saturated aqueous sodium bicarbonate solution, dried (MgSO$_4$) and evaporated. The residue was stirred under diethyl ether for 20 hours. The precipitate was isolated and dried. There was thus obtained N-[2-methyl-5-(3-morpholinobenzamido)phenyl]-3-benzyloxybenzamide (2.21 g); m.p. 192–193° C.; NMR: (DMSOd$_6$) 2.18 (s, 3H), 3.16 (t, 4H), 3.76 (t, 4H), 5.18 (s, 2H), 7.15 (d, 1H), 7.21 (d, 2H), 7.4 (m, 9H), 7.56 (d, 2H), 7.58 (s, 1H), 7.8 (d, 1H), 9.85 (s, 1H), 10.12 (br s, 1H); Mass: M+H 522.

10% Palladium-on-carbon catalyst (0.2 g) was added to a stirred suspension of a portion (1.94 g) of the material so obtained in ethanol (200 ml) The mixture was stirred at ambient temperature under 1 atmosphere pressure of hydrogen. After cessation of hydrogen uptake, the catalyst was removed and the filtrate was evaporated. The residue was triturated under methanol. There was thus obtained the required starting material (0.825 g), m.p. 227–229° C.; NMR: (DMSOd$_6$) 2.19 (s, 3H), 3.18 (t, 4H), 3.77 (t, 4H), 6.98 (m, 1H), 7.15 (m, 1H), 7.21 (d, 1H), 7.31 (t, 1H), 7.38 (m, 5H), 7.58 (m, 1H), 7.78 (s, 1H), 9.68 (s, 1H), 9.78 (s, 1H), 10.1 (s, 1H); Mass: M+H 432.

The 3-morpholinobenzoyl chloride used as a starting material was prepared as follows:

A mixture of ethyl 3-bromobenzoate (1.92 ml), morpholine (1.25 ml), 2,2'-bis(diphenylphosphino)-1,1'-binaphthyl (0.336 g), sodium tert-butoxide (1.615 g) and tris (dibenzylideneacetone)dipalladium(0) (0.33 g) and toluene (25 ml) was stirred and heated to 90° C. for 18 hours under argon. The reaction mixture was allowed to cool to ambient temperature and extracted with 1N aqueous hydrochloric acid. The aqueous phase was basified with concentrated sodium hydroxide solution and extracted with ethyl acetate. The organic phase was dried (MgSO$_4$) and evaporated. The residual oil was purified by column chromatography on silica gel using a 47:3 mixture of methylene chloride and methanol as eluent. There was thus obtained N-(3-morpholinobenzoyl)morpholine (0.45 g).

A mixture of the material so obtained, 5M sodium hydroxide solution (2.5 ml) and butanol (2 ml) was stirred and heated to 115° C. for 18 hours. The mixture was evaporated and the residue was acidified by the addition of 1N aqueous hydrochloric acid solution (12.5 ml). The resultant precipitate was isolated, washed with water and dried to give 3-morpholinobenzoic acid (0.15 g); NMR (DMSOd$_6$) 3.1 (t, 4H), 3.73 (t, 4H), 7.19 (d, 1H), 7.32 (d, 1H), 7.38 (t, 1H), 7.42 (s, 1H).

Oxalyl chloride (0.14 ml) was added to a solution of 3-morpholinobenzoic acid (0.28 g) in methylene chloride (10 ml) which contained DMF (2 drops). The reaction mixture was stirred for 18 hours at ambient temperature. The mixture was evaporated and azeotroped with toluene to give 3-morpholinobenzoyl chloride (0.3 g); Mass M+H 222.

t) The product gave the following data: NMR (DMSOd$_6$) 1.31 (m, 2H), 1.45 (m, 4H), 2.19 (s, 3H), 2.45 (t, 4H), 2.71 (t, 2H), 3.19 (t, 4H), 3.76 (t, 4H), 4.18 (t, 2H), 7.13 (d, 2H), 7.22 (d, 1H), 7.4 (m, 3H), 7.43 (s, 1H), 7.53 (s, 2H), 7.57 (d, 1H), 7.78 (d, 1H), 9.82 (s, 1H), 10.1 (s, 1H); Mass M+H 543.

u) The product gave the following data: NMR (DMSOd$_6$) 2.18 (s, 3H), 2.46 (t, 4H), 2.7 (t, 2H), 3.18 (t, 4H), 3.57 (t, 4H), 3.76 (t, 4H), 4.17 (t, 2H), 7.17 (m, 2H), 7.21 (d, 1H), 7.37 (m, 2H), 7.42 (m, 2H), 7.57 (m, 3H), 7.78 (d, 1H), 9.85 (s, 1H), 10.1 (s, 1H); Mass M+H 545.

v) The product gave the following data: NMR (DMSOd$_6$) 0.98 (t, 6H), 1.98 (s, 3H), 2.56 (q, 4H), 2.78 (t, 2H), 3.18 (t, 4H), 3.77 (t, 4H), 4.08 (t, 2H), 7.14 (d, 2H), 7.21 (d, 1H), 7.36 (m, 2H), 7.41 (m, 2H), 7.5 (m, 2H), 7.57 (m, 1H), 7.78 (d, 1H), 9.82 (s, 1H), 10.11 (s, 1H); Mass M+H 531.

w) The product gave the following data: NMR (DMSOd$_6$) 2.22 (s, 3H), 3.22 (t, 4H), 3.79 (t, 4H), 5.23 (s, 2H), 7.12 (m, 1H), 7.28 (t, 3H), 7.42 (m, 3H), 7.48 (t, 2H), 7.6 (d, 1H), 7.62 (s, 1H), 7.65 (d, 1H), 7.85 (s, 1H), 7.9 (m, 1H), 8.6 (d, 1H), 9.9 (s, 1H), 10.15 (s, 1H); Mass M+H 523.

x) The product gave the following data: NMR (DMSOd$_6$) 1.62 (t, 4H), 2.18 (s, 3H), 2.47 (t, 4H), 2.8 (t, 2H), 3.18 (t, 4H), 3.76 (t, 4H), 3.84 (s, 3H), 4.13 (t, 2H), 7.04 (d, 1H), 7.07 (m, 1H), 7.19 (d, 1H), 7.37 (m, 3H), 7.41 (s, 1H), 7.57 (m, 2H), 7.78 (s, 1H), 9.73 (s, 1H), 10.11 (s, 1H); Mass M+H 559.

The N-[2-methyl-5-(3-morpholinobenzamido)phenyl]-3-hydroxy-4-methoxybenzamide used as a starting material was prepared by reacting N-(3-amino-4-methylphenyl)-3-morpholinobenzamide with 3-benzyloxy-4-methoxybenzoyl chloride using an analogous procedure to that described in Note a) above to give an intermediate benzyloxy compound which was hydrogenated over 10% palladium-on-carbon as also described in Note a) above to give the required phenolic starting material; NMR (DMSOd$_6$) 2.16 (s, 3H), 3.18 (t, 4H), 3.78 (t, 4H), 3,82 (s, 3H), 7.01 (m, 1H), 7.14 (t, 1H), 7.18 (d, 1H), 7.35 (m, 6H), 7.58 (m, 1H), 9.21 (s, 1H), 9.53 (s, 1H), 10.1 (br s, 1H); Mass M+H 462.

y) The product gave the following data: NMR (DMSOd$_6$) 1.32 (m, 2H), 1.44 (m, 4H), 2.18 (s, 3H), 2.39 (t, 4H),2.62 (t, 2H), 3.18 (t, 4H), 3.78 (t, 4H), 3.81 (s, 3H), 4.12 (t, 2H), 7.07 (d, 1H), 7.16 (m, 1H), 7.21 (d, 1H), 7.37 (m, 2H), 7.42 (s, 1H), 7.57 (m, 3H), 7.78 (s, 1H), 9.73 (s, 1H), 10.11 (s, 1H); Mass M+H 573.

z) The product gave the following data: NMR (DMSOd$_6$) 2.18 (s, 3H), 3.18 (t, 4H), 3.77 (t, 4H), 3.83 (s, 3H), 5.21 (s, 2H), 7.1 (d, 2H), 7.21 (d, 1H), 7.37 (m, 3H), 7.42 (s, 1H), 7.57 (m, 2H), 7.64 (m, 2H), 7.77 (s, 1H), 7.82 (m, 1H), 8.58 (d, 1H), 9.73 (s, 1H), 10.1 (s, 1H); Mass M+H 553.

aa) The product gave the following data: Mass M+H 515.

bb) The product gave the following data: NMR (DMSOd$_6$) 1.36 (d, 2H), 1.46 (m, 4H), 1.86 (m, 2H), 2.18 (s, 3H), 2.4 (m, 6H), 3.19 (t, 4H), 3.75 (t, 4H), 4.06 (t, 2H), 7.11 (d, 2H), 7.22 (d, 1H), 7.39 (m, 3H), 7.56 (m, 3H), 7.78 (s, 1H), 9.86 (s, 1H), 10.11 (s, 1H); Mass M+H 557.

cc) The reactants were heated to 100° C. for 24 hours. The product gave the following data: NMR (DMSOd$_6$) 1.9 (m, 2H), 2.19 (s, 3H), 2.38 (t, 4H), 2.4 (d, 2H), 3.18 (t, 4H), 3.57 (t, 4H), 3.78 (t, 4H), 4.08 (t, 2H), 7.12 (d, 2H), 7.21 (d, 1H), 7.37 (m, 4H), 7.57 (m, 3H), 7.78 (d, 1H), 9.82 (s, 1H), 10.11 (s, 1H); Mass M+H 559.

dd) The product gave the following data: NMR (DMSOd$_6$) 0.97 (d, 12H), 2.19 (s, 3H), 2.78 (t, 2H), 3.01 (t, 3H), 3.18 (t, 4H), 3.74 (t, 4H), 3.93 (t, 4H), 7.1 (m, 2H), 7.21 (d, 1H), 7.4 (m, 4H), 7.52 (m, 3H), 7.79 (s, 1H), 9.85 (s, 1H), 10.11 (s, 1H); Mass M+H 559.

ee) The product gave the following data: NMR (DMSOd$_6$) 0.96 (t, 6H), 1.83 (m, 2H), 2.19 (s, 3H), 2.48 (m, 6H), 3.17 (t, 4H), 3.72 (t, 4H), 4.07 (t, 2H), 7.1 (m, 2H), 7.12 (d, 1H), 7.39 (m, 4H), 7.53 (m, 3H), 7.78 (s, 1H), 9.83 (s, 1H), 10.11 (s, 1H); Mass M+H 545.

ff) The reaction product was purified by column chromatography on silica using a 9:1 mixture of methylene chloride and methanol as eluent. The product so obtained gave the following data: NMR (DMSOd$_6$) 1.7 (m, 5H), 2.04 (m, 2H), 2.17 (s, 3H), 2.23 (d, 3H), 3.18 (t, 4H), 3.75 (t, 4H), 4.07 (t, 1H), 7.1 (m, 2H), 7.22 (d, 1H), 7.4 (m, 4H), 7.53 (m, 3H), 7.78 (s, 1H), 9.85 (d, 1H), 10.11 (s, 1H); Mass M+H 543.

gg) The reactants were stirred at 25° C. for 36 hours rather than being heated to 60° C. The product gave the following data: NMR (DMSOd$_6$) 2.19 (s, 3H), 3.18 (t, 4H), 3.78 (t, 4H), 5.21 (s, 2H), 7.12 (d, 2H), 7.37 (m, 5H), 7.57 (m, 2H), 7.6 (s, 1H), 7.78 (d, 1H) 7.86 (d, 1H), 8.54 (d, 1H), 8.7 (s, 1H), 9.95 (s, 1H), 10.11 (s, 1H); Mass M+H 523.

hh) The reactants were stirred at 25° C. for 36 hours rather than being heated to 60° C. The product gave the following data: NMR (DMSOd$_6$) 2.14 (s, 3H), 3.15 (t, 4H), 3.74 (t, 4H), 5.28 (s, 2H), 7.1 (m, 1H), 7.21 (m, 2H), 7.37 (m, 2H), 7.45 (m, 4H), 7.57 (m, 3H), 7.78 (s, 1H), 8.58 (d, 2H), 9.91 (s, 1H), 10.12 (s, 1H); Mass M+H 523.

ii) The product gave the following data: NMR (DMSOd$_6$) 2.2 (s, 3H), 2.63 (s, 3H), 3.18 (t, 4H), 3.76 (t, 4H), 5.18 (s, 1H), 7.11 (d, 1H), 7.23 (t, 2H), 7.36 (m, 2H), 7.42 (t, 2H), 7.59 (m, 4H), 7.79 (s, 1H), 9.84 (s, 1H), 10.11 (s, 1H); Mass M+H 543.

jj) The product gave the following data: NMR (DMSOd$_6$) 1.05 (t, 4H), 2.18 (d, 6H), 3.19 (s, 4H), 3.73 (s, 4H), 3.89 (t, 2H), 7.1 (d, 2H), 7.19 (d, 1H), 7.39 (m, 4H), 7.53 (m, 3H), 7.79 (s, 1H), 9.85 (s, 1H), 10.1 (s, 1H); Mass M+H 543.

kk) The product gave the following data: NMR (DMSOd$_6$) 2.19 (s, 3H), 2.7 (t, 2H), 3.17 (t, 3H), 3.28 (m, 4H), 3.57 (t, 4H), 3.76 (t, 4H), 4.17 (t, 2H), 7.04 (d, 2H), 7.11 (m, 1H), 7.19 (d, 1H), 7.35 (m, 2H), 7.42 (s, 1H), 7.55 (m, 1H), 7.77 (s, 1H), 7.92 (m, 2H), 9.7 (s, 1H), 10.1 (s, 1H); Mass M+H 545.

The N-[2-methyl-5-(3-morpholinobenzamido)phenyl]-4-hydroxybenzamide used as a starting material was prepared as follows:

A solution of 4-benzyloxybenzoyl chloride [obtained by the reaction of 4-benzyloxybenzoic acid (8.66 g) and oxalyl chloride (4 ml)] in methylene chloride (300 ml) was added to a stirred mixture of N-(3-amino-4-methylphenyl)-3-morpholinobenzamide (10.6 g), pyridine (5.42 ml) and methylene chloride (300 ml). The reaction mixture was stirred at ambient temperature for 18 hours. The organic phase was washed with water and with a saturated aqueous sodium bicarbonate solution, dried (MgSO$_4$) and evaporated. The residue was stirred under diethyl ether for 2 hours. The precipitate was isolated and dried. There was thus obtained N-[2-methyl-5-(3-morpholinobenzamido)phenyl]-4-benzyloxybenzamide (16.1 g); NMR: (DMSOd$_6$) 2.19 (s, 3H), 3.17 (t, 4H), 3.75 (t, 4H), 5.19 (s, 2H), 7.11 (d, 2H), 7.2 (d, 1H), 7.39 (m, 9H), 7.58 (m, 1H), 7.79 (s, 1H), 7.97 (d, 2H), 9.71 (s, 1H), 10.1 (s, 1H); Mass: M+H 522.

10% Palladium-on-carbon catalyst (1.8 g) was added to a stirred suspension of a portion (14.6 g) of the material so obtained in methanol (750 ml) The mixture was stirred at ambient temperature under 1 atmosphere pressure of hydrogen. After cessation of hydrogen uptake, the catalyst was removed and the filter cake was washed with warm DMF (500 ml). The filtrate was concentrated to a volume of approximately 50 ml and poured into water. The solid so obtained was isolated and dried. There was thus obtained the required starting material (9.95 g), NMR: (DMSOd$_6$) 2.19 (s, 3H), 3.18 (t, 4H), 3.74 (t, 4H), 6.93 (m, 1H), 7.15 (m, 1H), 7.21 (d, 1H), 7.37 (m, 6H), 7.58 (m, 1H), 7.78 (s, 1H), 9.83 (s, 1H), 10.1 (s, 1H); Mass: M−H 430.

ll) The product gave the following data: NMR (DMSOd$_6$) 1.87 (m, 2H), 2.18 (s, 3H), 2.42 (m, 2H), 3.17 (t, 4H), 3.54 (t, 4H), 3.75 (t, 4H), 4.07 (t, 2H), 7.03 (d, 2H), 7.12 (m, 1H), 7.2 (d, 1H), 7.34 (m, 2H), 7.42 (s, 1H), 7.57 (m, 1H), 7.78 (s, 1H), 7.93 (d, 2H), 9.69 (s, 1H), 10.1 (s, 1H); Mass M+H 559.

mm) The product gave the following data: NMR (DMSOd$_6$) 1.67 (s, 4H), 2.18 (s, 3H), 2.81 (t, 2H), 3.18 (t, 4H), 3.74 (t, 4H), 4.17 (t, 2H), 7.04 (d, 2H), 7.14 (m, 1H), 7.21 (d, 1H), 7.37 (m, 2H), 7.43 (s, 1H), 7.57 (m, 1H), 7.79 (s, 1H), 7.96 (d, 2H), 9.7 (s, 1H), 10.1 (s, 1H); Mass M+H 529.

nn) The product gave the following data: NMR (DMSOd$_6$) 1.36 (m, 2H), 1.47 (m, 4H), 2.17 (s, 3H), 2.41 (m, 4H), 2.65 (t, 2H), 3.17 (t, 4H), 3.74 (t, 4H), 4.16 (t, 2H), 7.03 (d, 2H), 7.12 (m, 1H), 7.19 (d, 1H), 7.36 (m, 2H), 7.43 (s, 1H), 7.56 (m, 1H), 7.78 (m, 1H), 7.95 (d, 2H), 9.7 (s, 1H), 10.1 (s, 1H); Mass M+H 543.

oo) The product gave the following data: NMR (DMSOd$_6$) 1.34 (m, 2H), 1.49 (m, 4H), 1.86 (m, 2H), 2.19 (s, 3H), 2.37 (m, 6H), 3.19 (t, 4H), 3.76 (t, 4H), 4.07 (t, 2H), 7.02 (d, 2H), 7.12 (m, 1H), 7.2 (d, 1H), 7.37 (m, 2H), 7.43 (s, 1H), 7.58 (d, 1H), 7.79 (s, 1H), 7.95 (d, 2H), 9.72 (s, 1H), 10.09 (s, 1H); Mass M+H 557.

pp) The product gave the following data: NMR (DMSOd$_6$) 1.85 (m, 2H), 2.16 (d, 6H), 2.37 (m, 10H), 3.17 (t, 4H), 3.75 (t, 4H), 4.05 (t, 2H), 7.02 (d, 2H), 7.12 (m, 1H), 7.2 (d, 1H), 7.36 (m, 2H), 7.43 (s, 1H), 7.56 (m, 1H), 7.78 (s, 1H), 7.95 (d, 2H), 9.7 (s, 1H), 10.1 (s, 1H); Mass M+H 572.

qq) The product gave the following data: NMR (DMSOd$_6$) 0.96 (t, 6H), 2.18 (s, 3H), 2.56 (m, 4H), 2.68 (t, 2H), 3.18 (t, 4H), 3.75 (t, 4H), 4.08 (t, 2H), 7.02 (d, 2H), 7.1 (m, 1H), 7.20 (d, 1H), 7.35 (m, 2H), 7.43 (s, 1H), 7.54 (m, 1H), 7.78 (s, 1H), 7.93 (d, 2H), 9.68 (s, 1H), 10.1 (s, 1H); Mass M+H 531.

rr) The product gave the following data: NMR (DMSOd$_6$) 0.95 (t, 6H), 1.82 (m, 2H), 2.18 (s, 3H), 2.46 (m, 6H), 3.18 (t, 4H), 3.74 (t, 4H), 4.06 (t, 2H), 7.01 (d, 2H), 7.12 (m, 1H), 7.19 (d, 1H), 7.35 (m, 2H), 7.42 (s, 1H), 7.56 (m, 1H), 7.77 (d, 1H), 7.94 (d, 2H), 9.7 (s, 1H), 10.09 (s, 1H); Mass M+H 545.

ss) The product gave the following data: NMR (DMSOd$_6$) 0.97 (d, 12H), 2.19 (s, 3H), 2.78 (t, 2H), 3.01 (m, 2H), 3.18 (t, 4H), 3.74 (t, 4H), 3.95 (t, 2H), 7.01 (d, 2H), 7.13 (m, 1H), 7.2 (d, 1H), 7.37 (m, 2H), 7.43 (s, 1H), 7.55 (m, 1H), 7.77 (d, 1H), 7.95 (d, 2H), 9.7 (s, 1H), 10.09 (s, 1H); Mass M+H 559.

tt) The product gave the following data: NMR (DMSOd$_6$) 1.05 (m, 1H), 1.7 (m, 6H), 2.17 (d, 6H), 2.61 (m, 1H), 2.79 (m, 1H), 3.17 (t, 4H), 3.74 (t, 4H), 3.91 (m, 2H), 7.03 (d, 2H), 7.12 (m, 1H), 7.2 (d, 1H), 7.35 (m, 2H), 7.42 (s, 1H), 7.55 (m, 1H), 7.77 (s, 1H), 7.95 (d, 2H), 9.69 (s, 1H), 10.09 (s, 1H); Mass M+H 543.

uu) The product gave the following data: NMR (DMSOd$_6$) 2.19 (s, 3H), 3.18 (t, 4H), 3.73 (t, 4H), 5.23 (s, 2H), 7.12 (d, 3H), 7.2 (d, 1H), 7.34 (m, 3H), 7.42 (s, 1H), 7.54 (m, 2H), 7.8 (m, 2H), 7.97 (d, 2H), 8.58 (d, 1H), 9.72 (s, 1H), 10.1 (s, 1H); Mass M+H 523.

vv) The product gave the following data: NMR (DMSOd$_6$) 2.19 (s, 3H), 2.63 (s 3H), 3.17 (t, 4H), 3.75 (t, 4H), 5.19 (s, 2H), 7.1 (d, 3H), 7.2 (d, 1H), 7.37 (m, 2H), 7.43 (s, 1H), 7.57 (m, 2H), 7.79 (d, 1H), 7.95 (d, 2H), 9.72 (s, 1H), 10.1 (s, 1H); Mass M+H 543.

ww) The reactants were heated to 100° C. for 24 hours. The product gave the following data: NMR (DMSOd$_6$) 2.18 (s, 3H), 2.42 (t, 4H), 2.7 (t, 2H), 3.18 (t, 4H), 3.56 (t, 4H), 3.77 (t, 4H), 3.82 (s, 3H), 4.17 (t, 2H), 7.05 (d, 1H), 7.15 (m, 1H), 7.21 (d, 1H), 7.35 (m, 2H), 7.42 (s, 1H), 7.58 (m, 3H), 7.78 (s, 1H), 9.75 (s, 11H), 10.1 (s, 1H); Mass M+H 575.

xx) The reactants were heated to 100° C. for 24 hours. The product gave the following data: NMR (DMSOd$_6$) 1.82 (m, 2H), 2.15 (s, 3H), 2.37 (t, 4H), 2.4 (t, 2H), 3.18 (t, 4H), 3.56 (t, 4H), 3.76 (t, 4H), 4.03 (t, 2H), 7.02 (d, 1H), 7.12 (m, 1H), 7.2 (d, 1H), 7.37 (m, 2H), 7.41 (s, 1H), 7.52 (m, 2H), 7.6 (m, 1H), 7.78 (d, 1H), 9.75 (s, 1H), 10.1 (s, 1H); Mass M+H 589.

yy) The reactants were heated to 100° C. for 24 hours. The product gave the following data: NMR (DMSOd$_6$) 1.42 (m, 2H), 1.56 (m, 4H), 1.96 (m, 2H), 2.22 (s, 3H), 2.4 (t, 4H), 2.46 (t, 2H), 3.22 (t, 4H), 3.82 (t, 4H), 3.9 (s, 3H), 4.13 (t, 2H), 7.11 (d, 1H), 7.2 (m, 1H), 7.23 (d, 1H), 7.4 (t, 1H), 7.42 (s, 1H), 7.5 (s, 1H), 7.61 (d, 2H), 7.65 (m, 1H), 7.82 (d, 1H), 9.81 (s, 1H), 10.17 (s, 1H); Mass M+H 587.

zz) The reactants were heated to 100° C. for 24 hours. The product gave the following data: NMR (DMSOd$_6$) 1.82 (t, 2H), 2.15 (s, 3H), 2.19 (s, 3H), 2.38 (m, 10H), 3.19 (t, 4H), 3.77 (t, 4H), 3.82 (s, 4H), 4.03 (t, 2H), 7.05 (d, 1H), 7.1 (m, 1H), 7.17 (m, 1H), 7.37 (m, 2H), 7.41 (s, 1H), 7.57 (m, 3H), 7.78 (s, 1H), 9.75 (s, 1H), 10.1 (s, 1H); Mass M+H 602.

aaa) The reactants were heated to 100° C. for 24 hours. The product gave the following data: NMR (DMSOd$_6$) 1.52 (m, 1H), 1.73 (m, 2H), 2.02 (m,2H), 2.15 (s, 3H), 2.22 (s, 3H), 2.45 (m, 2H), 2.56 (m, 2H), 3.16 (t, 4H), 3.75 (t, 4H), 3.82 (s, 3H), 4.07 (t, 2H), 7.05 (d, 1H), 7.12 (m, 1H), 7.18 (d, 1H), 7.33 (m, 2H), 7.37 (s, 1H), 7.48 (s, 1H), 7.52 (d, 1H), 7.57 (d, 1H), 7.78 (s, 1H), 9.72 (s, 1H), 10.08 (s, 1H); Mass M+H 573.

bbb) The reactants were heated to 100° C. for 24 hours. The product gave the following data: NMR (DMSOd$_6$) 1.1 (m, 1H), 1.44 (m, 1H), 1.63 (m, 2H),1.93 (m, 3H), 2.18 (s, 3H), 2.19 (s, 3H), 2.6 (m, 1H), 2.81 (m, 1H), 3.18 (t, 4H), 3.78 (t, 4H), 3.82 (s, 3H), 3.91 (m, 2H), 7.03 (d, 1H), 7.12 (m, 1H), 7.2 (d, 1H), 7.37 (t, 1H), 7.38 (s, 1H), 7.42 (s, 1H), 7.57 (s, 2H), 7.6 (t, 1H), 7.78 (d, 1H), 9.75 (s, 1H), 10.09 (s, 1H); Mass M+H 573.

ccc) The reactants were heated to 100° C. for 24 hours. The product gave the following data: NMR (DMSOd$_6$) 0.98 (t, 6H), 2.18 (s, 3H), 2.52 (m, 4H), 2.8 (t, 2H), 3.18 (t, 4H), 3.78 (t, 4H), 3.82 (s, 3H), 4.05 (t, 2H), 7.05 (d, 1H), 7.15 (m, 1H), 7.21 (d, 1H), 7.37 (m, 2H), 7.41 (s, 1H), 7.57 (m, 3H), 7.78 (d, 1H), 9.75 (s, 1H), 10.1 (s, 1H); Mass M+H 561.

ddd) The product gave the following data: NMR (DMSOd$_6$) 0.95 (t, 6H), 1.81 (m, 2H), 2.18 (s, 3H), 2.43 (m, 6H), 3.18 (t, 4H), 3.75 (t, 4H), 3.82 (s, 3H), 4.03 (t, 2H), 7.03 (d, 1H), 7.12 (m, 1H), 7.21 (d, 1H), 7.37 (m, 2H), 7.42 (s, 1H), 7.52 (s, 2H), 7.57 (m, 1H), 7.76 (d, 1H), 9.75 (s, 1H), 10.1 (s, 1H); Mass M+H 575.

eee) The reactants were heated to 100° C. for 24 hours. The product gave the following data: NMR (DMSOd$_6$) 0.98 (d, 12H), 2.18 (s, 3H), 2.78 (t, 2H), 3.0 (m, 2H), 3.18 (t, 4H), 3.77 (t, 4H), 3.82 (s, 3H), 3.93 (t, 2H), 7.05 (d, 1H), 7.13 (m, 1H), 7.2 (d, 1H), 7.35 (t, 1H), 7.37 (s, 1H), 7.42 (s, 1H), 7.58 (m, 3H), 7.78 (d, 1H), 9.75 (s, 1H), 10.08 (s, 1H); Mass M+H 589.

fff) The reactants were heated to 100° C. for 24 hours. The product gave the following data: NMR (DMSOd$_6$) 2.19 (s, 3H), 2.63 (s, 3H), 3.18 (t, 4H), 3.76 (t, 4H), 3.82 (s, 3H), 5.17 (s, 2H), 7.11 (d, 1H), 7.16 (m, 1H), 7.21 (d, 1H), 7.37 (m, 2H), 7.42 (s, 1H), 7.5 (s, 1H), 7.57 (m, 1H), 7.62 (m, 1H), 7.7 (d, 1H), 7.78 (d, 1H), 9.75 (s, 1H), 10.1 (s, 1H); Mass M+H573.

EXAMPLE 8

N-[5-(4-cyanobenzamido)-2-methylphenyl]-4-(2-methoxyethoxy)benzamide

2-Bromoethyl methyl ether (0.023 ml) was added to a suspension of N-[5-(4-cyanobenzamido)-2-methylphenyl]-4-hydroxybenzamide (0.06 g) and potassium carbonate (0.045 g) in DMF (3 ml) and the reaction mixture was stirred and heated to 80° C. for 5 hours. The mixture was poured into water and extracted with ethyl acetate. The organic extract was dried (MgSO$_4$) and evaporated. The residue was triturated under diethyl ether and the resultant solid was isolated and dried under vacuum at 55° C. There was thus obtained the title compound (0.038 g); NMR Spectrum: (DMSOd$_6$) 2.19 (s, 3H), 3.27 (s, 3H), 3.66 (s, 2H), 4.17 (m, 2H), 7.04 (d, 2H), 7.24 (d, 1H), 7.57 (d, 1H), 7.82 (s, 1H), 7.96 (m, 4H), 8.1 (d, 2H), 9.71 (s, 1H), 10.44 (s, 1H); Mass Spectrum: M–H$^-$ 428.

The N-[5-(4-cyanobenzamido)-2-methylphenyl]-4-hydroxybenzamide used as a starting material was obtained as follows:

Triethylamine (23 ml) was added to a suspension of 3-nitro-4-methylaniline (10 g), 4-cyanobenzoyl chloride (13.1 g), 4-dimethylaminopyridine (0.8 g) in methylene chloride (200 ml) which had been cooled to 0° C. The reaction mixture was allowed to warm to ambient temperature and was stirred for 5 hours. The mixture was partitioned between methylene chloride and 0.5N hydrochloric acid solution. The organic phase was dried (MgSO$_4$) and evaporated and the residue was triturated under isohexane. The solid was isolated and dried under vacuum at 55° C. There was thus obtained N-(3-nitro-4-methylphenyl)-4-cyanobenzamide (18.3 g); NMR Spectrum: (DMSOd$_6$) 2.5 (s, 3H), 7.49 (d, 1H), 7.96 (m, 1H), 8.05 (d, 2H), 8.12 (d, 2H), 8.51 (d, 1H), 10.77 (s, 1H).

A solution of tin(II) chloride dihydrate (15.4 g) in concentrated hydrochloric acid (80 ml) was added to a suspension of N-(3-nitro-4-methylphenyl)-4-cyanobenzamide (6.39 g) in acetic acid (120 ml). The mixture was stirred and heated to reflux for 2 hours. The mixture was allowed to cool to ambient temperature and was basified by the addition of 2N sodium hydroxide solution. The precipitated solid was isolated and dried under vacuum at 55° C. to give N-(3-amino-4-methylphenyl)-4-cyanobenzamide (5.62 g); NMR Spectrum: (DMSOd$_6$) 2.01 (s, 3H), 4.85 (s, 2H), 6.8 (d, 1H), 6.86 (d, 1H), 7.11 (s, 1H), 7.96 (d, 2H), 8.06 (d, 2H), 10.11 (s, 1H).

Oxalyl chloride (0.31 ml) was added dropwise to a solution of 4-acetoxybenzoic acid (0.54 g) and DMF (a few drops) in methylene chloride (25 ml) which had been cooled to 0° C. The mixture was allowed to warm to ambient temperature and was stirred for 4 hours. The mixture was evaporated and the residue was dissolved in methylene chloride (20 ml). A mixture of N-(3-amino-4-methylphenyl)-4-cyanobenzamide (0.5 g), triethylamine (0.7 ml) and 4-dimethylaminopyridine (0.024 g) in methylene chloride (5 ml) was added and the reaction mixture was stirred at ambient temperature overnight. The mixture was evaporated and the residue was triturated under 2N hydrochloric acid solution. The precipitated solid was isolated, washed with a saturated aqueous solution of sodium bicarbonate and with water and dried under vacuum at 55° C. There was thus obtained N-[5-(4-cyanobenzamido)-2-methylphenyl]-4-acetoxybenzamide (0.443 g); NMR Spectrum: (DMSOd$_6$) 2.18 (s, 3H), 2.26 (s, 3H), 7.25 (m, 3H), 7.57 (d, 1H), 7.84 (s, 1H), 8.0 (m, 4H), 8.11 (d, 2H), 9.91 (s, 1H), 10.46 (s, 1H).

A mixture of the material so obtained, sodium methoxide (0.113 g) and methanol (20 ml) was stirred at ambient temperature for 4 hours. The mixture was concentrated to approximately 5 ml by evaporation under reduced pressure and acidified by the addition of 2N hydrochloric acid. The resultant solid was washed with water and dried under vacuum at 55° C. to give N-[5-(4-cyanobenzamido)-2-methylphenyl]-4-hydroxybenzamide (0.32 g); NMR Spectrum: (DMSOd$_6$) 2.18 (s, 3H), 6.84 (d, 2H), 7.22 (d, 1H), 7.57 (d, 1H), 7.83 (m, 3H), 7.98 (d, 2H), 8.1 (d, 2H), 10.13 (s, 1H), 10.43 (s, 1H); Mass Spectrum: M–H$^-$ 370.

EXAMPLE 9

N-[5-(4-cyanobenzamido)-2-methylphenyl]-4-(methoxycarbonylmethoxy)benzamide

Methyl bromoacetate (0.023 ml) was added to a suspension of N-[5-(4-cyanobenzamido)-2-methylphenyl]-4-hydroxybenzamide (0.06 g) and potassium carbonate (0.045 g) in DMF (3 ml) and the mixture was stirred and heated to 80° C. for 5 hours. The mixture was poured into water and extracted with ethyl acetate. The organic extract was dried (MgSO$_4$) and evaporated. The residue was triturated under diethyl ether. The resultant solid was dried under vacuum at 55° C. to give the title compound as a solid (0.024 g); NMR Spectrum: (DMSOd$_6$) 2.2 (s, 3H), 3.71 (s, 3H), 4.9 (s, 2H), 7.05 (d, 2H), 7.23 (d, 1H), 7.56 (d, 1H), 7.81 (s, 1H), 7.97 (m, 4H), 8.1 (d, 2H), 9.75 (s, 1H), 10.44 (s, 1H).

EXAMPLE 10

N-[5-(4-cyanobenzamido)-2-methylphenyl]-4-(chloromethyl)benzamide

Triethylamine (0.55 ml) was added to a suspension of N-(3-amino-4-methylphenyl)-4-cyanobenzamide (0.40 g), 4-(chloromethyl)benzoyl chloride (0.45 g) and 4-dimethylaminopyridine (0.019 g) in methylene chloride (12 ml) and the mixture was stirred at ambient temperature for 16 hours. The mixture was evaporated and the residue was triturated with water. The resultant solid was isolated and washed in turn with 2N hydrochloric acid and a saturated aqueous sodium bicarbonate solution. The solid was dried under vacuum at 55° C. to give the required starting material (0.64 g); NMR Spectrum: (DMSOd$_6$) 2.2 (s, 3H), 4.82 (s, 2H), 7.23 (d, 1H), 7.58 (m, 3H), 7.84 (s, 1H), 7.99 (m, 4H), 8.1 (d, 2H), 9.91 (s, 1H), 10.46 (s, 1H); Mass Spectrum: M-H$^-$ 402.

EXAMPLE 11

N-[5-(4cyanobenzamido)-2-methylphenyl]-3-(chloromethyl)benzamide

Using an analogous procedure to that described in Example 10, N-(3-amino-4-methylphenyl)-4-cyanobenzamide was reacted with 3-(chloromethyl)benzoyl chloride to give the title compound as a solid (0.267 g); NMR Spectrum: (DMSOd$_6$) 2.2 (s, 3H), 4.84 (s, 2H), 7.25 (d, 1H), 7.55 (m, 2H), 7.64 (m, 1H), 7.83 (s, 1H), 7.99 (m, 4H), 8.1 (d, 2H), 9.97 (s, 1H), 10.46 (s, 1H); Mass Spectrum: M-H$^-$ 402.

EXAMPLE 12

N-[5-(4-cyanobenzamido)-2-methylphenyl]-4-(diethylaminomethyl)benzamide

Diethylamine hydrochloride (0.024 g) was added to a stirred mixture of N-[5-(4-cyanobenzamido)-2-methylphenyl]-4-(chloromethyl)benzamide (0.06 g), potassium carbonate (0.082 g) and acetone (5 ml) and the reaction mixture was stirred and heated to 55° C. for 16 hours. Further portions of diethylamine hydrochloride and potassium carbonate (same quanities as before) were added and the mixture was heated to 55° C. for a further 4 days. The reaction mixture was evaporated and the residue was triturated with water. The solid was isolated and dried under vacuum at 55° C. to give the title compound as a solid (0.044 g); NMR Spectrum: (CDCl$_3$) 1.06 (t, 6H), 2.28 (s, 3H), 2.53 (m, 4H), 3.63 (s, 2H), 7.2 (d, 1H), 7.5 (d, 2H), 7.74 (m, 4H), 7.81 (d, 2H), 7.97 (d, 2H), 8.15 (s, 1H), 8.27 (s, 1H); Mass Spectrum: M-H$^-$ 439.

EXAMPLE 13

N-[5-(4-cyanobenzamido)-2-methylphenyl]-4-(2-methoxyethylaminomethyl)benzamide

2-Methoxyethylamine (0.019 ml) was added to a stirred solution of N-[5-(4-cyanobenzamido)-2-methylphenyl]-4-(chloromethyl)benzamide (0.060 g) and potassium carbonate (0.041 g) in acetone (5 ml) and the reaction mixture was heated to 55° C. overnight. Further portions of 2-methoxyethylamine and potassium carbonate (same quantities as before) were added and the reaction mixture was stirred at 55° C. for a further 4 days. The reaction mixture was evaporated and the residue was triturated with water. The resultant solid was isolated and dried under vacuum at 55° C. to give the title compound as a solid (0.039 g, 59%); NMR Spectrum: (CDCl$_3$) 2.27 (s, 3H), 2.83 (m, 2H), 3.37 (m, 4H), 3.56 (t, 2H), 3.91 (s, 2H), 7.19 (d, 1H), 7.49 (d, 2H), 7.77 (m, 7H), 7.95 (d, 2H), 8.13 (s, 1H), 8.3 (s, 1H); Mass Spectrum: M-H$^-$ 441.

EXAMPLE 14

N-[5-(4-cyanobenzamido)-2-methylphenyl]-4-(2-ethoxyethoxy)benzamide

Phosphoryl chloride (0.03 ml) was added dropwise to a stirred mixture of N-(3-amino-4-chlorophenyl)-4-cyanobenzamide (0.08 g), 4-(2-ethoxyethoxy)benzoic acid (J. Org. Chem., 1973, 38, 3160; 0.062 g) and pyridine (4 ml) which had been cooled to −15° C. The reaction mixture was stirred at −15° C. for 3 hours and then allowed to warm to ambient temperature. The mixture was stirred for 48 hours. The reaction mixture was diluted with water and stirred overnight. The precipitate was isolated, washed with diethyl ether and dried under vacuum at 55° C. to give the title compound (0.024 g); NMR Spectrum: (DMSOd$_6$) 1.15 (t, 3H), 3.49 (m, 2H), 3.73 (m, 2H), 4.19 (m, 2H), 9.86 (s, 1H), 10.62 (s, 1H); Mass Spectrum: M-H$^-$ 462.

EXAMPLE 15

N-[2-chloro-5-(4-cyanobenzamido)phenyl]-4-[2-(imidazol-1-yl)ethoxy]benzamide

Using an analogous procedure to that described in Example 14, N-(3-amino-4-chlorophenyl)-4-cyanobenzamide was reacted with 4-[2-(imidazol-1-yl)ethoxy]benzoic acid (J. Med. Chem., 1985, 28, 1427) to give the title compound in 75% yield; NMR Spectrum: (DMSOd$_6$) 4.48 (t, 2H), 4.65 (m, 2H), 7.09 (d, 1H), 7.51 (d, 1H), 7.68 (m, 3H), 7.82 (s, 1H), 8.0 (m, 4H), 8.1 (m, 2H), 8.73 (d, 1H), 9.18 (s, 1H), 9.89 (s, 1H), 10.66 (s, 1H); Mass Spectrum: M-H$^-$ 484.

The N-(3-amino-4-chlorophenyl)-4-cyanobenzamide used as a starting material was obtained as follows:

4-Cyanobenzoyl chloride (11.92 g) was added slowly to a stirred solution of 4-chloro-3-nitroaniline (10.4 g) in pyridine (20 ml) and the mixture was stirred and heated to 115° C. for 18 hours. The mixture was cooled to ambient temperature and poured into water (150 ml) and stirred for 30 minutes. The resultant precipitate was isolated, washed with water and dried to give N-(4-chloro-3-nitrophenyl)-4-cyanobenzamide (18 g), m.p. 213° C.; NMR Spectrum: (DMSOd$_6$) 7.78 (d, 1H), 8.05 (m, 3H), 8.1 (d, 2H), 8.58 (s, 1H), 10.93 (s, 1H).

A portion (3.6 g) of the material so obtained was added to a stirred suspension of iron powder (10 g) in a mixture of ethanol (130 ml), water (30 ml) and glacial acetic acid (4 ml). The mixture was heated to 75° C. for 1 hour and thereafter, whilst hot, basified by the addition of sodium carbonate. The mixture was filtered and the filtrate was evaporated. The resultant solid was stirred in water for 3 hours. The solid was isolated and dried to give the required starting material (2.7 g), m.p. 237.7° C.; NMR Spectrum: (DMSOd$_6$) 5.44 (s, 2H), 6.98 (m, 1H), 7.21 (d, 1H), 7.42 (d, 1H), 8.07 (d, 2H), 8.14 (d, 2H), 10.36 (s, 1H).

EXAMPLE 16

N-[5-(3-dimethyaminobenzamido)-2-methylphenyl]-4-(2-ethoxyethoxy)benzamide

Oxalyl chloride (0.087 ml) was added dropwise to a stirred solution of 4-(2-ethoxyethoxy)benzoic acid (J. Org. Chem., 1973, 38, 3160; 0.21 g) and DMF (a few drops) which had been cooled to 0° C. The mixture was allowed to warm to ambient temperature and was stirred for five hours. The resultant solution was evaporated to dryness and the residue was dissolved in methylene chloride (10 ml). N-(3-Amino-4-methylphenyl)-3-dimethylaminobenzamide (0.135 g) and triethylamine (0.189 ml) were added in turn and the mixture was stirred at ambient temperature for 16 hours. The resultant solution was washed with a saturated aqueous solution of sodium bicarbonate and with brine, dried (MgSO$_4$) and evaporated. The residue was triturated under a mixture of ethyl acetate and diethyl ether. The resulting solid was isolated and dried under vacuum at 40° C. to give the title compound (0.164 g); NMR Spectrum: (DMSOd$_6$) 1.1 (m, 3H), 2.18 (s, 3H), 2.97 (s, 6H), 3.5 (m, 2H), 3.7 (m, 2H), 4.16 (m, 2H), 7.02 (m, 3H), 7.2 (d, 1H), 7.34 (m, 3H), 7.59 (d, 1H), 7.79 (s, 1H), 7.95 (d, 2H), 9.74 (s, 1H), 10.12 (s, 1H); Mass Spectrum: M+H$^+$ 462.

EXAMPLE 17

N-[2-chloro-5-(4-cyanobenzamido)phenyl]-3-(1-methylpiperidin-4-yloxy)benzamide

Oxalyl chloride (0.11 ml) was added to a stirred suspension of 3-(1-methylpiperidin-4-yloxy)benzoic acid (0.246 g) in methylene chloride (10 ml) which had been cooled to 0° C. DMF (1 drop) was added and the mixture was stirred for 16 hours and allowed to warm to ambient temperature. The solvent was evaporated to give an orange coloured solid. The acid chloride so obtained was added to a mixture of N-(3-amino-4-chlorophenyl)-4-cyanobenzamide (0.255 g) and pyridine (3 ml) and the reaction mixture was stirred and heated to 100° C. for 12 hours. After cooling, the pyridine was evaporated and water (25 ml) added. The aqueous phase was extracted with ethyl acetate and the organic phase was dried (MgSO$_4$) and evaporated. The residual oil was purified by column chromatography on silica gel using a 9:1 mixture of ethyl acetate and methanol as eluent. There was thus obtained the title compound as a solid (0.031 g), m.p. 177–179° C.; Mass Spectrum: M+H$^+$ 489.

The 3-(1-methylpiperidin-4-yloxy)benzoic acid starting material was prepared as follows:

Diethyl azodicarboxylate (2.3 ml) was added dropwise to a stirred suspension of triphenylphosphine (3.9 g), ethyl 3-hydroxybenzoate (2.3 g) and 4-hydroxy-1-methylpiperidine (1.15 g) in THF (40 ml) which had been cooled to 5° C. The mixture was allowed to warm to ambient temperature and stirred for 18 hours. The solvent was evaporated and the residue was dissolved in ethyl acetate. The organic phase was extracted with 2N hydrochloric acid. The aqueous extract was washed with ethyl acetate, basified with potassium carbonate and extracted with ethyl acetate. The resultant organic phase was dried (MgSO$_4$) and evaporated. The residue was purified by column chromatography on silica gel using a 49:1 mixture of methylene chloride and methanol as eluent. There was thus obtained ethyl 3-(1-methylpiperidin-4-yloxy)benzoate (0.552 g) as an oil; NMR Spectrum: (DMSOd$_6$) 1.33 (t, 3H), 1.78 (m, 2H), 1.95 (m, 2H), 2.23 (m, 5H), 2.62 (m, 2H), 4.32 (m, 3H), 7.02 (m, 1H), 7.24 (t, 1H), 7.52 (d, 1H), 7.55 (d, 1H).

The material so obtained was dissolved in a mixture of ethanol (5 ml) and water (0.5 ml) containing sodium hydroxide (0.16 g). The mixture was stirred and heated to 50° C. for 1 hour and then stored at ambient temperature for 18 hours. The mixture was evaporated. A 1N hydrochloric acid solution (4 ml) was added and the mixture was re-evaporated. The residue was washed with methylene chloride and dried. There was thus obtained 3-(1-methylpiperidin-4-yloxy) benzoic acid (0.265 g) as a solid; NMR Spectrum: (DMSOd$_6$) 1.7 (m, 2H), 1.96 (m, 2H), 2.34 (s, 3H), 2.46 (m, 2H), 7.17 (m, 1H), 7.37 (t, 1H), 7.42 (d, 1H), 7.5 (d, 1H).

EXAMPLE 18

N-[5-(3-carboxymethoxybenzamido)-2-methylphenyl]-3,4-dimethoxybenzamide

Trifluoroacetic acid (5 ml) was added to a stirred solution of N-[5-(3-tert-butoxycarbonylmethoxybenzamido)-2-methylphenyl]-3,4-dimethoxybenzamide (0.455 g) in methylene chloride (5 ml) and the mixture was stirred at ambient temperature for 1 hour. The mixture was evaporated and the residue was azeotroped with toluene. The resultant solid was dried under vacuum at 60° C. There was thus obtained the title compound (0.375 g), m.p. 206–207° C.; NMR Spectrum: (DMSOd$_6$) 2.18 (s, 3H), 3.83 (s, 6H), 4.74 (s, 2H), 7.06 (d, 1H), 7.11 (m, 1H), 7.23 (d, 1H), 7.43 (t, 1H), 7.48 (d, 1H), 7.55 (br m, 1H), 7.63 (m, 1H), 7.8 (d, 1H), 9.75 (br s, 1H), 10.17 (br s, 1H); Mass Spectrum: M+H$^+$ 465.

EXAMPLE 19

N-{5-[4-(3-hydroxypropoxy)benzamido]-2-methylphenyl}-3,4-dimethoxybenzamide

S,S-Dioxothiamorpholine trifluoroacetic acid salt (0.22 g) was added to a stirred mixture of N-{5-[4-(3-chloropropoxy) benzamido]-2-methylphenyl}-3,4-dimethoxybenzamide (0.5 g), tetra-n-butylammonium iodide (0.096 g), di-isopropylethylamine (0.29 g) and DMA (4 ml) and the mixture was stirred and heated to 100° C. for 1 week. The reaction mixture was allowed to cool to ambient temperature and poured into water (100 ml). The resultant precipitate was isolated and washed with water and with diethyl ether. The solid so obtained was purified by column chromatography on silica gel using increasingly polar mixtures of methylene chloride and methanol as eluent. There were thus obtained in turn:

(a) a foam which was dried under vacuum at 60° C. to give the title compound (0.146 g); NMR Spectrum: (DMSOd$_6$+CD$_3$CO$_2$D) 1.86 (m, 2H), 2.19 (s, 3H), 3.55 (t, 2H), 3.82 (s, 6H), 4.11 (t, 2H), 7.03 (d, 2H), 7.06 (d, 1H), 7.2 (d, 1H), 7.56 (m, 2H), 7.62 (m, 1H), 7.79 (d, 1H), 7.94 (d, 2H), 9.75 (br s, 1H), 10.03 (br s, 1H); Mass Spectrum: M+H$^+$ 465; Elemental Analysis: Found C, 66.3; H, 5.9; N, 6.0; C$_{26}$H$_{28}$N$_2$O$_6$ 0.5H$_2$O requires C, 66.0; H, 6.1; N, 5.9%; and (b) a glassy brown solid which was dried under vacuum at 60° C. to give N-{5-[4-(3-(S,S-dioxothiamorpholin-1-yl)propoxy)benzamido]-2-methylphenyl}-3,4-dimethoxybenzamide (0.057 g); NMR Spectrum: (DMSOd$_6$) 1.86 (m, 2H), 2.17 (s, 3H), 2.62 (t, 2H), 2.88 (m, 4H), 3.05 (m, 4H), 3.83 (s, 6H), 4.09 (t, 2H), 7.03 (d, 2H), 7.06 (d, 1H), 7.21 (d, 1H), 7.54 (m, 2H), 7.62 (m, 1H), 7.8 (d, 1H), 7.93 (d, 2H), 9.73 (br s, 1H), 10.03 (br s, 1H); Mass Spectrum: M+H$^+$ 582.

EXAMPLE 20

N-{5-[4-(N-(3-dimethylaminopropyl)-N-methylamino)benzamido]-2-methylphenyl}-3,4-dimethoxybenzamide N-(3-Dimethylaminopropyl)-N-methylamine (0.325 g) was added to a stirred mixture of N-[5-(4-fluorobenzamido)-2-methylphenyl]-3,4-dimethoxybenzamide (0.38 g), potassium carbonate (0.39 g) and DMSO (5 ml). The mixture was stirred and heated to 130° C. for 10 days. The mixture was allowed to cool to ambient temperature and partitioned between ethyl acetate and water. The organic phase was washed with water, dried (MgSO$_4$) and evaporated to give an oil which was purified by column chromatography on silica gel using increasingly polar mixtures of methylene chloride and methanol as eluent. The material so obtained was triturated under diethyl ether and the resultant solid was dried under vacuum at 60° C. There was thus obtained the title compound (0.16 g), m.p. 164–165° C.; NMR Spectrum:

(DMSOd$_6$) 1.6 (m, 2H), 2.16 (s, 3H), 2.2 (s, 6H), 2.3 (t, 2H), 2.94 (s, 3H), 3.4 (t, 2H), 3.83 (s, 6H), 6.72 (d, 2H), 7.06 (d, 1H), 7.18 (d, 1H), 7.55 (m, 2H), 7.63 (m, 1H), 7.79 (d, 2H), 7.84 (d, 2H), 9.71 (br s, 1H), 9.8 (br s, 1H); Mass Spectrum: M+H$^+$ 505; Elemental Analysis: Found C, 65.9; H, 7.0; N, 10.4; $C_{29}H_{36}N_4O_4$ 1.3H$_2$O requires C, 66.0; H, 7.4; N, 10.6%.

The N-[5-(4-fluorobenzamido)-2-methylphenyl]-3,4-dimethoxybenzamide used as a starting material was obtained as follows:

Using an analogous procedure to that described in Example 3, N-(5-amino-2-methylphenyl)-3,4-dimethoxybenzamide was reacted with 4-fluorobenzoyl chloride. There was thus obtained the required starting material, m.p. 210–211 °C.; NMR Spectrum: (DMSOd$_6$) 2.18 (s, 3H), 3.83 (s, 6H), 7.07 (d, 1H), 7.23 (d, 1H), 7.35 (t, 2H), 7.55 (m, 2H), 7.57 (d, 1H), 7.63 (m, 1H), 7.8 (d, 1H), 8.03 (m, 2H), 9.75 (br s, 1H), 10.39 (br s, 1H).

EXAMPLE 21

N-[5-(3-chloromethylbenzamido)-2-methylphenyl]-3,4-dimethoxybenzamide

Using an analogous procedure to that described in Example 2, N-(5-amino-2-methylphenyl)-3,4-dimethoxybenzamide was reacted with 3-(chloromethyl) benzoyl chloride to give the title compound in 87% yield; NMR Spectrum: (DMSOd$_6$) 2.19 (s, 3H), 3.82 (s, 6H), 4.84 (s, 2H), 7.06 (d, 1H), 7.23 (d, 1H), 7.57 (m, 5H), 7.80 (s, 1H), 7.9 (d, 1H), 8.0 (s, 1H), 9.76 (s, 1H), 10.26 (s, 1H); Mass Spectrum: M+H$^+$ 439.

EXAMPLE 22

N-[2-Methyl-5-(3-trifluoromethylbenzamido) phenyl]-4-(2-ethoxyethoxy)benzamide

A solution of N-(5-amino-2-methylphenyl)-4-(2-ethoxyethoxy)benzamide (0.141 g) and triethylamine (0.121 g) in methylene chloride (5 ml) was added to 3-trifluoromethylbenzoyl chloride (0.104 g) and the resultant mixture was stirred at ambient temperature for 18 hours. The mixture was washed in turn with a 1M aqueous citric acid solution, a saturated aqueous sodium bicarbonate solution and water. The organic solution was evaporated and the residue was triturated under a mixture of diethyl ether and ethyl acetate. The resultant solid was isolated and dried under vacuum. There was thus obtained the title compound (weight 0.042 g); Mass Spectrum: M+H$^+$ 487.

The N-(5-amino-2-methylphenyl)-4-(2-ethoxyethoxy) benzamide used as a starting material was obtained as follows:

Oxalyl chloride (2.7 ml) was added to a mixture of 4-(2-ethoxyethoxy)benzoic acid (5.25 g) and DMF (1 ml) in methylene chloride (100 ml) and the reaction mixture was stirred at ambient temperature for 4 hours. The mixture was evaporated and the residue was dissolved in methylene chloride (100 ml). 2-Methyl-5-nitroaniline (3.17 g), 4-dimethylaminopyridine (0.254 g) and triethylamine (7.3 ml) were added in turn and the resultant reaction mixture was stirred at ambient temperature for 16 hours. The mixture was evaporated and the residue was partitioned between ethyl acetate and water. The organic phase was dried and evaporated to give N-(2-methyl-5-nitrophenyl)-4-(2-ethoxyethoxy)benzamide as an oil which was used without further purification.

10% Palladium-on-carbon catalyst (0.72 g) was added to a solution of the material so obtained in methanol (300 ml). Ammonium formate (13.1 g) was added and the reaction mixture was stirred and heated to reflux for 1.75 hours. The mixture was filtered and the filtrate was evaporated. The residue was triturated under water and the resultant solid was isolated and dried under vacuum at 55° C. The solid so obtained was dissolved in the minimum amount of hot methanol and precipitated by the addition of water. There was thus obtained the required starting material as a solid (4.33 g); Mass Spectrum: M+H$^+$ 278.

EXAMPLE 23

Using an analogous procedure to that described in Example 22, the appropriate benzoyl chloride was reacted with N-(5-amino-2-methylphenyl)benzamide to give the compounds described in Table III.

TABLE III

| No. | $(R^1)_m$ | R | Note |
|---|---|---|---|
| 1 | 4-(2-ethoxyethoxy) | hydrogen | a |
| 2 | 4-(2-ethoxyethoxy) | 2-fluoro | b |
| 3 | 4-(2-ethoxyethoxy) | 4-chloro | c |
| 4 | 4-(2-ethoxyethoxy) | 3,4-chloro | d |
| 5 | 4-(2-ethoxyethoxy) | 4-cyano | e |
| 6 | 4-(2-ethoxyethoxy) | 2-methoxy | f |
| 7 | 4-(2-ethoxyethoxy) | 3-ethoxy | g |
| 8 | 4-(2-ethoxyethoxy) | 4-ethyl | h |
| 9 | 4-(2-ethoxyethoxy) | 4-propyl | i |
| 10 | 4-diethylaminomethyl | hydrogen | j |
| 11 | 4-diethylaminomethyl | 2-fluoro | k |
| 12 | 4-diethylaminomethyl | 4-fluoro | l |
| 13 | 4-diethylaminomethyl | 3-chloro | m |
| 14 | 4-diethylaminomethyl | 2,4-dichloro | n |
| 15 | 4-diethylaminomethyl | 3,4-dichloro | o |
| 16 | 4-diethylaminomethyl | 3-trifluoromethyl | p |
| 17 | 4-diethylaminomethyl | 4-methoxycarbonyl | q |
| 18 | 4-diethylaminomethyl | 3-cyano | r |
| 19 | 4-diethylaminomethyl | 4-methoxy | s |
| 20 | 4-diethylaminomethyl | 3-ethoxy | t |
| 21 | 4-diethylaminomethyl | 3,4-dimethoxy | u |
| 22 | 4-diethylaminomethyl | 3-morpholino | v |
| 23 | 4-diethylaminomethyl | 3-trifluoromethoxy | w |
| 24 | 4-diethylaminomethyl | 3-phenoxy | x |
| 25 | 4-diethylaminomethyl | 3-bromo | y |
| 26 | 3-(4-methylpiperazin-1-ylmethyl) | 3-trifluoromethoxy | z |
| 27 | 3-(4-methylpiperazin-1-ylmethyl) | 4-trifluoromethoxy | aa |
| 28 | 3-(4-methylpiperazin-1-ylmethyl) | 3-phenoxy | bb |

Notes
a The product gave the following data: Mass M + H 419.
b The product gave the following data: Mass M + H 437.
c The product gave the following data: Mass M + H 453.
d The product gave the following data: Mass M + H 487.
e The product gave the following data: Mass M + H 444.
f The product gave the following data: Mass M + H 449.
g The product gave the following data: Mass M + H 464.
h The product gave the following data: Mass M + H 447.
i The product gave the following data: Mass M + H 461.
j The step of washing the reaction mixture with a 1M aqueous citric acid solution was omitted. The product gave the following data: Mass M + H 416.

The N-(5-amino-2-methylphenyl)-4-diethylaminomethylbenzamide used as a starting material was prepared as follows:

4-Chloromethylbenzoyl chloride (21.4 g) was added to a stirred mixture of 2-methyl-5-nitroaniline (26.6 g), triethylamine (31.5 ml) and methylene chloride (600 ml) and the resultant mixture was stirred at ambient temperature for 16 hours. The precipitate was isolated, washed in turn with 1N aqueous hydrochloric acid solution and with diethyl ether and dried under vacuum at 40° C. There was thus obtained N-(2-methyl-5-nitrophenyl)-4-chloromethylbenzamide (18 g); NMR (DMSOd$_6$) 2.38 (s, 3H), 4.83 (s, 2H), 7.54–7.61 (m, 3H), 7.98–8.02 (m, 3H), 8.34 (s, 1H), 10.15 (s, 1H); Mass M+H 305.

Diethylammonium chloride (64.2 g) was added to a stirred suspension of the material so obtained and potassium carbonate (18.2 g) in acetone (750 ml). The mixture was stirred and heated to 54° C. for 16 hours. The resultant mixture was evaporated and the residue was dissolved in methylene chloride. The organic solution was washed with water and evaporated. The resultant solid was isolated and dried under vacuum at 40° C. There was thus obtained N-(2-methyl-5-nitrophenyl)-4-diethylaminomethylbenzamide (18.1 g); NMR (DMSOd$_6$) 0.97 (t, 6H), 2.36 (s, 3H), 2.44–2.49 (m, 4H), 3.58 (s, 2H), 7.43 (d, 2H), 7.51 (d, 1H), 7.94 (s, 3H), 8.38 (s, 1H); Mass M+H 342.

Iron powder (29.5 g) was added to a stirred suspension of the material so obtained in ethanol (500 ml), water (50 ml) and acetic acid (10 ml). The mixture was heated to reflux and stirred for 5 hours. Water (50 ml) was added and the mixture was basified by the addition of sodium carbonate. The mixture was filtered and the filtrate was evaporated. The residue was triturated under water. The resultant solid was isolated, washed with diethyl ether and dried under vacuum at 40° C. There was thus obtained the required starting material (18 g); NMR (DMSOd$_6$) 0.97 (t, 6H), 2.02 (s, 3H), 2.44–2.49 (m, 4H), 3.56 (s, 2H), 6.37 (d, 1H), 7.59 (s, 1H), 6.85 (d, 1H), 7.41 (d, 2H), 7.87 (d, 2H), 9.53 (s, 1H); Mass M+H 312.

k) The step of washing the reaction mixture with a 1M aqueous citric acid solution was omitted. The product gave the following data: Mass M+H 434.

l) The step of washing the reaction mixture with a 1M aqueous citric acid solution was omitted. The product gave the following data: Mass M+H 434.

m) The step of washing the reaction mixture with a 1M aqueous citric acid solution was omitted. The product gave the following data: Mass M+H 450.

n) The step of washing the reaction mixture with a 1M aqueous citric acid solution was omitted. The product gave the following data: Mass M+H 485.

o) The step of washing the reaction mixture with a 1M aqueous citric acid solution was omitted. The product gave the following data: Mass M+H 485.

p) The step of washing the reaction mixture with a 1M aqueous citric acid solution was omitted. The product gave the following data: Mass M+H 484.

q) The step of washing the reaction mixture with a 1M aqueous citric acid solution was omitted. The product gave the following data: Mass M+H 474.

r) The step of washing the reaction mixture with a 1M aqueous citric acid solution was omitted. The product gave the following data: Mass M+H 441.

s) The step of washing the reaction mixture with a 1M aqueous citric acid solution was omitted. The product gave the following data: Mass M+H 446.

t) The step of washing the reaction mixture with a 1M aqueous citric acid solution was omitted. The product gave the following data: Mass M+H 460.

u) The step of washing the reaction mixture with a 1M aqueous citric acid solution was omitted. The product gave the following data: Mass M+H 476.

v) The step of washing the reaction mixture with a 1M aqueous citric acid solution was omitted. Trituration of the reaction product did not provide a solid. The organic mixture was evaporated and the residue was purified by column chromatography on an ion exchange column (isolute SCX column from International Sorbent Technology Limited, Hengoed, Mid-Glamorgan, UK) using a 99:1 mixture of methanol and a saturated aqueous ammonium hydroxide solution as eluent. The product gave the following data: NMR: (DMSOd$_6$) 1.0 (t, 6H), 2.19 (s, 3H), 2.44–2.49 (m, 4H), 3.15–3.18 (m, 4H), 3.58 (s, 2H), 3.70–3.76 (m, 4H), 7.08–7.15 (m, 1H), 7.2 (d, 1H), 7.32–7.38 (m, 2H), 7.44–7.48 (m, 3H), 7.53–7.6 (m, 1H), 7.90–7.94 (m, 2H), 9.82 (s, 1H), 10.11 (s, 1H); Mass: M+H 501.

w) The product was deposited as a precipitate during the 18 hour reaction period. The precipitate was isolated and washed with methylene chloride. The product gave the following data: Mass M+H 500.

x) The step of washing the reaction mixture with a 1M aqueous citric acid solution was omitted. The product gave the following data: Mass M+H 508.

The 3-phenoxybenzoyl chloride used as a starting material was prepared as follows:

Oxalyl chloride (0.11 ml) was added dropwise to a stirred mixture of 3-phenoxybenzoic acid (0.214 g), DMF (a few drops) and methylene chloride (4 ml) which had been cooled to 0° C. The mixture was stirred at ambient temperature 24 hours. The solvent was evaporated to give the required acid chloride which was used without further purification.

y) The step of washing the reaction mixture with a 1M aqueous citric acid solution was omitted. The product gave the following data: Mass M+H 494.

z) The step of washing the reaction mixture with a 1M aqueous citric acid solution was omitted. The product gave the following data: Mass M+H 527.

The N-(5-amino-2-methylphenyl)-3-(4-methylpiperazin-1-ylmethyl)benzamide used as a starting material was prepared as follows:

3-Chloromethylbenzoyl chloride (24.8 ml) was added to a stirred mixture of 2-methyl-5-nitroaniline (26.6 g), triethylamine (49 ml) and methylene chloride (800 ml) and the mixture was stirred at ambient temperature for 16 hours. The precipitate was isolated, washed with 1N aqueous hydrochloric acid solution and with diethyl ether and dried under vacuum at 40° C. There was thus obtained 3-chloromethyl-N-(2-methyl-5-nitrophenyl)-benzamide (43.5 g); NMR (DMSOd$_6$) 2.38 (s, 3H), 2.85 (s, 2H), 7.53–7.58 (m, 2H), 7.67 (d, 1H), 7.95(d, 1H), 8.01–8.04 (m, 2H), 8.32 (s, 1H), 10.19 (s, 1 H); Mass M+H 305.

1-Methylpiperazine (8.03 ml) was added to a stirred mixture of a portion (20 g) of the material so obtained, potassium carbonate (18.2 g) and acetone (750 ml) and the mixture was heated to 54° C. and stirred for 16 hours. The resultant solution was evaporated and the residue was dissolved in methylene chloride. The organic solution was washed with water and evaporated. There was thus obtained N-(2-methyl-5-nitrophenyl)-3-(4-methylpiperazin-1-ylmethyl)benzamide (26.4 g); NMR (DMSOd$_6$) 2.06 (s, 3H), 2.12 (s, 3H), 2.31–2.37 (m, 8H), 3.52 (s, 2H), 7.48–7.57 (m, 3H), 7.87 (d, 2H), 8.01 (m, 1H), 8.33 (s, 1H); Mass M+H 369.

Iron powder was added to a stirred mixture of a portion (18.0 g) of the material so obtained, ethanol (500 ml), water (50 ml) and acetic acid (10 ml). The resultant mixture was stirred and heated to reflux for 5 hours. Water (50 ml) was added and the mixture was basified by the addition of sodium carbonate. The mixture was filtered and the filtrate was evaporated to dryness. The residue was triturated under water and the resultant solid was isolated and dried under vacuum at 40° C. There was thus obtained N-(5-amino-2-methylphenyl)-3-(4-methylpiperazin-1-ylmethyl)benzamide (11.1 g); NMR (DMSOd$_6$) 2.03 (s, 3H), 2.13 (s, 3H), 2.24–2.4 (m, 8H), 3.5 (s, 2H), 4.86 (s, 2H), 6.35 (d, 1H), 6.57 (s, 1H), 6.86 (d, 1H), 7.40–7.48 (m, 2H), 7.78–7.83 (m, 2H), 9.57 (s, 1H); Mass M+H 339.

aa) The step of washing the reaction mixture with a 1M aqueous citric acid solution was omitted. The product gave the following data: Mass M+H 527.

bb) The step of washing the reaction mixture with a 1M aqueous citric acid solution was omitted. The product gave the following data: Mass M+H 535.

EXAMPLE 24

N-[2-Methyl-5-(2-naphthoylamino)phenyl]-4-(2-ethoxyethoxy)benzamide

Using an analogous procedure to that described in Example 22, 2-naphthoyl chloride was reacted with N-(5-amino-2-methylphenyl)-4-(2-ethoxyethoxy)benzamide to give the title compound in 23% yield; Mass Spectrum: M+H 470.

EXAMPLE 25

N-[2-methyl-5-(3-morpholinobenzamido)phenyl]-3-piperidin-4-yloxybenzamide 1-(3-Dimethylaminopropyl)-3-ethylcarbodiimide hydrochloride (0.23 g) was added to a stirred mixture of 3-(1-tert-butoxycarbonylpiperidin-4-yloxy)benzoic acid (0.321 g), N-(3-amino-4-methylphenyl)-3-morpholinobenzamide (0.311 g), 1-hydroxybenzotriazole (0.202 g) and DMF (5 ml) which had been cooled to 0° C. The reaction mixture was allowed to come to ambient temperature and was stirred for 16 hours. The reaction mixture was partitioned between ethyl acetate and water. The organic phase was washed with water, and with a saturated aqueous sodium bicarbonate solution, dried (MgSO$_4$) and evaporated. There was thus obtained N-[2-methyl-5-(3-morpholinobenzamido)phenyl]-3-(1-tert-butoxycarbonylpiperidin-4-yloxy)benzamide (0.307 g); NMR Spectrum: (DMSOd$_6$) 1.36 (s, 9H), 1.53 (m, 2H), 1.92 (m, 2H), 2.16 (s, 3H), 3.18 (t, 4H), 3.22 (m, 2H), 3β(m, 2H), 3.75 (t, 4H), 4.62 (m, 1H), 7.18 (m, 3H), 7.37 (m, 2H), 7.41 (m, 2H), 7.52 (s, 1H), 7.58 (m, 2H), 7.78 (d, 1H), 9.84 (s, 1H), 10.13 (s, 1H); Mass Spectrum: M+H$^+$ 615.

Trifluoroacetic acid (0.80 ml) was added to a stirred solution of the material so obtained in methylene chloride (10 ml) which had been cooled to 0° C. The reaction mixture was stirred at ambient temperature for 18 hours. The mixture was evaporated and the residue was triturated under ethyl acetate to give the title compound, as its trifluoroacetate salt, (0.162 g); NMR Spectrum: (DMSOd$_6$) 1.9 (m, 2H), 2.12 (m, 2H), 2.19 (s, 3H), 3.05 (m, 2H), 3.15 (t, 4H), 3.5 (m, 2H), 3.78 (t, 4H), 4.78 (m, 1H), 7.12 (m, 1H), 7.21 (d, 2H), 7.38 (m, 4H), 7.57 (m, 3H), 7.8 (s, 1H), 9.02 (m, 2H), 9.9 (s, 1H), 10.15 (s, 1H); Mass Spectrum: M+H$^+$ 515.

The solid so obtained was dissolved in water (5 ml) and basified by the addition of potassium carbonate. The resultant precipitate was collected and dried under vacuum to give the title compound (0.07 g), m.p. 162–166° C.; Mass Spectrum: M+H$^+$ 515.

The 3-(1-tert-butoxycarbonylpiperidin-4-yloxy)benzoic acid used as a starting material was obtained as follows:

N-tert-Butoxycarbonyl-4-hydroxypiperidine was obtained from a commercial source, for example from Neosystem, F67100, Strasbourg, France, or was prepared by the following procedure. A solution of di-tert-butyl dicarbonate (53.9 g) in methylene chloride (100 ml) was added dropwise to a stirred mixture of 4-hydroxypiperidine (25 g), triethylamine (50 ml) and methylene chloride (250 ml) which had been cooled to 0° C. The resultant mixture was allowed to warm to ambient temperature and was stirred for 18 hours. The mixture was evaporated and the residue was purified by chromatography on silica a 2:1 mixture of isohexane and ethyl acetate as eluent. The oil so obtained was dried under vacuum at 60° C. to give N-tert-butoxycarbonyl-4-hydroxypiperidine as a white solid (49.1 g); NMR Spectrum: (DMSOd$_6$) 1.39 (s, 9H), 1.55 (m, 2H), 1.78 (m, 2H), 2.95 (m, 2H), 3.76 (m, 2H).

Diethyl azodicarboxylate (1.95 ml) was added dropwise over 5 minutes to a stirred mixture of N-tert-butoxycarbonyl-4-hydroxypiperidine (2 g), ethyl 3-hydroxybenzoate (1.66 g), triphenylphosphine (3.2 g) and THF (40 ml) which had been cooled to 0° C. The mixture was stirred at ambient temperature for 40 hours. The solvent was evaporated and the residue was triturated under a 9:1 mixture (40 ml) of isohexane and ethyl acetate. The mixture was filtered and the filtrate was evaporated. The residue was purified by column chromatography on silica using a 9:1 mixture (40 ml) of isohexane and ethyl acetate as eluent. There was thus obtained ethyl 3-(1-tert-butoxycarbonylpiperidin4-yloxy)benzoate as an oil (1.82 g); NMR Spectrum: (CDCl$_3$) 1.41 (t, 3H), 1.46 (s, 9H), 1.93 (m, 2H), 3.38 (m, 2H), 3.7 (m, 2H), 4.36 (q, 2H), 4.52 (m, 1H), 7.1 (m, 1H), 7.35 (t, 3H), 7.58 (s, 1H), 7.62 (d, 1H).

Sodium hydroxide solution (10M; 1.0 ml) was added to a solution in ethanol (10 ml) of the ester so obtained and the mixture was stirred at ambient temperature for 18 hours. The mixture was evaporated and the residue was dissolved in water (5 ml). A 1M aqueous hydrochloric acid solution (10 ml) and glacial acetic acid (1 ml) were added in turn and the mixture was extracted with methylene chloride. The organic phase was dried (MgSO$_4$) and evaporated to give the required starting material as a colourless solid (1.32 g), m.p. 148–150° C.; Mass Spectrum: M+H$^+$ 322.

EXAMPLE 26

N-{5-[3-(N-methylmethanesulphonylamino)benzamido]-2-methylphenyl}-3,4-dimethoxybenzamide A solution of N-[5-(3-methanesulphonylaminobenzamido)-2-methylphenyl]-3,4-dimethoxybenzamide (0.3 g) in DMF (5 ml) was added portionwise to a stirred mixture of sodium hydride (0.025 g) in DMF (5 ml). The resultant mixture was stirred at ambient temperature for 40 minutes. Methyl iodide (0.088 g) was added and the mixture was stirred at ambient temperature for 3 hours. The mixture was poured into water (150 ml). The resultant precipitate was isolated, washed in turn with water and diethyl ether and dried under vacuum at 60° C. There was thus obtained the title compound (0.18 g); m.p. 168–169° C.; NMR Spectrum: (DMSOd$_6$) 2.19 (s, 3H), 2.99 (s, 3H), 3.82 (s, 6H), 7.07 (d, 1H), 7.21 (d, 1H), 7.59 (m, 5H), 7.79 (s, 1H), 7.87 (d, 1H), 7.93 (s, 1H), 9.75 (br s, 1H), 10.25 (br s, 1H); Mass Spectrum: M+H$^+$ 498.

EXAMPLE 27

N-[5-(3-dimethylaminobenzamido)-2-methylphenyl]-3-methanesulphonylaminobenzamide Methanesulphonyl chloride (0.46 g) was added to a stirred mixture of N-[5-(3-dimethylaminobenzamido)-2- methylphenyl]-3-aminobenzamide, pyridine (0.56 ml) and methylene chloride (30 ml) and the resultant mixture was stirred at ambient temperature for 48 hours. The precipitate was isolated, washed in turn with methylene chloride and diethyl ether and dried under vacuum at 60° C. There was thus obtained the title compound (1.64 g); m.p. 239–240° C.; NMR Spectrum: (DMSOd$_6$) 2.19 (s, 3H), 3.03 (s, 9H), 7.24 (m, 2H), 7.45 (m, 5H), 7.59 (m, 1H), 7.71 (m, 1H), 7.27 (m, 1H), 7.77 (d, 1H), 7.82 (d, 1H), 9.94 (br s, 1H), 10.24 (br s, 1H); Mass Spectrum: M−H$^-$ 465.

The N-[5-(3-dimethylaminobenzamido)-2-methylphenyl]-3-aminobenzamide used as a starting material was prepared as follows:

3-Nitrobenzoyl chloride (1.52 g) was added to a mixture of N-(3-amino-4-methylphenyl)-3-dimethylaminobenzamide (2 g), pyridine (1.2 ml) and methylene chloride (40 ml) and the resultant mixture was stirred at ambient temperature for 96 hours. The precipitate was isolated, washed in turn with methylene chloride and diethyl ether and dried under vacuum at 60° C. There was thus obtained N-[5-(3-dimethylaminobenzamido)-2-methylphenyl]-3-nitrobenzamide (2.48 g); m.p. 219–220° C.; NMR Spectrum: (DMSOd$_6$) 2.2 (s, 3H), 2.95 (s, 6H), 6.92 (d, 1H), 7.23 (m, 3H), 7.28 (t, 1H), 7.58 (m, 1H), 7.83 (m, 2H), 8.43 (m, 2H), 8.8 (d, 1H), 10.12 (br s, 1H), 10.33 (br s, 1H); Mass Spectrum: M−H$^-$ 417.

10% Palladium-on-carbon (0.3 g) was added to a solution of the material so obtained in methanol (300 ml) and the mixture was stirred under an atmosphere of hydrogen. After cessation of hydrogen uptake, the catalyst was removed by filtration and the filtrate was evaporated. The residue was dried under vacuum at 60° C. There was thus obtained the required starting material (1.81 g); NMR Spectrum: (DMSOd$_6$) 2.18 (s, 3H), 2.95 (s, 6H), 5.26 (br s, 2H), 6.73 (m, 1H), 6.89 (m, 1H), 7.15 (m, 3H), 7.21 (m, 3H), 7.27 (m, 1H), 7.57 (m, 1H), 7.77 (d, 1H), 9.63 (br s, 1H), 10.07 (br s, 1H); Mass Spectrum: M+H$^+$ 390.

EXAMPLE 28

N-[5-(3-dimethylaminobenzamido)-2-methylphenyl]-3-(N-methylmethanesulphonylamino)benzamide Methyl iodide (0.1 g) was added to a mixture of N-[5-(3-dimethylaminobenzamido)-2-methylphenyl]-3-methanesulphonylaminobenzamide (0.3 g), caesium carbonate (0.23 g) and DMF (20 ml) and the resultant mixture was stirred at ambient temperature for 18 hours. The reaction mixture was poured into water (250 ml). The precipitate was isolated, washed in turn with water and diethyl ether and dried under vacuum at 60° C. There was thus obtained the title compound (0.23 g); m.p. 168–169° C.; NMR Spectrum: (DMSOd$_6$) 2.19 (s, 3H), 2.95 (s, 6H), 3.0 (s, 3H), 6.9 (d, 1H), 7.21 (m, 3H), 7.29 (t, 1H), 7.58 (m, 3H), 7.81 (d, 1H), 7.9 (d, 1H), 7.98 (d, 1H) 9.97 (br s, 1H), 10.09 (br s, 1 H); Mass Spectrum: M+H$^+$ 481.

EXAMPLE 29

N-[5-(3-dimethylaminobenzamido)-2-methylphenyl]-3-(2-hydroxy-3-piperidinopropoxy)benzamide Piperidine (3 g) was added to a stirred solution of N-[5-(3-dimethylaminobenzamido)-2-methylphenyl]-3-(2,3-epoxypropoxy)benzamide (0.19 g) in a mixture of methylene chloride (3 ml) and methanol (3 ml). The resultant solution was stirred at ambient temperature for 18 hours. The mixture was evaporated and the residue was purified by column chromatography on silica using increasingly polar mixtures of methylene chloride and methanol as eluent. There was thus obtained the title compound (0.19 g); NMR Spectrum: (DMSOd$_6$) 1.6 (m, 6H), 2.18 (s, 3H), 2.92 (m, 12H), 4.02 (m, 2H), 4.22 (m, 1H), 6.9 (m, 1H), 7.2 (m, 4H), 7.29 (t, 1H), 7.43 (t, 1H), 7.57 (m, 3H), 7.8 (d, 1H), 9.92 (br s, 1H), 10.12 (br s, 1H); Mass Spectrum: M+H$^+$ 531.

The N-[5-(3-dimethylaminobenzamido)-2-methylphenyl]-3-(2,3-epoxypropoxy)benzamide used as a starting material was prepared as follows:

1-Bromo-2,3-epoxypropane (2.64 g) was added to a stirred mixture of N-[5-(3-dimethylaminobenzamido)-2-methylphenyl]-3-hydroxybenzamide (1.5 g), caesium carbonate (3.14 g) and DMA (100 ml) and the resultant solution was stirred at ambient temperature for 18 hours. The mixture was poured into water (750 ml). The precipitate was isolated and washed in turn with water and diethyl ether. The material so obtained was dissolved in methylene chloride, dried (MgSO$_4$) and evaporated. The solid was dried under vacuum at 60° C. There was thus obtained the required starting material (1.55 g); NMR Spectrum: (DMSOd$_6$) 2.17 (s, 3H), 2.72 (m, 1H), 2.85 (m, 1H), 2.94 (s, 6H), 3.14 (m, 2H), 3.9 (m, 1H), 4.41 (m, 1H), 6.89 (d, 1H), 7.2 (m, 4H), 7.27 (t, 1H), 7.43 (t, 1H), 7.56 (m, 3H), 7.79 (d, 1H), 9.87 (br s, 1H), 10.09 (br s, 1H); Mass Spectrum: M−H$^-$ 444.

EXAMPLE 30

N-[5-(3-dimethylaminobenzamido)-2-methylphenyl]-3-(2-hydroxy-3-morpholinopropoxy)benzamide Using an analogous procedure to that described in Example 29, morpholine was reacted with N-[5-(3-dimethylaminobenzamido)-2-methylphenyl]-3-(2,3-epoxypropoxy)-benzamide to give the title compound in 64% yield; NMR Spectrum: (DMSOd$_6$) 2.2 (s, 3H), 2.44 (m, 4H), 2.94 (s, 6H), 3.15 (m, 1H), 3.55 (t, 4H), 3.96 (m, 2H), 4.06 (m, 1H), 4.89 (m, 1H), 6.9 (m, 1H), 7.14 (m, 1H), 7.21 (m, 3H), 7.32 (t, 1H), 7.42 (t, 1H), 7.56 (m, 3H), 7.79 (d, 1H), 9.88 (br s, 1H), 10.08 (br s, 1H); Mass Spectrum: M+H$^+$ 533.

EXAMPLE 31

N-[5-(3-dimethylaminobenzamido)-2-methylphenyl]-3-(2-hydroxy-3-methylaminopropoxy)benzamide In an analogous procedure to that described in Example 29, a 33% solution of methylamine in ethanol was added to a solution of N-[5-(3-dimethylaminobenzamido)-2-methylphenyl]-3-(2,3-epoxypropoxy)benzamide in a 1:1 mixture of methylene chloride and methanol and the resultant solution was stirred at ambient temperature for 18 hours. The mixture was evaporated and the residue was purified by column chromatography on silica using increasingly polar mixtures of methylene chloride and methanol as eluent. There was thus obtained the title compound in 59% yield; NMR Spectrum: (DMSOd$_6$) 2.18 (s, 3H), 2.56 (s, 3H), 2.94 (s, 6H), 3.11 (m, 2H), 4.05 (m, 2H), 4.75 (m, 1H), 6.9 (m, 1H), 7.2 (m, 4H), 7.29 (t, 1H), 7.45 (t, 1H), 7.57 (m, 3H), 7.8 (d, 1H), 9.09 (br s, 1H), 10.11 (br s, 1H); Mass Spectrum: M+H$^+$ 477.

EXAMPLE 32

N-[5-(3-dimethylaminobenzamido)-2-methylphenyl]-3-(2-hydroxy-3-dimethylaminopropoxy)benzamide Using an analogous procedure to that described in Example 31, N-[5-(3-dimethylaminobenzamido)-2- methylphenyl]-3-(2,3-epoxypropoxy)benzamide was reacted with dimethylamine to give the title compound in 68% yield; NMR Spectrum: (DMSOd$_6$) 2.18 (s, 3H), 2.56 (s, 6H), 2.95 (s, 6H), 2.78 (m, 2H), 4.03 (m, 2H), 4.18 (m, 1H), 6.9 (m, 1H), 7.16 (m, 1H), 7.23 (m, 3H), 7.3 (t, 1H), 7.43 (t, 1H), 7.57 (m, 3H), 7.8 (d, 1H), 9.93 (br s, 1H), 10.11 (br s, 1H); Mass Spectrum: M+H$^+$ 491.

EXAMPLE 33

N-[5-(3-dimethylaminobenzamido)-2-methylphenyl]-3-carboxymethoxybenzamide

Trifluoroacetic acid (10 ml) was added to a stirred solution of N-[5-(3-dimethylaminobenzamido)-2-methylphenyl]-3-tert-butoxycarbonylmethoxy-benzamide (0.5 g) in methylene chloride (10 ml) and the mixture was stirred at ambient temperature for 1 hour. The mixture was evaporated and the residue was azeotroped with toluene. The resultant gum was triturated under diethyl ether. The solid so obtained was isolated and dried under vacuum at 60° C. There was thus obtained the title compound as its trifluoroacetic acid salt (0.39 g); NMR Spectrum: (DMSOd$_6$) 2.17 (s, 3H), 2.93 (s, 6H), 4.76 (s, 2H), 6.93 (m, 1H), 7.13 (m, 1H), 7.23 (m, 3H), 7.3 (t, 1H), 7.43 (t, 1H), 7.51 (d, 1H), 7.59 (d, 2H), 7.78 (d, 1H), 9.88 (br s, 1H), 10.1 (br s, 1H); Mass Spectrum: M−H$^-$ 446.

The N-[5-(3-dimethylaminobenzamido)-2-methylphenyl]-3-tert-butoxycarbonylmethoxybenzamide was prepared as follows:

tert-Butyl bromoacetate (0.24 g) was added to a stirred mixture of N-[5-(3-dimethylaminobenzamido)-2-methylphenyl]-3-hydroxybenzamide (0.45 g), potassium carbonate (0.64 g) and DMA (8 ml) and the resultant solution was stirred and heated to 60° C. for 18 hours. The reaction mixture was allowed to cool to ambient temperature and poured into water (150 ml). The resultant precipitate was isolated washed in turn with water (50 ml) and diethyl ether (50 ml) and dried under vacuum at 60° C. There was thus obtained the required starting material (0.516 g); NMR Spectrum: (DMSOd$_6$) 1.42 (s, 9H), 2.18 (s, 3H), 2.94 (s, 6H), 4.73 (s, 2H), 6.89 (d, 1H), 7.11 (d, 1H), 7.21 (m, 2H), 7.28 (t, 1H), 7.43 (t, 1H), 7.48 (s, 1H), 7.59 (d, 2H), 7.78 (s, 1H), 9.86 (s, 1H), 10.09 (s, 1H); Mass Spectrum: M+H$^+$ 504.

EXAMPLE 34

N-[5-(3-dimethylaminobenzamido)-2-methylphenyl]-4-(3-morpholinopropylamino)benzamide Using an analogous procedure to that described in Example 20, N-[5-(3-dimethylaminobenzamido)-2-methylphenyl]-4-fluorobenzamide was reacted with 3-morpholinopropylamine to give the title compound in 3% yield; NMR Spectrum: (DMSOd$_6$) 1.77 (m, 2H), 2.24 (s, 3H), 2.46 (m, 6H), 3.02 (s, 6H), 3.16 (q, 2H), 3.65 (t, 4H), 6.33 (t, 1H), 6.67 (d, 2H), 6.97 (m, 1H), 7.28 (m, 2H), 7.36 (t, 1H), 7.62 (m, 1H), 7.83 (m, 3H), 9.45 (s, 1H), 10.06 (s, 1H); Mass Spectrum: M+H$^+$ 516.

The N-[5-(3-dimethylaminobenzamido)-2-methylphenyl]-4-fluorobenzamide used as a starting material was prepared as follows:

Oxalyl chloride (13.0 ml) was added dropwise to a stirred mixture of 3-dimethylaminobenzoic acid (20.3 g) and DMF (a few drops) which had been cooled to 0° C. The mixture was allowed to warm to ambient temperature and was stirred for 4 hours. The resultant mixture was evaporated and the residue was dissolved in methylene chloride (150 ml). 4-Methyl-3-nitroaniline (15.2 g) and triethylamine (27.9 ml) were added in turn and the resultant mixture was stirred at ambient temperature for 16 hours. The reaction mixture was washed in turn with water, with a saturated solution of sodium bicarbonate and with brine, dried (MgSO$_4$) and evaporated. The residue was triturated under a mixture of ethyl acetate and isohexane. The solid so obtained was filtered off and recrystallised from ethanol to give N-(3-nitro-4-methylphenyl)-3-dimethylaminobenzamide (6.1 g); NMR Spectrum: (DMSOd$_6$) 2.46 (s, 3H), 2.95 (s, 6H), 6.92 (d, 1H), 7.22 (m, 2H), 7.32 (t, 1H), 7.45 (d, 1H), 7.97 (d, 1H), 8.53 (s, 1H), 10.43 (s, 1H); Mass Spectrum: M+H$^+$ 300;

After repetition of the previous reactions, a sample of the product (8.25 g) was added to a stirred suspension of ammonium formate (17.4 g), and 10% palladium-on-carbon (1 g) in methanol (250 ml). The mixture was stirred and heated to reflux for 4 hours. The mixture was allowed to cool and then filtered. The filtrate was evaporated and water was added to the residue. The resultant solid was isolated and washed in turn with water, with ethyl acetate and with diethyl ether. The solid was dried in a vacuum oven at 40° C. to give N-(3-amino-4-methylphenyl)-3-dimethylaminobenzamide (6.89 g); NMR Spectrum: (DMSOd$_6$) 2.0 (s, 3H), 2.94 (s, 6H), 4.78 (s, 2H), 6.82 (m, 3H), 7.07 (s, 1H), 7.17 (m, 2H), 7.25 (m, 1H), 9.74 (s, 1H); Mass Spectrum: M+H$^+$ 270.

4-Fluorobenzoyl chloride (1.3 g) was added to a mixture of N-(3-amino-4-methylphenyl)-3-dimethylaminobenzamide (2 g), pyridine (0.88 g) and methylene chloride (15 ml) and the resultant mixture was stirred at ambient temperature for 18 hours. The mixture was washed with water and with a saturated aqueous sodium bicarbonate solution and dried (MgSO$_4$). The solid so obtained was washed with diethyl ether and dried under vacuum at 60° C. There was thus obtained the required starting material (1.39 g). NMR Spectrum: (DMSOd$_6$) 2.18 (s, 3H), 2.95 (s, 6H), 6.9 (m, 1H), 7.21 (m, 3H), 7.26 (d, 1H), 7.35 (t, 2H), 7.58 (m, 1H), 7.8 (d, 1H), 8.05 (m, 2H), 9.9 (br s, 1H), 10.08 (br s, 1H); Mass Spectrum: M+H$^+$ 392.

EXAMPLE 35

N-[5-(3-dimethylaminobenzamido)-2-methylphenyl]-2-(3-morpholinopropylamino)benzamide Using an analogous procedure to that described in Example 20, N-[5-(3-dimethylaminobenzamido)-2-methylphenyl]-2-fluorobenzamide was reacted with 3-morpholinopropylamine to give the title compound in 33% yield; m.p. 239–240° C.; NMR Spectrum: (DMSOd$_6$) 1.7 (m, 2H), 2.17 (s, 3H), 2.31 (m, 6H), 2.95 (s, 6H), 3.15 (q, 2H), 3.53 (t, 4H), 6.6 (t, 1H), 6.72 (d, 1H), 6.89 (m, 1H), 7.2 (m, 3H), 7.3 (m, 2H), (m, 1H), 7.65 (m, 1H), 7.75 (m, 2H), 9.69 (s, 1H), 10.06 (s, 1H); Mass Spectrum: M+H$^+$ 516.

The N-[5-(3-dimethylaminobenzamido)-2-methylphenyl]-2-fluorobenzamide used as a starting material was prepared by the reaction of N-(3-amino-4-methylphenyl)-3-dimethylaminobenzamide and 2-fluorobenzoyl chloride using an analogous procedure to that described in Example 10. The product gave the following data: NMR Spectrum: (DMSOd$_6$) 2.22 (s, 3H), 2.95 (s, 6H), 6.9 (d, 1H), 7.26 (m, 6H), 7.56 (m, 2H), 7.71 (t, 1H), 7.92 (s, 1H), 9.82 (s, 1H), 10.1 (s, 1H); Mass Spectrum: M+H$^+$ 392.

EXAMPLE 36

N-[5-(3-dimethylaminobenzamido)-2-methylphenyl]-4-(3-dimethylamino-N-methylpropylamino)benzamide Using an analogous procedure to that described in Example 20, N-[5-(3-dimethylaminobenzamido)-2- methylphenyl]-2-fluorobenzamide was reacted with N,N,N'-trimethyl-1,3-propanediamine to give the title compound in 29% yield; m.p. 178–179° C.; NMR Spectrum: (DMSOd$_6$) 1.64 (m, 2H), 2.13 (s, 6H), 2.17 (s, 3H), 2.22 (t, 2H), 2.95 (m, 9H), 3.41 (t, 2H), 6.73 (d, 2H), 6.89 (m, 1H), 7.19 (m, 3H), 7.29 (t, 1H), 7.56 (m, 1H), 7.8 (d, 1H), 7.84 (d, 2H), 9.44 (s, 1H), 10.05 (s, 1H); Mass Spectrum: M+H$^+$ 488.

EXAMPLE 37

N-(5benzamido-2-methylphenyl)-3-(chloromethyl) benzamide

Triethylamine (2.0 ml) was added to a stirred mixture of N-(3-amino-4-methylphenyl)benzamide (3.0 g), 3-chloromethylbenzoyl chloride (2.76 g), 4-dimethylaminopyridine (0.162 g) and methylene chloride (50 ml) and the reaction mixture was stirred at ambient temperature for 16 hours. The mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. There was thus obtained the title compound (5.1 g); NMR Spectrum: (DMSOd$_6$) 2.19 (s, 3H), 4.85 (s, 2H), 7.23 (d, 1H), 7.55 (m, 5H), 7.66 (d, 1H), 7.84 (s, 1H), 7.95 (m, 3H), 8.05 (s, 1H), 9.96 (s, 1H), 10.22 (s, 1H); Mass Spectrum: M–H$^-$ 377.

The N-(3-amino-4-methylphenyl)benzamide used as a starting material was prepared as follows:

Benzoyl chloride (1.9 ml) was added to a stirred mixture of 2,4-diaminotoluene (2 g), triethylamine (5.57 ml) and methylene chloride (80 ml) and the mixture was stirred at ambient temperature for 16 hours. The mixture was washed with a saturated aqueous solution of sodium bicarbonate. The organic phase was dried (MgSO$_4$) and evaporated. The residue was triturated with a mixture of ethyl acetate and diethyl ether. There was thus obtained the required starting material (1.32 g); NMR Spectrum: (DMSOd$_6$) 2.01 (s, 3H), 4.8 (s, 2H), 6.82 (m 2H), 7.11 (s, 1H), 7.5 (m, 3H), 7.91 (m, 2H), 9.86 (s, 1H); Mass Spectrum: M+H$^+$ 227.

EXAMPLE 38

N-(5-benzamido-2-methylphenyl)-4-(chloromethyl) benzamide

Using an analogous procedure to that described in Example 37, 4-chloromethylbenzoyl chloride was reacted with N-(3-amino-4-methylphenyl)benzamide to give the title compound in 99% yield; NMR Spectrum: (DMSOd$_6$) 2.19 (s, 3H), 4.84 (s, 2H), 7.22 (d, 1H), 7.54 (m, 6H), 7.84 (s, 1H), 7.96 (m, 4H), 9.92 (s, 1H), 10.22 (s, 1H); Mass Spectrum: M–H$^-$ 377.

EXAMPLE 39

N-[5-(3-trifluoromethylbenzamido)-2-methylphenyl]-3-(chloromethyl)benzamide

Using an analogous procedure to that described in Example 37, 3-chloromethylbenzoyl chloride was reacted with N-(3-amino-4-methylphenyl)-3-trifluoromethylbenzamide to give the title compound in 94% yield; NMR Spectrum: (DMSOd$_6$) 2.2 (s, 3H), 4.85 (s, 2H), 7.25 (d, 1H), 7.6 (m, 3H), 7.8 (m, 2H), 7.95 (d, 2H), 8.05 (s, 1H), 8.16 (m, 2H), 9.96 (s, 1), 10.44 (s, 1H); Mass Spectrum: M–H$^-$ 445.

The N-(3-amino-4-methylphenyl)-3-trifluoromethylbenzamide used as a starting material was prepared as follows:

A mixture of 3-trifluoromethylbenzoyl chloride (9.9 ml), 3-nitro-4-methylaniline (10 g) and pyridine (100 ml) was stirred and heated to 80° C. for 2 hours. The reaction mixture was evaporated and the residue was triturated under 2N aqueous hydrochloric acid solution. The solid so obtained was isolated, washed in turn with a saturated aqueous sodium bicarbonate solution, water and isohexane and dried under vacuum at 55° C. to give N-(4-methyl-3-nitrophenyl)-3-trifluoromethylbenzamide as a solid (21.9 g); NMR Spectrum: (DMSOd$_6$) 7.49 (d, 1H), 7.78 (m, 1H), 7.99 (m, 2H), 8.27 (m, 2H), 8.51 (s, 1H), 10.77 (s, 1H); Mass Spectrum: M–H$^-$ 323.

10% Palladium-on-charcoal (1.0 g) was added to a solution of a portion (10 g) of the material so obtained in methanol (250 ml). Ammonium formate (19.0 g) was added and the resultant mixture was stirred and heated to reflux for 1 hour. The mixture was filtered through diatomaceous earth and the filtrate was evaporated. The residue was triturated under water. The resultant solid was isolated and dried under vacuum at 55° C. to give N-(3-amino-4-methylphenyl)-3-trifluoromethylbenzamide as a solid (7.98 g); NMR Spectrum: (DMSOd$_6$) 2.01 (s, 3H), 4.83 (s, 2H), 6.85 (m, 2H), 7.08 (s, 1H), 7.74 (t, 1H), 7.92 (d, 1H), 8.2 (d, 1H), 10.11 (s, 1H); Mass Spectrum: M–H$^-$ 293.

EXAMPLE 40

N-[5-(3-trifluoromethylbenzamido)-2-methylphenyl]-4-(chloromethyl)benzamide

Using an analogous procedure to that described in Example 37, 4-chloromethylbenzoyl chloride was reacted with N-(3-amino-4-methylphenyl)-3-trifluoromethylbenzamide to give the title compound in 94% yield; NMR Spectrum: (DMSOd$_6$) 2.21 (s, 3H), 4.84 (s, 2H), 7.25 (d, 1H), 7.57 (m, 3H), 7.76 (t, 1H), 7.83 (d, 1H), 7.96 (m, 3H), 8.26 (m, 2H), 9.92 (s, 1H), 10.44 (s, 1H); Mass Spectrum: M–H$^-$ 445.

EXAMPLE 41

N-[5-(4-cyanobenzamido)-2-methylphenyl]-3-(diethylaminomethyl)benzamide

Diethylamine hydrochloride (0.33 g) was added to a stirred mixture of N-[5-(4-cyanobenzamido)-2-methylphenyl]-3-chloromethylbenzamide (0.4 g), potassium carbonate (0.5 g) and acetone (6 ml) and the reaction mixture was stirred and heated to 55° C. for 16 hours. The reaction mixture was evaporated and the residue was triturated under water. The solid was isolated and dried under vacuum at 55° C. to give the title compound (0.24 g); NMR Spectrum: (DMSOd$_6$) 0.95 (t, 6H), 2.19 (s, 3H), 3.58 (s, 2H), 7.22 (d, 1H), 7.5 (m, 3H), 7.85 (m, 3H), 7.99 (d, 2H), 8.12 (d, 2H); Mass Spectrum: M–H$^-$ 439.

EXAMPLE 42

Using an analogous procedure to that described in Example 41, the appropriate amine was reacted with the appropriate chloromethylbenzamide to give the compounds described in Table IV.

TABLE IV

![structure: (R¹)ₘ-phenyl-CONH-(Me-phenyl)-NHCO-phenyl-R]

| No. | (R¹)ₘ | R | Note |
|---|---|---|---|
| 1 | 4-(3-methoxypropylaminomethyl) | 3-trifluoromethyl | a |
| 2 | 4-(N-methyl-N-propylaminomethyl) | 4-cyano | b |
| 3 | 4-(diethylaminomethyl) | 3-dimethylamino | c |
| 4 | 3-[N-(3-dimethylaminopropyl)-N-methylaminomethyl] | 3-trifluoromethyl | d |
| 5 | 4-(2-morpholinoethylaminomethyl) | hydrogen | e |
| 6 | 4-(N-benzyl-N-methylaminomethyl) | hydrogen | f |

Notes a The amine reactant was 3-methoxypropylamine. The product gave the following data: NMR (DMSOd₆) 1.72 (m, 2H), 2.2 (s, 3H), 3.2 (m, 7H), 3.63 (s, 2H), 7.24 (d, 1H), 7.48 (m, 2H), 7.6 (d, 1H), 7.79 (m, 2H), 7.95 (m, 3H), 8.27 (m, 2H), 9.85 (s, 1H), 10.47 (s, 1H); Mass M − H 498.

b The amine reactant was N-methyl-N-propylamine. The product gave the following data: NMR (DMSOd₆) 0.94 (t, 3H), 1.46 (m, 2H), 2.11 (s, 3H), 2.2 (s, 3H), 2.3 (t, 2H), 3.51 (s, 2H), 7.22 (d, 1H), 7.42 (d, 2H), 7.57 (d, 1H), 7.82 (d, 1H), 7.93 (d, 2H), 7.98 (d, 2H), 8.12 (d, 2H); Mass M − H 439.

c The product gave the following data: NMR (DMSOd₆) 0.98 (t, 6H), 2.19 (s, 3H), 2.95 (s, 6H), 3.59 (s, 2H), 6.9 (d, 1H), 7.2 (m, 3H), 7.29 (d, 1H), 7.45 (d, 2H), 7.58 (d, 1H), 7.80 (s, 1H), 7.93 (d, 2H), 9.81 (s, 1H), 10.08 (s, 1H); Mass M + H 460.

d The amine reactant was N-(3-dimethylaminopropyl)-N-methylamine. The product gave the following data: NMR (DMSOd₆) 1.58 (m, 2H), 2.09 (s, 6H), 2.13 (s, 3H), 2.21 (m, 5H), 2.36 (t, 2H), 3.52 (s, 2H), 7.23 (d, 1H), 7.4–8.0 (m, 8H), 8.27 (m, 2H); Mass M − H 525.

e The amine reactant was 2-morpholinoethylamine. The product gave the following data: NMR (DMSOd₆) 2.19 (s, 3H), 2.2–2.6 (m, 8H), 3.55 (m, 4H), 3.73 (d, 2H), 7.21 (d, 1H), 7.4–7.6 (m, 6H), 7.83 (s, 1H), 7.94 (m, 4H), 9.84 (s, 1H), 10.22 (s, 1H); Mass M − H 471.

f The amine reactant was N-benzyl-N-methylamine. The product gave the following data: NMR (DMSOd₆) 2.1 (s, 3H), 2.19 (s, 3H), 3.52 (s, 2H), 3.58 (s, 2H), 7.2–7.6 (m, 12H), 7.82 (s, 1H), 7.95 (m, 4H), 9.85 (broad s, 1H), 10.22 (broad s, 1H); Mass M − H 462.

EXAMPLE 43

N-[5-(3-cyclohexylpropionamido)-2-methylphenyl]-4-(diethylaminomethyl)benzamide

Using an analogous procedure to that described in Example 22 except that the step of washing the reaction mixture with a 1M aqueous citric acid solution was omitted, N-(5-amino-2-methylphenyl)-4-diethylaminomethylbenzamide was reacted with 3-cyclohexylpropionyl chloride (obtained by the reaction of 3-cyclohexylpropionic acid and oxalyl chloride using a conventional procedure) to give the title compound; Mass Spectrum: M+H⁺ 450.

EXAMPLE 44

N-[5-(4-cyclohxylbutyramido)-2-methylphenyl]-4-(diethylaminomethyl)benzamide

Using an analogous procedure to that described in Example 22 except that the step of washing the reaction mixture with a 1M aqueous citric acid solution was omitted, N-(5-amino-2-methylphenyl)-4-diethylaminomethylbenzamide was reacted with 4-cyclohexylbutyryl chloride (obtained by the reaction of 4-cyclohexylbutyric acid and oxalyl chloride using a conventional procedure) to give the title compound; Mass Spectrum: M+H⁺ 464.

EXAMPLE 45

N-[2-methyl-5-(3-morpholinobenzamido)phenyl]-3-(2,3-epoxypropoxy)benzamide

1-Bromo-2,3-epoxypropane (1.5 ml) was added to a stirred mixture of N-[2-methyl-5-(3-morpholinobenzamido) phenyl]-3-hydroxybenzamide (1.5 g), caesium carbonate (2.84 g) and DMA (100 ml) and the resultant solution was stirred at ambient temperature for 18 hours. The mixture was poured into water (750 ml). The precipitate was isolated, washed with water and dried under vacuum at 60° C. There was thus obtained the title compound (1.3 g); NMR Spectrum: (DMSOd₆) 2.19 (s, 3H), 2.73 (m, 1H), 2.85 (m, 1H), 3.2 (t, 4H), 3.75 (t, 4H), 3.91 (m, 1H), 4.43 (m, 1H), 7.2 (m, 3H), 7.37 (m, 4H), 7.66 (m, 3H), 7.56 (m, 3H), 7.8 (s, 1H), 9.9 (s, 1H), 10.14 (s, 1H); Mass Spectrum: M−H⁻ 486.

EXAMPLE 46

N-[5-(3-dimethylaminobenzamido)-2-methylphenyl]-3-{3-[N-(3-dimethylaminopropyl)-N-methylamino]-2-hydroxypropoxy}benzamide Using an analogous procedure to that described in Example 31, N-[5-(3-dimethylaminobenzamido)-2-methylphenyl]-3-(2,3-epoxypropoxy)benzamide was reacted with N-(3-dimethylaminopropyl)-N-methylamine to give the title compound in 45% yield; NMR Spectrum: (DMSOd₆) 1.8 (m, 2H), 2.18 (s, 3H), 2.33 (s, 3H), 2.58 (s, 6H), 2.6 (m, 2H), 2.92 (t, 2H), 2.96 (s, 6H), 4.03 (m, 5H), 6.9 (m, 1H), 7.15 (m, 1H), 7.2 (m, 3H), 7.28 (t, 1H), 7.48 (t, 1H), 7.56 (m, 2H), 7.8 (d, 1H), 9.95 (s, 1H), 10.13 (s, 1H); Mass Spectrum: M+H⁺ 562.

EXAMPLE 47

N-[2-methyl-5-(3-morpholinobenzamido)phenyl]-4-(6-chloropyrimidin-4-yloxy)benzamide 4,6-Dichloropyrimidine (0.103 g) was added to a stirred mixture of N-[2-methyl-5-(3-morpholinobenzamido) phenyl]-4-hydroxybenzamide (0.3 g), caesium carbonate (0.453 g) and DMA (7.5 ml) and the resultant solution was stirred at ambient temperature for 18 hours. The mixture was poured into water (200 ml) and extracted with ethyl acetate. The organic phase was washed with water, dried (MgSO₄) and evaporated. The residue was purified by column chromatography on silica using increasingly polar mixtures of methylene chloride and methanol as eluent. The material so obtained was triturated under diethyl ether. The resultant solid was isolated, washed with diethyl ether and dried under vacuum at 60° C. There was thus obtained the title compound (0.2 g); NMR Spectrum: (DMSOd₆) 2.19 (s, 3H), 3.2 (t, 4H), 3.74 (t, 4H), 7.12 (m, 1H), 7.23 (m, 1H), 7.41 (m, 6H), 7.58 (m, 1H), 7.82 (d , 3H); 8.06 (d, 2H), 8.67 (s, 1H), 9.93 (s, 1H), 10.12 (s, 1H); Mass Spectrum: M+H⁺ 544.

EXAMPLE 48

N-[2-methyl-5-(3-morpholinobenzamido)phenyl]-3-(6-chloropyrimidin-4-yloxy)benzamide Using an analogous procedure to that described in Example 47, 4,6-dichloropyrimidine was reacted with N-[2-methyl-5-(3-morpholinobenzamido)phenyl]-3-hydroxybenzamide to give the title compound in 42% yield; NMR Spectrum: (DMSOd₆) 2.18 (s, 3H), 3.14 (t, 4H), 3.73 (t, 4H), 7.22 (d, 1H), 7.34 (m, 2H), 7.47 (m, 3H), 7.57 (m, 1H), 7.63 (t, H), 7.81 (d, 1H), 7.93 (d, 1H), 8.66 (s, 1H), 9.96 (s, 1H), 10.14 (s, 1H); Mass Spectrum: M+H⁺ 544.

EXAMPLE 49

N-[2-methyl-5-(3-morpholinobenzamido)phenyl]-4-methoxy-3-piperidin-4-yloxybenzamide Using an analogous procedure to that described in Example 25, 3-(1-tert-butoxycarbonylpiperidin-4-yloxy)-4- methoxybenzoic acid was reacted with N-(3-amino-4-methylphenyl)-3-morpholinobenzamide to give N-[2-methyl-5-(3-morpholinobenzamido)phenyl]-3-(1-tert-butoxycarbonylpiperidin-4-yloxy)-4-methoxybenzamide in 48% yield and that product was treated with trifluoroacetic acid. The reaction mixture was evaporated, water (40 ml) was added to the residue and the mixture was basified by the addition of 1N aqueous sodium hydroxide solution. The water was decanted and the residue was titurated under diethyl ether. The resultant solid was isolated, dissolved in water (30 ml) and basified by the addition of potassium carbonate. The precipitate was isolated and dried. There was thus obtained the title compound in 26% yield; NMR Spectrum: (DMSOd$_6$) 1.48 (m, 2H), 1.9 (m, 2H), 2.18 (s, 3H), 3.19 (m, 4H), 3.75 (m, 4H), 3.83 (s, 3H), 4.39 (m, 1H), 7.1 (m, 2H), 7.21 (d, 1H), 7.4 (m, 3H), 7.6 (m, 3H), 7.79 (s, 1H), 9.72 (s, 1H), 10.1 (s, 1H); Mass Spectrum: M+H$^+$ 545.

The 3-(1-tert-butoxycarbonylpiperidin-4-yloxy)-4-methoxybenzoic acid used as a starting material was obtained by the reaction of N-tert-butoxycarbonyl-4-hydroxypiperidine and ethyl 3-hydroxy-4-methoxybenzoate (*J. Amer. Chem. Soc.*, 1953, 75, 2630–2631) using an analogous procedure to that described in the portion of Example 25 which is concerned with the preparation of starting materials. There was thus obtained the required starting material as a solid; NMR Spectrum: (DMSOd$_6$) 1.2 (s, 9H), 1.5 (m, 2H), 1.85 (m, 2H), 3.18 (m, 2H), 3.64 (m, 2H), 3.81 (s, 3H), 4.48 (m, 1H), 7.05 (d, 1H), 7.48 (m, 1H), 7.58 (m, 1H); Mass Spectrum: M–H$^-$ 350.

EXAMPLE 50

N-[5-(3-fluoro-5-morpholinobenzamido)-2-methylphenyl]-3-piperidin-4-yloxybenzamide 1-(3-Dimethylaminopropyl)-3-ethylcarbodiimide hydrochloride (0.23 g) was added to a stirred mixture of 3-(1-tert-butoxycarbonylpiperidin-4-yloxy)benzoic acid (0.321 g), N-(3-amino-4-methylphenyl)-3-fluoro-5-morpholinobenzamide (0.329 g), 1-hydroxybenzotriazole (0.202 g) and DMF (5 ml) which had been cooled to 0° C. The reaction mixture was allowed to warm to ambient temperature and was stirred for 40 hours. The reaction mixture was partitioned between ethyl acetate and water. The organic phase was washed with water, and with a saturated aqueous sodium bicarbonate solution, dried (MgSO$_4$) and evaporated. The residue was purified by column chromatography on silica using increasingly polar mixtures of methylene chloride and methanol as eluent. There was thus obtained N-[5-(3-fluoro-5-morpholinobenzamido)-2-methylphenyl]-3-(1-tert-butoxycarbonylpiperidin-4-yloxy)benzamide (0.423 g); NMR Spectrum: (DMSOd$_6$) 1.38 (s, 9H), 1.57 (m, 2H), 1.93 (m, 2H), 2.18 (s, 3H), 3.16 (m, 2H), 3.2 (t, 4H), 3.65 (m, 2H), 3.74 (t, 4H), 4.65 (m, 1H), 6.95 (m, 1H), 7.12 (m, 1H), 7.2 (m, 2H), 7.28 (d, 1H), 7.41 (t, 1H), 7.57 (m, 3H), 7.78 (d, 1H), 9.82 (s, 1H), 10.15 (s, 1H); Mass Spectrum: M+H$^+$ 633.

Trifluoroacetic acid (0.9 ml) was added to a stirred solution of the material so obtained in methylene chloride (9 ml) which had been cooled to 0° C. The reaction mixture was stirred for 3 hours and allowed to warm to ambient temperature. The mixture was evaporated and the residue was triturated under diethyl ether to give the title compound, as its trifluoroacetate salt. The solid so obtained was dissolved in water (20 ml) and basified by the addition of potassium carbonate. The resultant precipitate was collected and dried under vacuum to give the title compound (0.214 g); NMR Spectrum: (DMSOd$_6$) 1.6 (m, 2H), 1.97 (m, 2H), 2.18 (s, 3H), 2.77 (m, 2H), 3.03 (m, 2H), 3.2 (t, 4H), 3.76 (t, 4H), 4.56 (m, 1H), 6.96 (d, 1H), 7.1 (d, 1H), 7.18 (d, 1H), 7.21 (d, 1H), 7.27 (s, 1H), 7.4 (t, 1H), 7.57 (m, 3H), 7.78 (s, 1H), 9.83 (s, 1H), 10.15 (s, 1H); Mass Spectrum: M+H$^+$ 533.

The N-(3-amino-4-methylphenyl)-3-fluoro-5-morpholinobenzamide used as a starting material was obtained as follows:

A solution of 3,5-difluorobenzoyl chloride (2.82 g) in methylene chloride (20 ml) was added to a stirred mixture of 4-methyl-3-nitroaniline (2.28 g), triethylamine (4.35 ml) and methylene chloride (80 ml). The resultant mixture was stirred at ambient temperature for 16 hours. The precipitate was isolated, washed with methylene chloride and dried. There was thus obtained N-(4-methyl-3-nitrophenyl)-3,5-difluorobenzamide; NMR Spectrum: (DMSOd$_6$) 2.43 (s, 3H), 7.43 (m, 2H), 7.63 (m, 2H), 7.95 (m, 2H), 8.43 (d, 1H), 10.42 (s, 1H); Mass Spectrum: M+H$^+$ 293.

A mixture of a portion (1 g) of the material so obtained and morpholine (5 ml) was stirred and heated to 100° C. for 48 hours and then to 120° C. for 24 hours. The reaction mixture was cooled and poured into water (100 ml). The resultant solid was isolated, washed with water and dried. The material so obtained was purified by column chromatography on silica using a 1:1 mixture of isohexane and ethyl acetate as eluent. There was thus obtained N-(4-methyl-3-nitrophenyl)-3-fluoro-5-morpholinobenzamide as a solid (0.53 g); NMR Spectrum: (DMSOd$_6$) 2.46 (s, 3H), 3.22 (t, 4H), 3.75 (t, 4H), 6.98 (m, 1H), 7.12 (d, 1H), 7.27 (s, 1H), 7.46 (d, 1H), 7.96 (m, 1H), 8.43 (d, 1H), 10.48 (s, 1H); Mass Spectrum: M+H$^+$ 360.

A portion (0.483 g) of the compound so obtained was dissolved in ethyl acetate (40 ml) and hydrogenated over 10% palladium-on-carbon catalyst (0.6 g) under an atmosphere of hydrogen until the uptake of hydrogen ceased. The catalyst was removed by filtration and the filtrate was evaporated. The residue was triturated under diethyl ether (25 ml). The resultant solid was collected, washed with diethyl ether and dried. There was thus obtained the required starting material (0.341 g); NMR Spectrum: (DMSOd$_6$) 1.99 (s, 3H), 3.19 (t, 4H), 3.76 (t, 4H), 4.8 (s, 2H), 6.75 (d, 1H), 6.82 (d, 1H), 6.9 (d, 1H), 7.02 (s, 1H), 7.04 (d, 1H), 7.23 (s, 1H), 9.81 (s, 1H).

EXAMPLE 51

N-[2-methyl-5-(3-piperidinobenzamido)phenyl]-3-piperidin 4-yloxybenzamide

Using an analogous procedure to that described in the first paragraph of Example 25, 3-(1-tert-butoxycarbonylpiperidin-4-yloxy)benzoic acid was reacted with N-(3-amino-4-methylphenyl)-3-piperidinobenzamide to give N-[2-methyl-5-(3-piperidinobenzamido)phenyl]-3-(1-tert-butoxycarbonylpiperidin-4-yloxy)benzamide in 57% yield; NMR Spectrum: (DMSOd$_6$) 1.39 (s, 9H), 1.54 (m, 4H), 1.62 (m, 4H), 1.91 (m, 2H), 2.19 (s, 3H), 3.2 (m, 4H), 3.65 (m, 2H), 4.64 (m, 4H), 7.09 (m, 1H), 7.19 (m, 2H), 7.27 (m, 2H), 7.41 (t, 2H), 7.58 (m, 2H), 7.79 (m, 1H), 9.83 (s, 1H), 10.09 (s, 1H); Mass Spectrum: M–C$_3$H$_7$$^+$ 557.

The product so obtained was treated with trifluoroacetic acid using an analogous procedure to that described in the second paragraph of Example 25. The reaction mixture was evaporated and the residue was triturated under diethyl ether. The solid so obtained was dissolved in water (60 ml) and the solution was basified by the addition of 1N aqueous sodium hydroxide solution. The resultant solid was isolated and dried. There was thus obtained the title compound in 66% yield; NMR Spectrum: (DMSOd$_6$) 1.5 (m, 8H), 1.91 (m, 2H), 2.18 (s, 3H), 2.57 (m, 2H), 2.93 (m, 2H), 3.2 (m, 2H), 4.45 (s, 1H), 7.1 (m, 2H), 7.2 (d, 1H), 7.28 (d, 2H), 7.4 (m, 2H), 7.56 (m, 3H), 7.78 (s, 1H), 9.83 (s, 1H), 10.09 (s, 1H); Mass Spectrum: M+H$^+$ 513.

The N-(3-amino-4-methylphenyl)-3-piperidinobenzamide used as a starting material was obtained as follows:

A mixture of piperidine (20.9 ml), 3-fluorobenzonitrile (4.36 g) and DMSO (30 ml) was stirred and heated to 100° C. for 64 hours. The mixture was allowed to cool to ambient temperature and was partitioned between diethyl ether and water. The organic phase was washed with a saturated aqueous sodium chloride solution, dried (MgSO$_4$) and evaporated. The residue was purified by column chromatography on silica using a 9:1 mixture of isohexane and ethyl acetate as eluent. There was thus obtained 3-piperidinobenzonitrile as an oil (5.7 g); NMR Spectrum: (CDCl$_3$) 1.52 (m, 2H), 1.6 (m, 4H), 3.17 (t, 4H), 6.95 (d, 1H), 7.02 (m, 2H), 7.21 (m, 1H).

A mixture of the material so obtained, 5N aqueous sodium hydroxide solution (30 ml) and n-butanol (25 ml) was stirred and heated to reflux for 24 hours. The mixture was evaporated and the residual solid was triturated under a mixture of diethyl ether (100 ml) and water (50 ml). The aqueous layer was separated, acidified to pH5 by the addition of 1N aqueous hydrochloric acid and extracted with methylene chloride (2×50 ml). The combined organic extracts were dried (MgSO$_4$) and evaporated. There was thus obtained 3-piperidinobenzoic acid (3.1 g); NMR Spectrum: (DMSOd$_6$) 1.57 (m, 6H), 3.18 (t, 4H), 7.17 (m, 1H), 7.27 (m, 2H), 7.41 (d, 1H), 12.72 (s, 1H).

A mixture of the material so obtained, oxalyl chloride (0.93 ml), DMF (3 drops) and methylene chloride (80 ml) was stirred at ambient temperature for 4 hours. The resultant mixture was evaporated. The material so obtained was dissolved in methylene chloride (80 ml) and added to a stirred mixture of 4-methyl-3-nitroaniline (1.14 g), triethylamine (2.19 ml) and methylene chloride (80 ml). The mixture was stirred at ambient temperature for 18 hours. The mixture was then washed in turn with water, with a saturated aqueous sodium bicarbonate solution and with water, dried (MgSO$_4$) and evaporated. The residue was purified by column chromatography on silica using a 9:1 mixture of isohexane and ethyl acetate as eluent. There was thus obtained N-(4-methyl-3-nitrophenyl)-3-piperidinobenzamide as a solid (0.82 g); NMR Spectrum: (DMSOd$_6$) 1.5 (m, 2H), 1.61 (m, 4H), 2.5 (s, 3H), 3.2 (t, 4H), 7.1 (m, 1H), 7.28 (m, 2H), 7.42 (m, 1H), 7.46 (s, 1H), 8.52 (d, 1H).

A mixture of the material so obtained, 10% palladium-on-carbon catalyst (0.15 g) and methanol (150 ml) was stirred under an atmosphere pressure of hydrogen at ambient temperature for 18 hours. The catalyst was filtered off and the filtrate was evaporated to give the required starting material as a solid (0.561 g); NMR Spectrum: (DMSOd$_6$) 1.54 (t, 4H), 1.63 (m, 4H), 2.01 (s, 3H), 3.19 (t, 4H), 4.78 (s, 2H), 6.68 (m, 1H), 6.82 (d, 1H), 7.06 (m, 2H), 7.24 (m, 2H), 7.39 (s, 1H), 9.77 (s, 1H).

EXAMPLE 52

N-[5-(3-fluoro-5-piperidinobenzamido)-2-methylphenyl]-3-piperidin-4-yloxybenzamide Using an analogous procedure to that described in the first paragraph of Example 50, 3-(1-tert-butoxycarbonylpiperidin-4-yloxy)benzoic acid was reacted with N-(3-amino-4-methylphenyl)-3-fluoro-5-piperidinobenzamide to give N-[5-(3-fluoro-5-piperidinobenzamido)-2-methylphenyl]-3-(1-tert-butoxycarbonylpiperidin-4-yloxy)benzamide in 59% yield; NMR Spectrum: (DMSOd$_6$) 1.38 (s, 9H), 1.59 (m, 8H), 1.95 (m, 1H), 2.19 (s, 3H), 3.20 (m, 6H), 3.64 (m, 2H), 4.63 (m, 1H), 6.90 (d, 1H), 7.02 (d, 1H), 7.22 (m, 3H), 7.41 (t, 1H), 7.57 (m, 3H), 7.78 (s, 1H), 9.83 (s, 1H), 10.13 (s, 1H); Mass Spectrum: M+H$^+$ 631.

The product so obtained was treated with trifluoroacetic acid using an analogous procedure to that described in the second paragraph of Example 50. There was thus obtained the title compound in 72% yield; NMR Spectrum: (DMSOd$_6$) 1.41 (m, 2H), 1.59 (m, 8H), 1.9 (m, 1H), 2.19 (s, 3H), 2.58 (m, 2H), 2.96 (m, 2H), 3.24 (m, 4H), 4.43 (m, 1H), 6.9 (d, 1H), 7.02 (d, 1H), 7.17 (d, 1H), 7.21 (d, 1H), 7.27 (s, 1H), 7.41 (t, 1H), 7.57 (m, 3H), 7.78 (s, 1H), 9.83 (s, 1H), 10.13 (s, 1H); Mass Spectrum: M+H$^+$ 531.

The N-(3-amino-4-methylphenyl)-3-fluoro-5-piperidinobenzamide used as a starting material was obtained as follows:

A mixture of N-(4-methyl-3-nitrophenyl)-3,5-difluorobenzamide (1 g) and piperidine (5 ml) was stirred and heated to 100° C. for 36 hours. The reaction mixture was cooled and partitioned between ethyl acetate and water. The organic phase was washed with a saturated aqueous sodium chloride solution, dried (MgSO$_4$) and evaporated. The residue was purified by column chromatography on silica using a 7:3 mixture of isohexane and ethyl acetate as eluent. There was thus obtained N-(4-methyl-3-nitrophenyl)-3-fluoro-5-piperidinobenzamide as a solid (1.12 g); NMR Spectrum: (DMSOd$_6$) 1.78 (m, 6H), 2.5 (s, 3H), 3.18 (t, 4H), 6.62 (m, 1H), 6.75 (m, 1H), 7.09 (d, 1H), 7.23 (d, 1H), 7.78 (m, 1H), 7.82 (s, 1H), 8.18 (d, 1H).

A portion (0.8 g) of the compound so obtained was dissolved in ethanol (80 ml) and hydrogenated over 10% palladium-on-carbon catalyst (0.1 g) under an atmosphere of hydrogen until the uptake of hydrogen ceased. The catalyst was removed by filtration and the filtrate was evaporated. The residue was triturated under ethyl acetate to give the required starting material (0.48 g); NMR Spectrum: (DMSOd$_6$) 1.56 (m, 6H), 2.0 (s, 3H), 3.21 (t, 4H), 4.78 (s, 2H), 6.76 (m, 1H), 6.82 (d, 1H), 6.84 (m, 1H), 6.98 (d, 1H), 7.03 (d, 1H), 7.22 (s, 1H), 9.80 (s, 1H); Mass Spectrum: M+H$^+$ 328.

EXAMPLE 53

N-[2-methyl-5-(3-pyrrolidin-1-ylbenzamido)phenyl]-3-piperidin-4-yloxybenzamide

Using an analogous procedure to that described in the first paragraph of Example 25, 3-(1-tert-butoxycarbonylpiperidin-4-yloxy)benzoic acid was reacted with N-(3-amino-4-methylphenyl)-3-pyrrolidin-1-ylbenzamide to give N-[2-methyl-5-(3-pyrrolidin-1-ylbenzamido)phenyl]-3-(1-tert-butoxycarbonylpiperidin-4-yloxy)benzamide in 69% yield; NMR Spectrum: (DMSOd$_6$) 1.39 (s, 9H), 1.56 (m, 2H), 1.87 (m, 2H), 3.2 (m, 2H), 3.64 (m, 2H), 4.62 (m, 1H), 6.69 (d, 1H), 7.02 (s, 1H), 7.2 (m, 4H), 7.42 (t, 1H), 7.56 (m, 3H), 7.79 (s, 1H), 9.83 (s, 1H), 10.05 (s, 1H); Mass Spectrum: M+H$^+$ 599.

The product so obtained was treated with trifluoroacetic acid using an analogous procedure to that described in the second paragraph of Example 25. The reaction mixture was evaporated and the residue was triturated under diethyl ether.

The solid so obtained was dissolved in water (50 ml) and the solution was basified by the addition of 1N aqueous sodium hydroxide solution. The resultant solid was isolated and dried. There was thus obtained the title compound in 62% yield; NMR Spectrum: (DMSOd$_6$) 1.46 (m, 2H), 1.94 (m, 4H), 2.19 (s, 3H), 2.6 (m, 2H), 2.98 (m, 2H), 3.3 (m, 4H), 4.48 (m, 1H), 6.68 (d, 1H), 7.02 (s, 1H), 7.2 (m, 4H), 7.4 (m, 1H), 7.56 (m, 3H), 7.8 (s, 1H), 9.83 (s, 1H), 10.05 (s, 1H); Mass Spectrum: M+H$^+$ 499.

The N-(3-amino-4-methylphenyl)-3-pyrrolidin-1-ylbenzamide used as a starting material was obtained as follows:

A mixture of pyrrolidine (7.1 g), 3-fluorobenzonitrile (2.23 g) and DMSO (25 ml) was stirred and heated to 100° C. for 20 hours. The mixture was allowed to cool to ambient temperature and was partitioned between diethyl ether and water. The organic phase was washed with a saturated aqueous sodium chloride solution, dried (MgSO$_4$) and evaporated. The residue was purified by column chromatography on silica using a 9:1 mixture of isohexane and ethyl acetate as eluent. There was thus obtained 3-pyrrolidin-1-ylbenzonitrile as a solid (1.94 g); NMR Spectrum: (CDCl$_3$) 2.03 (t, 4H), 3.23 (t, 4H), 6.7 (m, 2H), 6.86 (t, 1H), 7.21 (d, 1H).

A mixture of a portion (1.23 g) of the material so obtained, 5N aqueous sodium hydroxide solution (10 ml) and n-butanol (8 ml) was stirred and heated to reflux for 20 hours. The mixture was evaporated. 1N aqueous hydrochloric acid (50 ml) was added followed by sufficient of a saturated aqueous sodium bicarbonate solution to bring the mixture to pH6. The solid was collected and dried to give 3-pyrrolidin-1-ylbenzoic acid (1.8 g); NMR Spectrum: (DMSOd$_6$) 1.93 (t, 4H), 3.21 (t, 4H), 6.85 (m, 1H), 7.07 (d, 1H), 7.18 (d, 1H), 7.22 (t, 1H).

A mixture of the material so obtained, oxalyl chloride (0.93 ml), DMF (3 drops) and methylene chloride (80 ml) was stirred at ambient temperature for 4 hours. The resultant mixture was evaporated. The material so obtained was dissolved in methylene chloride (80 ml) and added to a stirred mixture of 4-methyl-3-nitroaniline (1.14 g), triethylamine (2.19 ml) and methylene chloride (80 ml). The mixture was stirred at ambient temperature for 18 hours. The mixture was then washed in turn with water, with a saturated aqueous sodium bicarbonate solution and with water, dried (MgSO$_4$) and evaporated. The residue was triturated under diethyl ether. There was thus obtained N-(4-methyl-3-nitrophenyl)-3-pyrrolidin-1-ylbenzamide as a solid (1.24 g); NMR Spectrum: (DMSOd$_6$) 1.95 (t, 4H), 2.43 (s, 3H), 3.23 (t, 4H), 6.73 (m, 1H), 7.02 (s, 1H), 7.17 (d, 1H), 7.26 (t, 1H), 7.42 (d, 1H), 7.98 (m, 1H), 8.52 (d, 1H), 11.83 (s, 1H).

A mixture of the material so obtained, 10% palladium-on-carbon catalyst (0.15 g) and methanol (150 ml) was stirred under an atmosphere pressure of hydrogen at ambient temperature for 48 hours. The catalyst was filtered off and the filtrate was evaporated. The residue was triturated under diethyl ether to give the required starting material as a solid (0.5 g); NMR Spectrum: (DMSOd$_6$) 1.95 (m, 4H), 2.0 (s, 3H), 3.27 (m, 4H), 4.77 (s, 2H), 6.65 (m, 1H), 6.8 (m, 2H), 6.99 (s, 1H), 7.1 (m, 2H), 7.23 (m, 1H), 9.7 (s, 1H); Mass Spectrum: M+H$^+$ 296.

EXAMPLE 54

N-[2-methyl-5-(3-morpholinobenzamido)phenyl]-3-pyrrolidin-3-yloxybenzamide

Using an analogous procedure to that described in the first paragraph of Example 25, 3-(1-tert-butoxycarbonylpyrrolidin-3-yloxy)benzoic acid was reacted with N-(3-amino-4-methylphenyl)-3-morpholinobenzamide to give N-[2-methyl-5-(3-morpholinobenzamido)phenyl]-3-(1-tert-butoxycarbonylpyrrolidin-3-yloxy)benzamide in 58% yield; NMR Spectrum: (DMSOd$_6$) 1.38 (s, 9H), 2.1 (m, 2H), 2.18 (s, 3H), 3.18 (t, 4H), 3.35 (m, 1H), 3.41 (m, 2H), 3.75 (t, 4H), 5.1 (m, 1H), 7.12 (td, 1H), 7.21 (d, 1H), 7.37 (m, 3H), 7.41 (t, 2H), 7.5 (s, 1H), 7.57 (d, 1H), 7.78 (d, 1H), 9.83 (s, 1H), 10.1 (s, 1H); Mass Spectrum: M+H$^+$ 601.

The product so obtained was treated with trifluoroacetic acid using an analogous procedure to that described in the second paragraph of Example 25. There was thus obtained the title compound in 66% yield; NMR Spectrum: (DMSOd$_6$) 1.9 (m, 2H), 2.12 (s, 3H), 2.85 (m, 2H), 3.12 (t, 4H), 3.41 (m, 2H), 3.72 (t, 4H), 4.9 (m, 1H), 7.08 (m, 2H), 7.21 (d, 1H), 7.35 (m, 3H), 7.52 (m, 3H), 7.63 (m, 1H), 7.72 (m, 1H), 9.92 (s, 1H), 10.21 (s, 1H); Mass Spectrum: M+H$^+$ 501.

The 3-(1-tert-butoxycarbonylpyrrolidin-3-yloxy)benzoic acid used as a starting material was obtained as follows:

Using an analogous procedure to that described in the first paragraph of the portion of Example 25 which is concerned with the preparation of starting materials, N-tert-butoxycarbonyl-3-hydroxypyrrolidine (*J. Amer. Chem. Soc.*, 1982, 104, 5852–5853) was reacted with ethyl 3-hydroxybenzoate. The product so obtained was hydrolysed with sodium hydroxide using an analogous procedure to that described in the second paragraph of the portion of Example 25 which is concerned with the preparation of starting materials. There was thus obtained the required starting material; NMR Spectrum: (DMSOd$_6$) 1.38 (s, 9H), 2.06 (m, 2H), 3.1 (m, 3H), 3.55 (m, 1H), 5.03 (broad s, 1H), 7.18 (m, 1H), 7.38 (m,2H), 7.52 (d, 1H); Mass Spectrum: M+H$^+$ 308.

EXAMPLE 55

N-[2-methyl-5-(3-morpholinobenzamido)phenyl]-4-piperidin-4-yloxybenzamide

Using an analogous procedure to that described in the first paragraph of Example 25, 4-(1-tert-butoxycarbonylpiperidin-4-yloxy)benzoic acid was reacted with N-(3-amino-4-methylphenyl)-3-morpholinobenzamide. The crude reaction product was purified by column chromatography on silica using increasingly polar mixtures of isohexane and ethyl acetate as eluent. There was thus obtained N-[2-methyl-5-(3-morpholinobenzamido)phenyl]-4-(1-tert-butoxycarbonylpiperidin-4-yloxy)benzamide in 51% yield; Mass Spectrum: M+H$^+$ 615.

The product so obtained was treated with trifluoroacetic acid using an analogous procedure to that described in the second paragraph of Example 25. The reaction product was purified by column chromatography on silica using increasingly polar mixtures of methylene chloride and methanol as eluent. There was thus obtained the title compound in 62% yield; NMR Spectrum: (DMSOd$_6$) 1.53 (m, 2H), 1.95 (m, 2H), 2.16 (s, 3H), 2.7 (m, 2H), 3.03 (m, 2H), 3.18 (t, 4H), 3.73 (t, 4H), 4.57 (m, 1H), 7.05 (d, 2H), 7.13 (m, 1H), 7.2 (d, 2H), 7.35 (m, 2H), 7.44 (d, 1H), 7.56 (m, 1H), 7.79 (d, 1H), 7.94 (d, 2H), 9.7 (s, 1H), 10.1 (s, 1H); Mass Spectrum: M+H$^+$ 515.

The 4-(1-tert-butoxycarbonylpiperidin-4-yloxy)benzoic acid used as a starting material was obtained as follows:

Using an analogous procedure to that described in the first paragraph of the portion of Example 25 which is concerned with the preparation of starting materials, N-tert-butoxycarbonyl-4-hydroxypiperidine was reacted with ethyl 4-hydroxybenzoate and the crude reaction product was purified by column chromatography on silica using increasingly polar mixtures of methylene chloride and methanol as eluent. The product so obtained was hydrolysed with sodium hydroxide using an analogous procedure to that described in the second paragraph of the portion of Example 25 which is concerned with the preparation of starting materials. There was thus obtained the required starting material; NMR Spectrum: (DMSOd$_6$) 1.38 (s, 9H), 1.51 (m, 2H), 1.9 (m, 2H), 3.15 (m, 2H), 3.64 (m, 2H), 4.65 (m, 1H), 7.03 (d, 2H), 7.84 (d, 2H); Mass Spectrum: M+H$^+$ 322.

EXAMPLE 56

N-[2-methyl-5-(3-morpholinobenzamido)phenyl]-4-tetrahydrofuran-3-yloxybenzamide

Di-isopropyl azodicarboxylate (0.21 ml) was added to a stirred mixture of N-[2-methyl-5-(3-morpholinobenzamido) phenyl]-4-hydroxybenzamide (0.15 g), 3-hydroxytetrahydrofuran (0.31 g), triphenyl phosphine (0.275 g) and methylene chloride (5 ml) which had been cooled to 5° C. The resultant mixture was stirred at ambient temperature for 18 hours. The mixture was poured onto a pre-wetted (methylene chloride) ion-exchange column (isolute SCX 5 g column from International Sorbent Technology Limited) and eluted in turn with methylene chloride (40 ml), with methylene chloride (40 ml) containing 20% methanol and with methylene chloride containing 20% methanol and 3% of a saturated aqueous ammonium hydroxide solution. The product so obtained was further purified by column chromatography on silica using a 4:1 mixture of ethyl acetate and methanol as eluent. There was thus obtained the title compound as a solid (0.52 g); Mass Spectrum: M+H$^+$ 502.

EXAMPLE 57

N-(5-{3-[N-(2-methoxyethyl)-N-methylamino] benzamido}-2-methylphenyl)-3-piperidin-4-yloxybenzamide Using an analogous procedure to that described in the first paragraph of Example 25, 3-(1-tert-butoxycarbonylpiperidin-4-yloxy)benzoic acid was reacted with N-(3-amino-4-methylphenyl)-3-[N-(2-methoxyethyl)-N-methylamino]benzamide. The crude reaction product was purified by column chromatography on silica using increasingly polar mixtures of isohexane and ethyl acetate as eluent. There was thus obtained N-(5-{3-[N-(2-methoxyethyl)-N-methylamino]benzamido}-2-methylphenyl)-3-(1-tert-butoxycarbonylpiperidin-4-yloxy)benzamide in 63% yield; NMR Spectrum: (DMSOd$_6$) 1.38 (s, 9H), 1.54 (m, 2H), 2.19 (s, 3H), 2.96 (s, 3H), 3.2 (m, 5H), 3.5 (m, 4H), 3.65 (m, 2H), 4.63 (m, 1H), 6.88 (d, 1H), 7.2 (m, 5H), 7.41 (t, 3H), 7.57 (m, 3H), 7.79 (s, 1H), 9.83 (s, 1H), 10.06 (s, 1H); Mass Spectrum: M−C$_3$H$_7$$^+$ 561.

The product so obtained was treated with trifluoroacetic acid using an analogous procedure to that described in the second paragraph of Example 25. The reaction product was purified by column chromatography on silica using increasingly polar mixtures of methylene chloride and methanol as eluent. There was thus obtained the title compound in 62% yield; NMR Spectrum: (DMSOd$_6$) 1.53 (m, 2H), 1.95 (m, 2H), 2.16 (s, 3H), 2.7 (m, 2H), 3.03 (m, 2H), 3.18 (t, 4H), 3.73 (t, 4H), 4.57 (m, 1H), 7.05 (d, 2H), 7.13 (m, 1H), 7.2 (d, 2H), 7.35 (m, 2H), 7.44 (d, 1H), 7.56 (m, 1H), 7.79 (d, 1H), 7.94 (d, 2H), 9.7 (s, 1H), 10.1 (s, 1H); Mass Spectrum: M+H$^+$ 515.

The N-(3-amino-4-methylphenyl)-3-[N-(2-methoxyethyl)-N-methylamino]benzamide used as a starting material was obtained as follows:

A mixture of 3-bromobenzonitrile (3.64 g), (S)-(−)-2,2'-bis(diphenylphosphino)-1,1'-binaphthyl (0.279 g), tris (dibenzylidineacetone)dipalladium(0) (0.274 g) sodium tert-butoxide (3.86 g), and toluene (25 ml) was stirred at ambient temperature for 2 minutes. N-(2-methoxyethyl)-N-methylamine (2.57 ml) was added and the resultant mixture was stirred and heated to reflux for 18 hours. The mixture was cooled and partitioned between toluene and water. The organic phase was washed with a saturated aqueous sodium chloride solution, dried (MgSO$_4$) and evaporated. The residue was purified by column chromatography using a 9:1 mixture of isohexane and ethyl acetate as eluent. There was thus obtained 3-[N-(2-methoxyethyl)-N-methylamino] benzonitrile (2.51 g); NMR Spectrum: (CDCl$_3$) 2.98 (s, 3H), 3.36 (s, 3H), 3.5 (t, 4H), 6.9 (m, 3H), 7.23 (m, 1H).

A mixture of the material so obtained, 10N aqueous sodium hydroxide solution (6.5 ml), water (6.5 ml) and n-butanol (15 ml) was stirred and heated to reflux for 28 hours. The mixture was evaporated and the residue was partitioned between methylene chloride and dilute aqueous hydrochloric acid. The organic extracts were dried (MgSO$_4$) and evaporated to leave an oil which on trituration under isohexane formed a solid. There was thus obtained 3-[N-(2-methoxyethyl)-N-methylamino]benzoic acid (1.42 g); NMR Spectrum: (DMSOd$_6$) 2.9 (s, 3H), 3.22 (m, 3H), 3.43 (m, 4H), 6.92 (m, 1H), 7.2 (m, 3H).

A mixture of the material so obtained, oxalyl chloride (0.67 ml) and methylene chloride (70 ml) was stirred at ambient temperature for 3 hours. The resultant mixture was evaporated. The material so obtained was dissolved in methylene chloride (70 ml) and added to a stirred mixture of 4-methyl-3-nitroaniline (0.82 g), triethylamine (1.58 ml) and methylene chloride (70 ml). The mixture was stirred at ambient temperature for 18 hours. The mixture was then washed in turn with water, with a saturated aqueous sodium bicarbonate solution and with water, dried (MgSO$_4$) and evaporated. The residue was purified by column chromatography on silica using increasingly polar mixtures of methylene chloride and methanol as eluent. There was thus obtained N-(4-methyl-3-nitrophenyl)-3-[N-(2-methoxyethyl)-N-methylamino]benzamide as a solid (1.11 g); NMR Spectrum: (DMSOd$_6$) 2.98 (s, 3H), 2.45(s, 3H), 3.4 (s, 3H), 3.52 (m, 4H), 6.91 (d, 1H), 7.18 (s, 2H), 7.26 (t, 1H), 7.43 (d, 1H), 7.98 (m, 1H), 8.52 (s, 1H), 10.41 (s, 1H).

A mixture of the material so obtained, 10% palladium-on-carbon catalyst (0.15 g) and methanol (150 ml) was stirred under an atmosphere pressure of hydrogen at ambient temperature for 18 hours. The catalyst was filtered off and the filtrate was evaporated. There was thus obtained the required starting material as a solid (0.86 g); NMR Spectrum: (DMSOd$_6$) 2.0 (s, 3H), 2.96 (s, 3H), 3.25 (s, 3H), 3.51 (m, 4H), 4.79 (s, 2H), 6.82 (m, 3H), 7.1 (m, 3H), 7.23 (m, 1H), 9.73 (s, 1H); Mass Spectrum: M+H$^+$ 314.

EXAMPLE 58

N-(5-{3-[N-(2-methoxyethyl)-N-methylamino] benzamido}-2-methylphenyl)-3-pyrrolidin-3-yloxybenzamide Using an analogous procedure to that described in the first paragraph of Example 25, 3-(1-tertbutoxycarbonylpyrrolidin-3-yloxy)benzoic acid was reacted with N-(3-amino-4-methylphenyl)-3-[N-(2-methoxyethyl)-N-methylamino]benzamide to give N-(5-{3-[N-(2-methoxyethyl)-N-methylamino]benzamido}-2-methylphenyl)-3-(1-tert-butoxycarbonylpyrrolidin-3-yloxy)benzamide in 59% yield; NMR Spectrum: (DMSOd$_6$) 1.39 (s, 9H), 2.08 (m, 2H), 2.18 (s, 3H), 2.96 (s, 3H), 3.22 (s, 3H),3.25 (m, 2H), 3.52 (m, 6H), 5.07 (s, 1H), 6.87 (d, 1H), 7.2 (m, 5H), 7.43 (t, 1H), 7.55 (m, 3H), 7.79 (s, 1H), 9.86 (s, 1H), 10.06 (s, 1H); Mass Spectrum: M–C$_3$H$_7$$^+$ 547.

The product so obtained was treated with trifluoroacetic acid using an analogous procedure to that described in the second paragraph of Example 25. There was thus obtained the title compound in 26% yield; NMR Spectrum: (DMSOd$_6$) 1.77 (m, 1H), 2.02 (m, 1H), 2.18 (s, 3H), 2.78 (m, 2H), 2.95 (s, 3H), 3.06 (m, 2H), 4.92 (m, 4H), 6.87 (d, 1H), 7.2 (m, 5H), 7.47 (m, 4H), 7.79 (s, 1H), 9.84 (s, 1H), 10.06 (s, 1H); Mass Spectrum: M+H$^+$ 503.

EXAMPLE 59

N-(5-{3-[N-(2-methoxyethyl)-N-methylamino]benzamido}-2-methylphenyl)-3-(4-methylpiperazin-1-ylmethyl)benzamide A mixture of N-methylpiperazine (3 ml) and N-(5-{3-[N-(2-methoxyethyl)-N-methylamino]benzamido}-2-methylphenyl)-3-chloromethylbenzamide (0.21 g) was stirred and heated to 80° C. for 3 hours. The mixture was cooled to ambient temperature and partitioned between ethyl acetate and water. The organic phase was evaporated and the residue was triturated under diethyl ether. There was thus obtained the title compound (0.17 g); NMR Spectrum: (DMSOd$_6$) 2.17 (d, 6H), 2.33 (m, 8H), 2.98 (s, 3H), 3.23 (s, 3H), 3.50 (m, 6H), 6.87 (d, 1H), 7.2 (m, 4H), 7.46 (m, 2H), 7.57 (m, 1H), 7.8 (s, 1H), 7.86 (m, 2H), 9.87 (s, 1H), 10.06 (s, 1H); Mass Spectrum: M+H$^+$ 530.

The N-(5-{3-[N-(2-methoxyethyl)-N-methylamino]benzamido}-2-methylphenyl)-3-chloromethylbenzamide used as a starting material was obtained as follows Using an analogous procedure to that described in Example 37, 3-chloromethylbenzoyl chloride was reacted with N-(3-amino-4-methylphenyl)-3-[N-(2-methoxyethyl)-N-methylamino]benzamide. The reaction mixture was washed in turn with water, and a saturated aqueous sodium bicarbonate solution, dried (MgSO$_4$) and evaporated. The residue purified by column chromatography on silica using increasingly polar mixtures of isohexane and ethyl acetate as eluent. There was thus obtained the required starting material as a solid in 74% yield which was used without further purification.

EXAMPLE 60

N-[2-methyl-5-(3-morpholinobenzamido)phenyl]-3-methanesulphonylaminobenzamide

Methanesulphonyl chloride (0.16 ml) was added to a stirred mixture of N-[2-methyl-5-(3-morpholinobenzamido)phenyl]-3-aminobenzamide (0.765 g), pyridine (0.29 ml) and methylene chloride (30 ml) and the resultant mixture was stirred at ambient temperature for 18 hours. A second portion (0.158 ml) of methanesulphonyl chloride was added and the resultant mixture was stirred at ambient temperature for a further 18 hours. The reaction mixture was washed with water, dried (MgSO$_4$) and evaporated. The residue was triturated under diethyl ether. The solid so obtained was dried under vacuum at 60° C. There was thus obtained the title compound (0.97 g); NMR Spectrum: (DMSOd$_6$) 2.2 (s, 3H), 3.03 (s, 3H), 3.2 (t, 4H), 3.74 (t, 4H), 7.17 (m, 1H), 7.23 (d, 1H), 7.4 (m, 5H), 7.59 (m, 1H), 7.7 (d, 1H), 7.8 (m, 2H), 9.93 (d, 2H), 10.14 (s, 1H); Mass Spectrum: M+H$^+$ 509.

The N-[2-methyl-5-(3-morpholinobenzamido)phenyl]-3-aminobenzamide used as a starting material was prepared as follows:

3-Nitrobenzoyl chloride (1.31 g) was added to a mixture of N-(3-amino-4-methylphenyl)-3-morpholinobenzamide (2 g), triethylamine (1.79 ml) and methylene chloride (40 ml) and the resultant mixture was stirred at ambient temperature for 18 hours. The precipitate was isolated, washed in turn with methylene chloride and diethyl ether and dried under vacuum at 60° C. There was thus obtained N-[2-methyl-5-(3-morpholinobenzamido)phenyl]-3-nitrobenzamide (0.95 g); m.p. 247–248° C.; NMR Spectrum: (DMSOd$_6$) 2.22 (s, 3H), 3.2 (t, 4H), 3.75 (t, 4H), 7.13 (m, 1H), 7.24 (d, 1H), 7.35 (m, 2H), 7.44 (d, 1H), 7.59 (m, 1H), 7.84 (m, 2H), 8.43 (m, 2H), 8.79 (d, 1H), 10.13 (s, H), 10.3 (s, 1H); Mass Spectrum: M–H$^-$ 459.

10% Palladium-on-carbon (0.13 g) was added to a solution of the material so obtained in methanol (150 ml) and the mixture was stirred under an atmosphere of hydrogen. After cessation of hydrogen uptake, the catalyst was removed by filtration and the filtrate was evaporated. The residue was dried under vacuum at 60° C. There was thus obtained the required starting material (0.77 g); m.p. 171–172° C.; NMR Spectrum: (DMSOd$_6$) 2.18 (s, 3H), 3.14 (t, 4H), 3.26 (s, 2H), 3.73 (t, 4H), 6.72 (m,1H), 7.11 (m, 4H), 7.19 (d, 1H), 7.35 (m, 2H), 7.43 (d, 1H), 7.56 (m , 1H); 7.76 (d, 1H), 9.63 (s, 1H), 10.1 (s, 1H); Mass Spectrum: M+H$^+$ 431.

EXAMPLE 61

N-[2-methyl-5-(3-morpholinobenzamido)phenyl]-3-(N-methylmethanesulphonylamino)benzamide Methyl iodide (0.023 ml) was added to a mixture of N-[2-methyl-5-(3-morpholinobenzamido)phenyl]-3-methanesulphonylaminobenzamide (0.17 g), caesium carbonate (0.121 g) and DMF (10 ml) and the resultant mixture was stirred and heated to 50° C. for 72 hours. The reaction mixture was poured into water (200 ml). The precipitate was isolated, washed in turn with water and diethyl ether and dried under vacuum at 60° C. There was thus obtained the title compound (0.1 g); m.p. 208–209° C.; NMR Spectrum: (DMSOd$_6$) 2.19 (s, 3H), 3.0 (s, 3H), 3.18 (t, 4H), 3.75 (t, 4H), 7.13 (m, 1H), 7.23 (d, 1H), 7.36 (m, 2H), 7.45 (d, 1H), 7.59 (m, 3H), 7.81 (d, 1H), 7.91 (d, 1H), 7.99 (d, 1H), 9.98 (s, 1H), 10.12 (s, 1H); Mass Spectrum: M+H$^+$523.

EXAMPLE 62

N-[2-methyl-5-(3-morpholinobenzamido)phenyl]-3-(N-ethylmethanesulphonylamino)benzamide Using an analogous procedure to that described in Example 61, N-[2-methyl-5-(3-morpholinobenzamido)phenyl]-3-methanesulphonylaminobenzamide was reacted with ethyl iodide to give the title compound in 64% yield; m.p. 192–193° C.; NMR Spectrum: (DMSOd$_6$) 1.05 (t, 3H), 2.21 (s, 3H), 3.16 (t, 4H),3.73 (m, 6H), 7.13 (m, 1H) 7.23 (d, 1H), 7.36 (m, 2H), 7.43 (d, 1H), 7.58 (m, 3H), 7.81 (d, 1H), 7.95 (m, 2H), 7.99 (d, 1H), 10.0 (s, 1H), 10.12 (s, 1H); Mass Spectrum: M+H$^+$537.

EXAMPLE 63

N-[5-(3-dimethylaminobenzamido)-2-methylphenyl]-3-chloromethylbenzamide

Triethylamine (1.55 ml) was added to a stirred mixture of N-(3-amino-4-methylphenyl)-3-dimethylaminobenzamide (3.0 g), 3-chloromethylbenzoyl chloride (2.76 g) and methylene chloride (50 ml) and the reaction mixture was stirred at ambient temperature for 16 hours. The mixture was evaporated and the residue was triturated under water. The solid so obtained was isolated, washed in turn with a saturated aqueous sodium bicarbonate solution, water and isohexane and dried under vacuum at 55° C. There was thus obtained the title compound (4.8 g); NMR Spectrum: (DMSOd$_6$) 2.19 (s, 3H), 2.96 (s, 6H), 4.84 (s, 2H), 6.9 (d, 1H), 7.26 (m, 3H), 7.5–7.7 (m, 3H), 7.8–8.1 (m, 4H), 9.97 (s, 1H), 10.09 (s, 1H); Mass Spectrum: M−H⁻420.

EXAMPLE 64

N-[5-(3-ditethylaminobenzamido)-2-methylphenyl]-4-chloromethylbenzamide

4-Chloromethylbenzoyl chloride was reacted with N-(3-amino-4-methylphenyl)-3-dimethylaminobenzamide using an analogous procedure to that described in Example 37 except that the reaction product was triturated under water rather than under 2N aqueous hydrochloric acid solution. There was thus obtained the title compound; NMR Spectrum: (DMSOd$_6$) 2.19 (s, 3H), 2.95 (s, 6H), 4.28 (s, 2H), 6.9 (d, 1H), 7.21 (m, 3H), 7.29 (d, 1H), 7.58 (d, 3H), 7.8 (s, 1H), 7.96 (d, 2H), 9.9 (s, 1H), 10.08 (s, 1H); Mass Spectrum: M−H⁻420.

EXAMPLE 65

N-[2-methyl-5-(3-morpholinobenzamido)phenyl]-3-chloromethylbenzamide

Using an analogous procedure to that described in Example 63, 3-chloromethylbenzoyl chloride was reacted with N-(3-amino-4-methylphenyl)-3-morpholinobenzamide. There was thus obtained the title compound in 98% yield: NMR Spectrum: (DMSOd$_6$) 2.19 (s, 3H), 3.17 (m, 4H), 3.75 (m, 4H), 4.85 (s, 2H), 7.13 (d, 1H), 7.22 (d, 1H), 7.34 (m, 2H), 7.44 (s, 1H), 7.54 (m, 2H), 7.65 (d, 1H), 7.79 (s, 1H), 7.95 (d, 1H), 8.03 (s, 1H), 9.96 (s, 1H), 10.12 (s, 1H); Mass Spectrum: M+H⁺464.

EXAMPLE 66

N-[5-(4-fluoro-3-trifluoromethylbenzamido)-2-methylphenyl]-4-diethylaminomethylbenzamide Oxalyl chloride (0.1 ml) was added to a stirred mixture of 4-fluoro-3-trifluoromethylbenzoic acid (0.2 g), DMF (3 drops) and methylene chloride (8 ml) and the mixture was stirred at ambient temperature for 3 hours. The solvent was evaporated. The residue was dissolved in pyridine (5 ml) and a solution of N-(5-amino-2-methylphenyl)-4-diethylaminomethylbenzamide (0.2 g) in methylene chloride (4 ml) was added. The resultant mixture was stirred at ambient temperature for 3 days. The mixture was evaporated and the residue was triturated under water. The resultant solid was washed with a saturated aqueous solution of sodium bicarbonate and dried under vacuum at 55° C. to give the title compound (0.3 g); NMR Spectrum: (DMSOd$_6$) 1.23 (broad s, 6H), 2.21 (s, 3H), 3.03 (broad s, 4H), 3.3 (m, 2H), 7.26 (d, 1H), 7.58 (d, 1H), 7.7 (m, 3H), 7.82 (s, 1H), 8.04 (d, 2H), 8.35 (d, 2H), 9.96 (s, 1H), 10.48 (s, 1H); Mass Spectrum: M+H⁺502.

EXAMPLE 67

N-[5-(3-fluoro-5-morpholinobenzamido)-2-methylphenyl]-4-diethylaminomethylbenzamide A mixture of N-[5-(3,5-difluorobenzamido)-2-methylphenyl]-4-diethylaminomethylbenzamide (0.069 g) and morpholine (3 ml) was stirred and heated to 100° C. for 6 days. The mixture was cooled to ambient temperature and poured into water. The resultant solid was isolated, washed in turn with water and diethyl ether and dried under vacuum at 40° C. There was thus obtained the title compound (0.033 g); NMR Spectrum: (DMSOd$_6$) 0.98 (t, 6H), 2.2 (s, 3H), 2.46–2.49 (m, 4H), 3.20–3.24 (m, 4H), 3.58 (s, 2H), 3.72–3.75 (m, 4H), 6.95 (d, 1H), 7.14 (d, 1H), 7.21 (d, 1H), 7.3 (s, 1H), 7.45 (s, 2H), 7.58 (d, 1H), 7.78 (s, 1H), 7.91 (d, 2H), 9.82 (s, 1H), 10.15 (s, 1H); Mass Spectrum: M+H⁺519.

The N-[5-(3,5-difluorobenzamido)-2-methylphenyl]-4-diethylaminomethylbenzamide used as a starting material was obtained as follows:

3,5-Difluorobenzoyl chloride (0.088 g) was added to a stirred mixture of N-(5-amino-2-methylphenyl)-4-diethylaminomethylbenzamide (0.14 g), triethylamine (0.12 g) and methylene chloride (5 ml) and the mixture was stirred at ambient temperature for 16 hours. The mixture was washed with a saturated aqueous sodium bicarbonate solution. The organic phase was evaporated and the residue was triturated under a mixture of ethyl acetate and diethyl ether. There was thus obtained the required starting material (0.115 g); NMR Spectrum: (DMSOd$_6$) 0.98 (t, 6H), 2.2 (s, 3H), 2.43–2.49 (m, 4H), 3.59 (s, 2H), 7.24 (d, 1H), 7.43–58 (m, 4H), 7.68 (d, 2H), 7.81 (s, 1H), 7.92 (d, 2H), 9.83 (s, 1H), 10.44 (s, 1H); Mass Spectrum: M+H⁺452.

EXAMPLE 68

N-[5-(3-fluoro-5-pyrrolidin-1-ylbenzamido)-2-methylphenyl]-4-diethylaminomethylbenzamide Using an analogous procedure to that described in Example 67 except that the reaction mixture was heated to 100° C. for 16 hours rather than for 6 days, N-[5-(3,5-difluorobenzamido)-2-methylphenyl]-4-diethylaminomethylbenzamide was reacted with pyrrolidine. There was thus obtained the title compound in 81% yield; NMR Spectrum: (DMSOd$_6$) 0.98 (t, 6H), 1.95–2.0 (m, 4H), 2.2 (s, 3H), 2.4–2.5 (m, 4H), 3.3. (m, 4H), 3.6 (s, 2H), 6.4–6.5 (m, 1H), 6.85–6.95 (m, 2H), 7.2 (d, 2H), 7.45 (d, 2H), 7.58 (m, 1H), 7.8 (m, 1H), 7.95 (d, 2H), 9.8 (s, 1H), 10.1 (broad s, 1H); Mass Spectrum: M+H⁺503.

EXAMPLE 69

N-[5-(3-fluoro-5-piperidinobenzamido)-2-methylphenyl]-4-diethylaminomethylbenzamide Using an analogous procedure to that described in Example 67 except that the reaction mixture was heated to 100° C. for 16 hours rather than for 6 days, N-[5-(3,5-difluorobenzamido)-2-methylphenyl]-4-diethylaminomethylbenzamide was reacted with piperidine. There was thus obtained the title compound in 83% yield; NMR Spectrum: (DMSOd$_6$) 0.98 (t, 6H), 1.3–1.7 (m, 8H), 2.2 (s, 3H), 2.4–2.5 (m, 2H), 3.2–3.4 (m, 4H), 6.85–6.95 (m, 1H), 7.0–7.1 (m, 1H), 7.2–7.3 (m, 2H), 7.45 (d, 2H), 7.5–7.6 (m, 1H), 7.8 (m, 1H), 7.9 (d, 2H), 9.8 (s, 1H), 10.13 (broad s, 1H); Mass Spectrum: M+H⁺517.

EXAMPLE 70

N-[2-methyl-5-(5-morpholino-2-nitrobenzamido)phenyl]-4-diethylaminomethylbenzamide Using an analogous procedure to that described in Example 67 except that the reaction mixture was heated to 105° C. for 16 hours rather than to 100° C. for 6 days, N-[5-(5-chloro-2-nitrobenzamido)-2-methylphenyl]-4-diethylaminomethylbenzamide was reacted with morpholine. The solid so obtained was dissolved in methylene chloride and the solution was washed with a saturated aqueous sodium bicarbonate solution. The organic solution was dried (MgSO$_4$) and evaporated. There was thus obtained the title compound in 64% yield; NMR Spectrum: (DMSOd$_6$) 0.98 (t, 6H), 2.2 (s, 3H), 2.4–2.6 (m, 4H), 3.4–3.5 (m, 4H), 3.6 (s, 2H), 3.7–3.8 (m, 4H), 7.0–7.1 (m, 2H), 7.2 (m, 1H), 7.4–7.5 (m, 2H), 7.7 (m, 1H), 7.9 (d, 2H), 8.05 (d, 1H), 9.85 (s, 1H), 10.38 (broad s, 1H); Mass Spectrum: M+H$^+$546.

The N-[5-(5-chloro-2-nitrobenzamido)-2-methylphenyl]-4-diethylaminomethylbenzamide used as a starting material was obtained as follows:

Using an analogous procedure to that described in the portion of Example 67 which is concerned with the preparation of starting materials, 5-chloro-2-nitrobenzoyl chloride (obtained by the reaction of 5-chloro-2-nitrobenzoic acid and oxalyl chloride) was reacted with N-(5-amino-2-methylphenyl)-4-diethylaminomethylbenzamide to give the required starting material in 69% yield; Mass Spectrum: M+H$^+$495.

EXAMPLE 71

N-[5-(2-amino-3-morpholinobenzamido)-2-methylphenyl]-4-diethylaminomethylbenzamide A mixture of N-[2-methyl-5-(3-morpholino-2-nitrobenzamido)phenyl]-4-diethylaminomethylbenzamide (1.21 g), iron powder (1.24 g), glacial acetic acid (0.44 ml), water (2.2 ml) and ethanol (22.2 ml) was stirred and heated to 95° C. for 9 hours. The resultant mixture was cooled to ambient temperature and basified to pH9 by the addition of a saturated aqueous sodium bicarbonate solution. The mixture was filtered and the filtrate was evaporated. The residue was partitioned between ethyl acetate and a saturated aqueous sodium bicarbonate solution. The organic phase was dried (MgSO$_4$) and evaporated. There was thus obtained the title compound as a solid (0.826 g); Mass Spectrum: M+H$^+$ 516.

The N-[2-methyl-5-(3-morpholino-2-nitrobenzamido)phenyl]-4-diethylaminomethylbenzamide used as a starting material was obtained as follows:

Using an analogous procedure to that described in the portion of Example 67 which is concerned with the preparation of starting materials, 3-chloro-2-nitrobenzoyl chloride (obtained by the reaction of 3-chloro-2-nitrobenzoic acid and oxalyl chloride) was reacted with N-(5-amino-2-methylphenyl)-4-diethylaminomethylbenzamide. There was thus obtained N-[5-(3-chloro-2-nitrobenzamido)-2-methylphenyl]-4-diethylaminomethylbenzamide in 55% yield; NMR Spectrum: (DMSOd$_6$) 0.98 (t, 6H), 2.2 (s, 3H), 2.4–2.5 (m, 4H), 3.6 (s, 2H), 7.2–7.25 (m, 1H), 7.4–7.45 (m, 3H), 7.7–7.8 (m, 2H), 7.9–8.0 (m, 4H), 9.8 (s, 1H); Mass Spectrum: M+H$^+$495.

Using an analogous procedure to that described in Example 67 except that the reaction mixture was heated to 100° C. for 16 hours rather than for 6 days, N-[5-(3-chloro-2-nitrobenzamido)-2-methylphenyl]-4-diethylaminomethylbenzamide was reacted with morpholine. The solid so obtained was dissolved in methylene chloride and the solution was washed with a saturated aqueous sodium bicarbonate solution. The organic solution was dried (MgSO$_4$) and evaporated. There was thus obtained N-[2-methyl-5-(3-morpholino-2-nitrobenzamido)phenyl]-4-diethylaminomethylbenzamide in 73% yield; NMR Spectrum: (DMSOd$_6$) 0.98 (t, 6H), 2.2 (s, 3H), 2.4–2.5 (m, 4H), 2.9–2.95 (m, 4H), 3.6 (s, 2H), 3.6–3.7 (m, 4H), 7.2–7.25 (m, 1H), 7.4–7.45 (m, 3H), 7.5–7.6 (m, 1H), 7.6–7.7 (m, 2H), 7.75 (m, 1H), 7.9–7.95 (d, 2H), 9.8 (s, 1H), 10.62 (broad s, 1H); Mass Spectrum: M+H$^+$546.

EXAMPLE 72

N-[5-(5-cyclohexylvaleramido)-2-methylphenyl]-4-(diethylaminomethyl)benzamide

Using an analogous procedure to that described in Example 22 except that the step of washing the reaction mixture with a 1M aqueous citric acid solution was omitted, N-(5-amino-2-methylphenyl)-4-diethylaminomethylbenzamide was reacted with 5-cyclohexylvaleryl chloride (obtained by the reaction of 5-cyclohexylvaleric acid and oxalyl chloride using a conventional procedure) to give the title compound; Mass Spectrum: M+H$^+$478.

EXAMPLE 73

N-[2-methyl-5-(3-morpholinobenzamido)phenyl]-3-(N-methylhomopiperidin-4-yloxy)benzamide As described hereinbefore in Example 7, 2-(2-chloroethyl)-N-methylpyrrolidine was reacted with N-[2-methyl-5-(3-morpholinobenzamido)phenyl]-3-hydroxybenzamide and the reaction product was purified by column chromatography on silica using a 9:1 mixture of methylene chloride and methanol as eluent. There was thus obtained N-[2-methyl-5-(3-morpholinobenzamido)phenyl]-3-[2-(N-methylpyrrolidin-2-yl)ethoxy]benzamide (Example 7, Compound No. 32). On further elution an isomeric by-product was obtained. There was thus obtained the title compound NMR Spectrum: (DMSOd$_6$) 1.6 (m, 1H), 1.79 (m, 3H), 2.04 (m, 2H), 2.17 (s, 3H), 2.24 (s, 3H), 2.52 (m, 4H), 3.18 (t, 4H), 3.76 (t, 4H), 4.66 (m, 1H), 7.1 (m, 2H), 7.21 (d, 1H), 7.4 (m, 4H), 7.5 (d, 1H), 7.56 (m, 1H), 7.78 (d, 1H), 9.83 (s, 1H), 10.11 (s, 1H); Mass Spectrum: M+H$^+$543.

EXAMPLE 74

N-{5-[3-fluoro-5-(3-pyrrolin-1-yl)benzamido]-2-methylphenyl}-4-diethylaminomethylbenzamide Using an analogous procedure to that described in Example 67 except that the reaction mixture was heated to 100° C. for 16 hours rather than for 6 days, N-[5-(3,5-difluorobenzamido)-2-methylphenyl]-4-diethylaminomethylbenzamide was reacted with 3-pyrroline. There was thus obtained the title compound in 58% yield; NMR Spectrum: (DMSOd$_6$) 1.0 (t, 6H), 2.2 (s, 3H), 2.5 (m, 4H), 3.6 (s, 2H), 4.15 (s, 4H), 6.05 (m, 1H), 6.45–6.55 (m, 1H), 6.9 (s, 1H), 6.97 (m, 1H), 7.22 (m, 1H), 7.45 (d, 2H), 7.57 (m, 1H), 7.8 (m, 1H), 7.95 (d, 2H), 9.8 (s, 1H), 10.12 (broad s, 1H); Mass Spectrum: M+H$^+$501.

EXAMPLE 75

N-[2-methyl-5-(3-morpholinobenzamido)phenyl]-3-tetrahydrofuran-3-yloxybenzamide 1-(3-Dimethylaminopropyl)-3-ethylcarbodiimide hydrochloride (0.165 g) was added to a stirred mixture of 3-(tetrahydrofuran-3-yloxy)benzoic acid (0.15 g), 1-hydroxybenzotriazole (0.146 g) and DMF (5 ml) which had been cooled to 0° C. The reaction mixture was stirred at 0° C. for 5 minutes and a solution of N-(3-amino-4-methylphenyl)-3-morpholinobenzamide (0.224 g) in DMF (1 ml) was added. The reaction mixture was allowed to come to ambient temperature and was stirred for 16 hours. The reaction mixture was poured into water and the resultant solid was isolated and purified by column chromatography on silica using a 99:1 mixture of methylene chloride and methanol as eluent. There was thus obtained the title compound (0.228 g); NMR Spectrum: (DMSOd$_6$) 1.99 (m, 1H), 2.18 (s, 3H), 2.25 (m, 1H), 3.17 (t, 4H), 3.72 (t, 4H), 3.88 (m, 4H), 5.13 (m, 1H), 7.11 (m, 2H), 7.21 (d, 1H), 7.39 (m, 5H), 7.56 (m, 2H), 7.79 (m, 2H), 9.83 (s, 1H), 10.11 (s, 1H); Mass Spectrum: M+H$^+$502.

The 3-(tetrahydrofuran-3-yloxy)benzoic acid used as a starting material was obtained as follows:

Diethyl azodicarboxylate (2.09 g) was added to a stirred mixture of ethyl 3-hydroxybenzoate (1.662 g), 3-hydroxytetrahydrofuran (0.881 g), triphenylphosphine (3.41 g) and THF (40 ml) which had been cooled to 0° C. The resultant mixture was allowed to warm to ambient temperature and was stirred for 18 hours. The mixture was evaporated and the residue was triturated under a 9:1 mixture of hexane and ethyl acetate. The solid triphenylphosphine oxide so formed was filtered off. The filtrate was evaporated and the residue was purified by column chromatography on silica using a 99:1 mixture of methylene chloride and methanol as eluent. There was thus obtained ethyl 3-(tetrahydrofuran-3-yloxy)benzoate (1.56 g); NMR Spectrum: (DMSOd$_6$) 1.27 (t, 3H), 1.93 (m, 1H), 2.22 (m, 1H), 3.82 (m, 4H), 4.27 (m, 2H), 5.08 (m, 1H), 7.19 (m, 1H), 7.42 (m, 2H), 7.52 (d, 1H).

Sodium hydroxide solution (1N; 10.22 ml) was added to a solution in ethanol (20 ml) of the ester so obtained and the mixture was stirred at ambient temperature for 48 hours. The mixture was evaporated and the residue was partitioned between ethyl acetate and a 1N aqueous hydrochloric acid solution. The organic phase was washed with water, dried (MgSO$_4$) and evaporated to give the required starting material as a solid (0.3 g) NMR Spectrum: (DMSOd$_6$) 1.9 (m, 1H), 2.2 (m, 1H), 3.8 (m, 4H), 5.03 (m, 1H), 7.07 (m, 1H), 7.36 (t, 1H), 7.41 (s, 1H), 7.52 (d, 1H).

EXAMPLE 76

N-[2-methyl-5-(3-morpholino-5-trifluoromethylbenzamido)phenyl]-3-piperidin-4-yloxybenzamide Using an analogous procedure to that described in the first paragraph of Example 50, 3-(1-tert-butoxycarbonylpiperidin-4-yloxy)benzoic acid was reacted with N-(3-amino-4-methylphenyl)-3-morpholino-5-trifluoromethylbenzamide to give N-[2-methyl-5-(3-morpholino-5-trifluoromethylbenzamido)phenyl]-3-(1-tert-butoxycarbonylpiperidin-4-yloxy)benzamide in 77% yield; NMR Spectrum: (DMSOd$_6$) 1.37 (s, 9H), 1.55 (m, 2H), 1.95 (m, 2H), 2.19 (s, 3H), 3.2 (m, 2H), 3.25 (t, 4H), 3.63 (m, 2H), 3.77 (t, 4H), 4.63 (m, 1H), 7.18 (m, 1H), 7.22 (d, 1H), 7.37 (s, 1H), 7.41 (t, 1H), 7.5 (s, 2H), 7.57 (m, 1H), 7.62 (s, 1H), 7.7 (s, 1H), 7.78 (d, 1H), 9.83 (s, 1H), 10.31 (m, 1H); Mass Spectrum: M+H$^+$683.

The product so obtained was treated with trifluoroacetic acid using an analogous procedure to that described in the second paragraph of Example 50. There was thus obtained the title compound in 62% yield; NMR Spectrum: (DMSOd$_6$) 1.38 (m, 2H), 1.85 (m, 2H), 2.16 (s, 3H), 2.45 (m, 2H), 2.88 (m, 2H), 3.22 (t, 4H), 3.7 (t, 4H), 4.4 (s, 1H), 7.05 (d, 1H), 7.12 (d, 1H), 7.26 (s, 1H), 7.31 (t, 1H), 7.47 (m, 3H), 7.6 (s, 1H), 7.7 (d, 2H), 10.15 (m, 2H); Mass Spectrum: M+H$^+$583.

The N-(3-amino-4-methylphenyl)-3-morpholino-5-trifluoromethylbenzamide used as a starting material was obtained as follows:

Ethyl 3-morpholino-5-trifluoromethylbenzoate was prepared from ethyl 3-fluoro-5-trifluoromethylbenzoate by the method described by Brown et al., *Tetrahedron Lett.*, 1999, 40, 1219. The material so obtained compound gave the following data: NMR Spectrum: (CDCl$_3$) 1.36 (t, 3H), 3.19 (t, 4H), 3.81 (t, 4H), 4.34 (m, 2H), 7.22 (d, 1H), 7.76 (s, 1H).

A mixture of ethyl 3-morpholino-5-trifluoromethylbenzoate (0.67 g), 1N aqueous sodium hydroxide solution (3.3 ml) and ethanol (6 ml) was stirred and heated to reflux for 15 minutes and then left to stand for 16 hours. The ethanol was evaporated and the residue was dissolved in water (6 ml). Hydrochloric acid (1 M, 3.3 ml) was added and the resultant solid was isolated, washed with water and dried. There was thus obtained 3-morpholino-5-trifluoromethylbenzoic acid as a solid (0.464 g); NMR Spectrum: (DMSOd$_6$) 3.25 (t, 4H), 3.73 (t, 4H), 7.4 (s, 1H), 7.53 (s, 1H), 7.65 (s, 1H), 13.3 (s, 1H).

A solution of 3-morpholino-5-trifluoromethylbenzoyl chloride (11.43 g; obtained by the reaction of the benzoic acid with oxalyl chloride using a conventional procedure) in methylene chloride (200 ml) was added to a stirred mixture of 4-methyl-3-nitroaniline (5.47 g), triethylamine (10 ml) and methylene chloride (200 ml). The resultant mixture was stirred at ambient temperature for 18 hours. The reaction mixture was washed with water and with a saturated aqueous sodium bicarbonate solution, dried (MgSO$_4$) and evaporated. The resultant solid was stirred with diethyl ether (300 ml) for 16 hours. The resultant solid was collected, washed with diethyl ether and dried. There was thus obtained N-(4-methyl-3-nitrophenyl)-3-morpholino-5-fluorobenzamide as a solid (10.4 g); NMR Spectrum: (CDCl$_3$) 2.58 (s, 3H), 3.22 (t, 4H), 3.83 (t, 4H), 7.21 (s, 2H), 7.32 (d, 1H), 7.41 (s, 1H), 7.58 (s, 1H),7.82 (m, 1H), 8.02 (s, 1H), 8.23 (d, 1H).

The compound so obtained was dissolved in ethyl acetate (500 ml) and hydrogenated over 10% palladium-on-carbon catalyst (1.1 g) under 3 atmospheres pressure of hydrogen until the uptake of hydrogen ceased. The catalyst was removed by filtration and the filtrate was evaporated. The residue was triturated under ethyl acetate to give the required starting material (8.1 g); NMR Spectrum: (CDCl$_3$) 2.01 (s, 3H), 3.23 (t, 4H), 3.75 (t, 4H), 4.81 (s, 2H), 6.77 (m, 1H), 6.83 (d, 1H), 7.02 (d, 1H), 7.25 (s, 1H), 7.58 (s, 1H), 7.63 (s, 1H), 9.9 (s, 1H).

EXAMPLE 77

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
| --- | --- |
| Compound X | 100 |
| Lactose Ph.Eur | 182.75 |

-continued

|   |   | mg/tablet |
|---|---|---|
|   | Croscarmellose sodium | 12.0 |
|   | Maize starch paste (5% w/v paste) | 2.25 |
|   | Magnesium stearate | 3.0 |

| (b) | Tablet II | mg/tablet |
|---|---|---|
|   | Compound X | 50 |
|   | Lactose Ph.Eur | 223.75 |
|   | Croscarmellose sodium | 6.0 |
|   | Maize starch | 15.0 |
|   | Polyvinylpyrrolidone (5% w/v paste) | 2.25 |
|   | Magnesium stearate | 3.0 |

| (c) | Tablet III | mg/tablet |
|---|---|---|
|   | Compound X | 1.0 |
|   | Lactose Ph.Eur | 93.25 |
|   | Croscarmellose sodium | 4.0 |
|   | Maize starch paste (5% w/v paste) | 0.75 |
|   | Magnesium stearate | 1.0 |

| (d) | Capsule | mg/capsule |
|---|---|---|
|   | Compound X | 10 |
|   | Lactose Ph.Eur | 488.5 |
|   | Magnesium | 1.5 |

| (e) | Injection I | (50 mg/ml) |
|---|---|---|
|   | Compound X | 5.0% w/v |
|   | 1M Sodium hydroxide solution | 15.0% v/v |
|   | 0.1M Hydrochloric acid (to adjust pH to 7.6) |   |
|   | Polyethylene glycol 400 | 4.5% w/v |
|   | Water for injection to 100% |   |

| (f) | Injection II | (10 mg/ml) |
|---|---|---|
|   | Compound X | 1.0% w/v |
|   | Sodium phosphate BP | 3.6% w/v |
|   | 0.1M Sodium hydroxide solution | 15.0% v/v |
|   | Water for injection to 100% |   |

| (g) | Injection III | (1 mg/ml, buffered to pH 6) |
|---|---|---|
|   | Compound X | 0.1% w/v |
|   | Sodium phosphate BP | 2.26% w/v |
|   | Citric acid | 0.38% w/v |
|   | Polyethylene glycol 400 | 3.5% w/v |
|   | Water for injection to 100% |   |

| (h) | Aerosol I | mg/ml |
|---|---|---|
|   | Compound X | 10.0 |
|   | Sorbitan trioleate | 13.5 |
|   | Trichlorofluoromethane | 910.0 |
|   | Dichlorodifluoromethane | 490.0 |

| (i) | Aerosol II | mg/ml |
|---|---|---|
|   | Compound X | 0.2 |
|   | Sorbitan trioleate | 0.27 |
|   | Trichlorofluoromethane | 70.0 |
|   | Dichlorodifluoromethane | 280.0 |
|   | Dichlorotetrafluoroethane | 1094.0 |

| (j) | Aerosol III | mg/ml |
|---|---|---|
|   | Compound X | 2.5 |
|   | Sorbitan trioleate | 3.38 |
|   | Trichlorofluoromethane | 67.5 |
|   | Dichlorodifluoromethane | 1086.0 |
|   | Dichlorotetrafluoroethane | 191.6 |

| (k) | Aerosol IV | mg/ml |
|---|---|---|
|   | Compound X | 2.5 |
|   | Soya lecithin | 2.7 |
|   | Trichlorofluoromethane | 67.5 |

-continued

|   |   |   |
|---|---|---|
|   | Dichlorodifluoromethane | 1086.0 |
|   | Dichlorotetrafluoroethane | 191.6 |

| (l) | Ointment | ml |
|---|---|---|
|   | Compound X | 40 mg |
|   | Ethanol | 300 μl |
|   | Water | 300 μl |
|   | 1-Dodecylazacycloheptan-2-one | 50 μl |
|   | Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80., polyglycerol oleate or oleic acid.

What is claimed is:

1. A compound of the Formula I

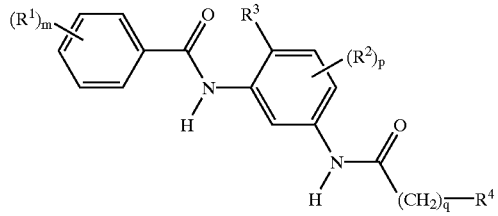

Formula I wherein $R^3$ is (1–6C)alkyl or halogeno;

$R^1$ is heterocyclyloxy wherein the heterocyclyl group in any such substituent is a non-aromatic 6-membered monocyclic nitrogen-containing ring, which may optionally bear 1 or 2 substituents selected from halogeno, (1–6C)alkyl and (1–6C)alkoxy;

and wherein any heterocyclyloxy group which contains a $CH_2$ group which is attached to 2 carbon atoms or a $CH_3$ group which is attached to a carbon atom may optionally bear on each said $CH_2$ or $CH_3$ group a substituent selected from hydroxy, amino, (1–6C)alkoxy, (1–6C)alkylamino and di-[(1–6C)alkyl]amino;

m is 1, 2 or 3;

$R^2$ is hydroxy, halogeno, trifluoromethyl, cyano, mercapto, nitro, amino, carboxy, (1–6C)alkyl, (2–6C)alkenyl, (2–6C)alkynyl, (1–6C)alkoxy, (1–6C)alkylamino or di-[(1–6C)alkyl]amino;

p is 0, 1 or 2;

q is 0; and $R^4$ is phenyl wherein $R^4$ is substituted with 1, 2 or 3 substituents, at least one such substituent being a morpholino group and any other of such substituents being selected from paragraphs (C) and (D) hereinafter:

(C) hydrogen, hydroxy, halogeno, trifluoromethyl, cyano, mercapto, nitro, amino, carboxy, carbamoyl, (1–6C)alkyl, (2–6C)alkenyl, (2–6C)alkynyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (1–6C)alkanoyl, cyano-(1–6C)alkyl, hydroxy-(1–6C)alkyl, amino-(1–6C)alkyl, (1–6C)

alkanoyloxy, (1–6C)alkanoylamino, (1–6C)
alkoxycarbonylamino, N-(1–6C)alkylsulphamoyl
and N,N-di-[(1–6C)alkyl]sulphamoyl; and
(D) (1–3C)alkylenedioxy, halogeno-(1–6C)alkyl,
(1–6C)alkoxy-(1–6C)alkyl, carboxy-(1–6C)alkyl,
(1–6C)alkoxycarbonyl-(1–6C)alkyl, carbamoyl-
(1–6C)alkyl, N-(1–6C)alkylcarbamoyl-(1–6C)alkyl,
N,N-di-[(1–6C)alkyl]carbamoyl-(1–6C)alkyl,
(1–6C)alkylamino-(1–6C)alkyl, di-[(1–6C)alkyl]
amino-(1–6C)alkyl, hydroxy-(2–6C)alkoxy-(1–6C)
alkyl, (1–6C)alkoxy-(2–6C)alkoxy-(1–6C)alkyl,
hydroxy-(2–6C)alkylamino-(1–6C)alkyl, (1–6C)
alkoxy-(2–6C)alkylamino-(1–6C)alkyl, amino-
(2–6C)alkylamino-(1–6C)alkyl, (1–6C)alkylamino-
(2–6C)alkylamino-(1–6C)alkyl, di-[(1–6C)alkyl]
amino-(2–6C)alkylamino-(1–6C)alkyl, (1–6C)
alkylthio-(1–6C)alkyl, hydroxy-(2–6C)alkylthio-
(1–6C)alkyl, (1–6C)alkoxy-(2–6C)alkylthio-(1–6C)
alkyl, hydroxy-N-(1–6C)alkyl-(2–6C)alkylamino-
(1–6C)alkyl, (1–6C)alkoxy-N-(1–6C)alkyl-(2–6C)
alkylamino-(1–6C)alkyl, amino-N-(1–6C)alkyl-
(2–6C)alkylamino-(1–6C)alkyl, (1–6C)alkylamino-
N-(1–6C)alkyl-(2–6C)alkylamino-(1–6C)alkyl, di-
[(1–6C)alkyl]amino-N-(1–6C)alkyl-(2–6C)
alkylamino-(1–6C)alkyl, trifluoromethoxy,
halogeno-(2–6C)alkoxy, hydroxy-(2–6C)alkoxy,
(1–6C)alkoxy-(2–6C)alkoxy, cyano-(1–6C)alkoxy,
carboxy-(1–6C)alkoxy, (1–6C)alkoxycarbonyl-
(1–6C)alkoxy, carbamoyl-(1–6C)alkoxy, N-(1–6C)
alkylcarbamoyl-(1–6C)alkoxy, N,N-di-[(1–6C)
alkyl]carbamoyl-(1–6C)alkoxy, amino-(2–6C)
alkoxy, (1–6C)alkylamino-(2–6C)alkoxy, di-[(1–6C)
alkyl]amino-(2–6C)alkoxy, halogeno-(2–6C)
alkylamino, hydroxy-(2–6C)alkylamino, (1–6C)
alkoxy-(2–6C)alkylamino, cyano-(1–6C)
alkylamino, carboxy-(1–6C)alkylamino, (1–6C)
alkoxycarbonyl-(1–6C)alkylamino, carbamoyl-
(1–6C)alkylamino, N-(1–6C)alkylcarbamoyl-
(1–6C)alkylamino, N,N-di-[(1–6C)alkyl]carbamoyl-
(1–6C)alkylamino, amino-(2–6C)alkylamino,
(1–6C)alkylamino-(2–6C)alkylamino, di-[(1–6C)
alkyl]amino-(2–6C)alkylamino, N-(1–6C)alkyl-
halogeno-(1–6C)alkylamino, N-(1–6C)alkyl-
hydroxy-(2–6C)alkylamino, N-(1–6C)alkyl-(1–6C)
alkoxy-(2–6C)alkylamino, N-(1–6C)alkyl-cyano-
(1–6C)alkylamino, N-(1–6C)alkyl-carboxy-(1–6C)
alkylamino, N-(1–6C)alkyl-(1–6C)alkoxycarbonyl-
(1–6C)alkylamino, N-(1–6C)alkyl-carbamoyl-
(1–6C)alkylamino, N-(1–6C)alkyl-N-(1–6C)
alkylcarbamoyl-(1–6C)alkylamino, N-(1–6C)alkyl-
N,N-di-[(1–6C)alkyl]carbamoyl-(1–6C)alkylamino,
N-(1–6C)alkyl-amino-(2–6C)alkylamino, N-(1–6C)
alkyl-(1–6C)alkylamino-(2–6C)alkylamino,
N-(1–6C)alkyl-di-[(1–6C)alkyl]amino-(2–6C)
alkylamino, (1–6C)alkanesulphonylamino,
N-(1–6C)alkyl-(1–6C)alkanesulphonylamino,
halogeno-(2–6C)alkanoylamino, hydroxy-(2–6C)
alkanoylamino, (1–6C)alkoxy-(2–6C)
alkanoylamino, cyano-(2–6C)alkanoylamino,
carboxy-(2–6C)alkanoylamino, (1–6C)
alkoxycarbonyl-(2–6C)alkanoylamino, carbamoyl-
(2–6C)alkanoylamino, N-(1–6C)alkylcarbamoyl-
(2–6C)alkanoylamino, N,N-di-[(1–6C)alkyl]
carbamoyl-(2–6C)alkanoylamino, amino-(2–6C)
alkanoylamino, (1–6C)alkylamino-(2–6C)
alkanoylamino and di-[(1–6C)alkyl]amino-(2–6C)
alkanoylamino;

and wherein any morpholino group in a substituent on $R^4$
may optionally bear 1 or 2 substituents selected from
halogeno, (1–6C)alkyl and (1–6C)alkoxy;
and wherein any of the substituents defined in paragraph
(D) hereinbefore which contain a $CH_2$ group which is
attached to 2 carbon atoms or a $CH_3$ group which is
attached to a carbon atom may optionally bear on each
said $CH_2$ or $CH_3$ group a substituent selected from
hydroxy, amino, (1–6C)alkoxy, (1–6C)alkylamino and
di-[(1–6C)alkyl]amino;
or a pharmaceutically-acceptable salt or in-vivo-cleavable
ester thereof.

2. A compound of the Formula I according to claim 1
wherein $R^3$ is methyl, ethyl, chloro or bromo;
$R^1$ is selected from piperidin-4-yloxy and
1-methylpiperidin-4-yloxy;
m is 1 or 2;
p is 0;
q is 0; and
$R^4$ is phenyl wherein $R^4$ is substituted with 1 or 2
substituents, at least one such substituents being a
morpholino group and any other of such substituents
being selected from paragraphs (C) and (D) hereinafter:
(C) hydroxy, fluoro, chloro, trifluoromethyl, cyano,
methyl, ethyl, methoxy, ethoxy, methylamino,
ethylamino, dimethylamino and diethylamino; and
(D) chloromethyl, methoxymethyl, 2-methoxyethyl,
methylaminomethyl, ethylaminomethyl,
dimethylaminomethyl, diethylaminomethyl,
2-hydroxyethylaminomethyl,
2-methoxyethylaminomethyl, 2-chloroethoxy,
3-chloropropoxy, 2-hydroxyethoxy,
3-hydroxypropoxy, 2-methoxyethoxy,
2-ethoxyethoxy, 3-methoxypropoxy,
3-ethoxypropoxy, cyanomethoxy, carboxymethoxy,
2-carboxyethoxy, methoxycarbonylmethoxy,
ethoxycarbonylmethoxy, tert-
butoxycarbonylmethoxy, 2-methoxycarbonylethoxy,
2-ethoxycarbonylethoxy, 2-tert-
butoxycarbonylethoxy, 2-aminoethoxy,
3-aminopropoxy, 2-methylaminoethoxy,
2-ethylaminoethoxy, 3-methylaminopropoxy,
3-ethylaminopropoxy, 2-dimethylaminoethoxy,
2-diethylaminoethoxy, 3-dimethylaminopropoxy,
3-diethylaminopropoxy, 2-chloroethylamino,
2-hydroxyethylamino, 2-methoxyethylamino,
2-ethoxyethylamino, 2-aminoethylamino,
2-methylaminoethylamino,
2-ethylaminoethylamino,
2-dimethylaminoethylamino,
2-diethylaminoethylamino, N-(2-chloroethyl)-N-
methylamino, N-(2-hydroxyethyl)-N-methylamino,
N-(2-methoxyethyl)-N-methylamino, N-(2-
ethoxyethyl)-N-methylamino, N-(2-aminoethyl)-N-
methylamino, N-(2-methylaminoethyl)-N-
methylamino, N-(2-dimethylaminoethyl)-N-
methylamino, N-(3-aminopropyl)-N-methylamino,
N-(3-methylaminopropyl)-N-methylamino, N-(3-
ethylaminopropyl)-N-methylamino, N-(3-
dimethylaminopropyl)-N-methylamino and N-(3-
diethylaminopropyl)-N-methylamino;
or a pharmaceutically-acceptable salt thereof.

3. A compound of the Formula I according to claim 1
wherein
m is 1, the $R^1$ group is selected from piperidin-4-yloxy or
1-methylpiperidin-4-yloxy and the $R^1$ group is located at the 3- or 4-position, or m is 2, and each $R^1$ group, which may be the same or different, is piperidin-4-yloxy or 1-methylpiperidin-4-yloxy and the $R^1$ groups are located at the 3- and 4-positions;

p is 0;

$R^3$ is methyl;

q is 0; and $R^4$ is phenyl which is substituted with 1 morpholino substituent located at the 3- or 4-position, or $R^4$ is phenyl which is substituted with 2 substituents, at least one morpholino and one optionally selected from the substituents defined in paragraphs (C) and (D) hereinafter and the substituents, which may be the same or different, are located at the 3- and 4-positions:

(C) hydroxy, fluoro, chloro, trifluoromethyl, cyano, amino, methyl, ethyl, methoxy, ethoxy, methylamino, ethylamino, dimethylamino, diethylamino, aminomethyl, 2-aminoethyl and morpholino; and (D) methylaminomethyl, ethylaminomethyl, dimethylaminomethyl, diethylaminomethyl, 2-hydroxyethylaminomethyl, 2-methoxyethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy and 3-diethylaminopropoxy;

or a pharmaceutically-acceptable salt thereof.

4. A compound of the Formula I according to claim 1 wherein m is 1, the $R^1$ group is selected from piperidin-4-yloxy and N-methylpiperidin-4-yloxy and the $R^1$ group is located at the 3- or 4-position, or m is 2 or 3, and each $R^1$ group, which may be the same or different, is selected from piperidin-4-yloxy and N-methylpiperidin-4-yloxy and is located at the 3- and 4-positions;

p is 0;

$R^3$ is methyl;

q is 0; and $R^4$ is phenyl which is substituted with 1, 2 or 3 substituents, which may be the same or different, at least one of which substituents is morpholino and any other substituent is selected from the substituents defined in paragraphs (C1), (C2) or (D) hereinafter provided that one substituent is selected from the substituents defined in paragraphs (C2) or (D) hereinafter and is located at the 3- or 4-position:

(C1) hydroxy, fluoro, chloro, trifluoromethyl, cyano, methyl, ethyl, methoxy and ethoxy;

(C2) amino, methylamino, ethylamino, dimethylamino, diethylamino, aminomethyl, 2-aminoethyl and morpholino; and (D) methylaminomethyl, ethylaminomethyl, dimethylaminomethyl, diethylaminomethyl, 2-hydroxyethylaminomethyl, 2-methoxyethylaminomethyl, 2-aminoethoxy, 3-aminopropoxy, 2-methylaminoethoxy, 2-ethylaminoethoxy, 3-methylaminopropoxy, 3-ethylaminopropoxy, 2-dimethylaminoethoxy, 2-diethylaminoethoxy, 3-dimethylaminopropoxy, 3-diethylaminopropoxy and 2-pyridylmethoxy;

or a pharmaceutically-acceptable salt thereof.

5. A compound of the Formula I according to claim 1 wherein m is 1, the $R^1$ group is selected from piperidin-4-yloxy and N-methylpiperidin-4-yloxy, and the $R^1$ group is located at the 3- or 4-position, or m is 2, and each $R^1$ group is selected from piperidin-4-yloxy and N-methylpiperidin-4-yloxy and is located at the 3- and 4-positions;

p is 0;

$R^3$ is methyl;

q is 0; and $R^4$ is phenyl which is substituted at the 3-position with a morpholino;

or a pharmaceutically-acceptable salt thereof.

6. A compound of the Formula I according to claim 1 wherein $R^3$ is methyl;

p is 0;

q is 0;

$(R^1)_m$ is selected from 3-piperidin-4-yloxy and 4-piperidin-4-yloxy; and $R^4$ is 3-morpholinophenyl, 3-fluoro-5-morpholinophenyl or 3-morpholino-5-trifluoromethylphenyl;

or a pharmaceutically-acceptable salt thereof.

7. A compound of the Formula I according to claim 1 selected from:

N-[2-methyl-5-(3-morpholinobenzamido)phenyl]-3-piperidin-4-yloxybenzamide,

N-[2-methyl-5-(3-morpholinobenzamido)phenyl]-3-(N-methylhomopiperidin-4-yloxy)benzamide, and N-[5-(3-fluoro-5-morpholinobenzamido)-2-methylphenyl]-3-piperidin-4-yloxybenzamide;

and pharmaceutically-acceptable salts thereof.

8. A process for the preparation of a compound of the Formula I, or a pharmaceutically-acceptable salt or in-vivo-cleavable ester thereof, according to claim 1 which comprises:

(a) the reaction of a compound of the Formula II

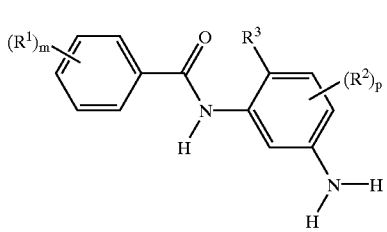

Formula II with an acid of the Formula III

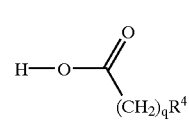

Formula III or an activated derivative thereof, under standard amide bond forming conditions, wherein variable groups are as defined in claim 1 and wherein any functional group is protected if necessary, and:

(i) removing any protecting groups;

(ii) optionally forming a pharmaceutically-acceptable salt or in-vivo-cleavable ester;

(b) the reaction of an acid of the Formula V

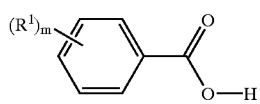

Formula V or an activated derivative thereof, with an aniline of the Formula VII

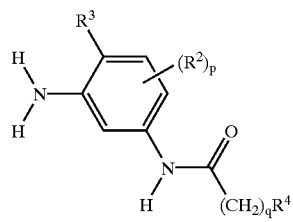

Formula VII under standard amide bond forming conditions, wherein variable groups are as defined in claim 1 and wherein any functional group is protected, if necessary, and:

(i) removing any protecting groups;
(ii) optionally forming a pharmaceutically-acceptable salt or in-vivo-cleavable ester;

(c) for the preparation of a compound of the Formula I according to claim 1 wherein $R^1$ is heterocyclyloxy or a substituent on $R^4$ is (1–6C)alkoxy or substituted (1–6C)alkoxy, (1–6C)alkylthio, (1–6C)alkylamino, di-[(1–6C)alkyl]amino or substituted (1–6C)alkylamino, the alkylation, conveniently in the presence of a suitable base, of an amide derivative of the Formula I wherein $R^1$ or a substituent on $R^4$ is hydroxy, mercapto or amino as appropriate;

(d) for the preparation of a compound of the Formula I according to claim 1 wherein a substituent on $R^4$ is (1–6C)alkanoylamino or substituted (2–6C)alkanoylamino, the acylation of a compound of the Formula I wherein a substituent on $R^4$ is amino;

(e) for the preparation of a compound of the Formula I according to claim 1 wherein a substituent on $R^4$ is (1–6C)alkanesulphonylamino, the reaction of a compound of the Formula I wherein a substituent on $R^4$ is amino with a (1–6C)alkanesulphonic acid, or an activated derivative thereof;

(f) for the preparation of a compound of the Formula I according to claim 1 wherein a substituent on $R^4$ is carboxy, carboxy-(1–6C)alkyl, carboxy-(1–6C)alkoxy, carboxy-(1–6C)alkylamino, N-(1–6C)alkyl-carboxy-(1–6C)alkylamino or carboxy-(2–6C)alkanoylamino, the cleavage of a compound of the Formula I wherein a substituent on $R^4$ is (1–6C)alkoxycarbonyl, (1–6C) alkoxycarbonyl-(1–6C)alkyl, (1–6C)alkoxycarbonyl-(1–6C)alkoxy, (1–6C)alkoxycarbonyl-(1–6C)alkylamino, N-(1–6C)alkyl-(1–6C)alkoxycarbonyl-(1–6C)alkylamino or (1–6C)alkoxycarbonyl-(2–6C)alkanoylamino as appropriate;

(g) for the preparation of a compound of the Formula I according to claim 1 wherein a substituent on $R^4$ is amino-(1–6C)alkyl, (1–6C)alkylamino-(1–6C)alkyl, di-[(1–6C)alkyl]amino-(1–6C)alkyl, substituted (2–6C)alkylamino-(1–6C)alkyl or substituted N-(1–6C)alkyl-(2–6C)alkylamino-(1–6C)alkyl, the reaction of a compound of the Formula I wherein a substituent on $R^4$ is a group of the formula -(1–6C)alkylene-Z wherein Z is a displaceable group with an appropriate amine compound;

(h) for the preparation of a compound of the Formula I according to claim 1 wherein a substituent on $R^4$ is amino, (1–6C)alkylamino, di-[(1–6C)alkyl]amino, substituted (1–6C)alkylamino, substituted N-(1–6C)alkyl-(1–6C)alkylamino, substituted (2–6C)alkylamino or substituted N-(1–6C)alkyl-(2–6C)alkylamino, the reaction of a compound of the Formula I wherein a substituent on $R^4$ is a displaceable group Z with an appropriate amine compound;

(i) for the preparation of a compound of the Formula I according to claim 1 wherein a substituent on $R^4$ is N-(1–6C)alkyl-(1–6C)alkanesulphonylamino, the alkylation, conveniently in the presence of a suitable base, of an amide derivative of the Formula I wherein a substituent on $R^4$ is (1–6C)alkanesulphonylamino;

(j) for the preparation of a compound of the Formula I according to claim 1 wherein a substituent on $R^4$ is a hydroxy-(1–6C)alkylamino-(2–6C)alkoxy group or a hydroxy-di-[(1–6C)alkyl]amino-(2–6C)alkoxy group, the reaction of a compound of the Formula I wherein a substituent on $R^4$ is a epoxy-substituted (1–6C)alkoxy group with an appropriate amine; or (k) for the preparation of a compound of the Formula I according to claim 1 wherein $R^2$ or a substituent on $R^4$ is an amino group, the reduction of a compound of the Formula I wherein $R^2$ or a substituent on $R^4$ is a nitro group.

9. A pharmaceutical composition which comprises a compound of the Formula I, or a pharmaceutically-acceptable salt or in-vivo-cleavable ester thereof, according to claim 1 in association with a pharmaceutically-acceptable diluent or carrier.

10. A method of treating a disease or medical condition mediated by a cytokine which comprises administering to a warm-blooded animal an effective amount of a compound of the Formula I, or a pharmaceutically-acceptable salt or in vivo cleavable ester thereof, according to claim 1.

* * * * *